(12) United States Patent
Shen et al.

(10) Patent No.: US 10,358,435 B2
(45) Date of Patent: Jul. 23, 2019

(54) TRIAZOLYL PYRIMIDINONE COMPOUNDS AS PDE2 INHIBITORS

(71) Applicants: Merck Sharp & Dohme Corp., Rahway, NJ (US); Dong-Ming Shen, Edison, NJ (US); Christopher J. Sinz, Middletown, NJ (US); Alejandro Crespo, Westfield, NJ (US); Johnathan E. Wilson, South Orange, NJ (US); Troy McCracken, Berkeley Heights, NJ (US); Shimin Xu, Beijing (CN); Haitang Li, Beijing (CN)

(72) Inventors: Dong-Ming Shen, Edison, NJ (US); Christopher J. Sinz, Middletown, NJ (US); Alejandro Crespo, Westfield, NJ (US); Johnathan E. Wilson, South Orange, NJ (US); Troy McCracken, Berkeley Heights, NJ (US); Shimin Xu, Beijing (CN); Haitang Li, Beijing (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/554,614

(22) PCT Filed: Mar. 11, 2016

(86) PCT No.: PCT/US2016/021902
§ 371 (c)(1),
(2) Date: Aug. 30, 2017

(87) PCT Pub. No.: WO2016/149058
PCT Pub. Date: Sep. 22, 2016

(65) Prior Publication Data
US 2018/0237422 A1    Aug. 23, 2018

(30) Foreign Application Priority Data
Mar. 17, 2015   (WO) ................ PCT/CN2015/074396

(51) Int. Cl.
| | |
|---|---|
| *C07D 471/04* | (2006.01) |
| *C07D 403/04* | (2006.01) |
| *C07D 487/04* | (2006.01) |
| *A61K 31/4192* | (2006.01) |
| *A61K 31/4196* | (2006.01) |
| *A61K 31/506* | (2006.01) |
| *C07D 498/04* | (2006.01) |
| *A61P 25/00* | (2006.01) |

(52) U.S. Cl.
CPC ........ *C07D 403/04* (2013.01); *A61K 31/4192* (2013.01); *A61K 31/4196* (2013.01); *A61K 31/506* (2013.01); *A61P 25/00* (2018.01); *C07D 471/04* (2013.01); *C07D 487/04* (2013.01); *C07D 498/04* (2013.01)

(58) Field of Classification Search
CPC .. C07D 471/04; C07D 403/04; C07D 487/04; A61K 31/4192; A61K 31/4196; A61K 31/506
See application file for complete search history.

(56) References Cited

U.S. PATENT DOCUMENTS

| | | | |
|---|---|---|---|
| 6,573,263 | B2 | 6/2003 | Niewohner et al. |
| 7,419,969 | B2 | 9/2008 | Naidu et al. |
| 8,598,155 | B2 | 12/2013 | Helal et al. |
| 8,680,116 | B2 | 3/2014 | DeLeon et al. |
| 2007/0135457 | A1 | 6/2007 | Beyer et al. |
| 2007/0281917 | A1 | 12/2007 | Naidu et al. |
| 2009/0253677 | A1 | 10/2009 | Beaulieu et al. |
| 2012/0214791 | A1 | 8/2012 | Helal et al. |
| 2014/0079666 | A1 | 3/2014 | Webb et al. |

FOREIGN PATENT DOCUMENTS

| | | |
|---|---|---|
| EP | 1097706 A1 | 5/2001 |
| EP | 1097707 A1 | 5/2001 |
| WO | WO199849166 | 11/1998 |

(Continued)

OTHER PUBLICATIONS

CAS Reg No. 1269289-66-8, etnered into STN Mar. 21, 2011. (Year: 2011).*

(Continued)

*Primary Examiner* — Rebecca L Anderson
*Assistant Examiner* — Karen Cheng
(74) *Attorney, Agent, or Firm* — Sylvia A. Ayler; John C. Todaro

(57) ABSTRACT

The present invention is directed to pyrimidine carboxamide compounds of formula I which are useful as therapeutic agents for the treatment of central nervous system disorders associated with phosphodiesterase 2 (PDE2). The present invention also relates to the use of such compounds for treating neurological and psychiatric disorders, such as schizophrenia, psychosis, Parkinson's disease, Parkinson's disease dementia (PDD), or Huntington's disease, and those associated with striatal hypofunction or basal ganglia dysfunction.

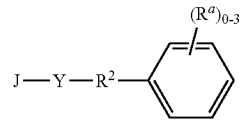

I

20 Claims, No Drawings

(56) References Cited

FOREIGN PATENT DOCUMENTS

| WO | WO200018758 | 4/2000 |
|---|---|---|
| WO | WO2003035076 | 5/2003 |
| WO | WO2003035077 A1 | 5/2003 |
| WO | WO2005041957 | 10/2004 |
| WO | WO2004096128 | 11/2004 |
| WO | WO20050614917 | 7/2005 |
| WO | WO2006024640 | 3/2006 |
| WO | WO200672615 | 7/2006 |
| WO | WO2006072615 | 7/2006 |
| WO | WO2007058646 | 5/2007 |
| WO | WO2009016498 | 2/2009 |
| WO | WO2009117540 | 9/2009 |
| WO | WO2010136493 | 12/2010 |
| WO | WO2012114222 | 8/2012 |
| WO | WO2013034758 | 9/2012 |
| WO | WO2013034761 | 9/2012 |
| WO | WO2012151567 | 11/2012 |
| WO | WO2012168817 | 12/2012 |
| WO | WO201300924 | 1/2013 |
| WO | WO2013034755 | 3/2013 |
| WO | WO2013052526 | 4/2013 |
| WO | WO2013098373 | 7/2013 |
| WO | 2013161913 | 10/2013 |
| WO | WO2014010732 | 1/2014 |
| WO | WO2014019979 | 2/2014 |
| WO | WO2014139983 | 9/2014 |
| WO | WO2015012328 | 1/2015 |
| WO | WO2005063723 | 7/2017 |

OTHER PUBLICATIONS

Ahlstrom et al., Inactivation of Atrial Natriuretic Factor-Stimulated, Biochemical Pharmacology, 2000, 1133-1139, 59.
Arulomozhi et al., Migraine: Current Therapeutic Targets and Future Avenues, Current Vascular Pharmacology, 2006, 117-128, 4.
Beavo et al., Cyclic GMP as Substrate and Regulator of Cyclic Nucleotide Phosphodiesterases (PDEs), Rev. Physio Biochem Pharm, 1999, 67-104, 135.
Bernard et al., PDE2 Is a Novel Target for Attenuating Tumor Formation in a Mouse Model of UVB-Induced Skin Carcinogenesis, Plos One, 2014, 1-8, 9.
Boess et al., Inhibition of phosphodiesterase 2 increases neuronal cGMP, synaptic plasticity and memory, Neuropharmacology, 2004, 1081-92, 47.
Boyd et al., 2-Substituted-4,5-Dihydroxypyrimidine-6-Carboxamide Antiviral Targeted Libraries, J. Comb. Chem, 2009, 1100-1104, 11.
Brandon et al., Potential CNS Applications for, Annual Reports in Medicinal Chemistry, 2007, 3-11, 42.
Bubb et al., Inhibition of Phosphodiesterase 2 Augments cGMP and, Circulation, 2014, 496-507, 268.
Cote et al., Comparative Involvement of Cyclic Nucleotide, Endocrinology, 1999, 3594-3601, 140.
Demaria et al., Highlights of the Year in JACC 2013, j. aMER. cOLL. cARD, 2014, 570-602, 63, (6).
Dickinson et al., Activation of cGMP-stimulated phosphodiesterase by nitroprusside limits, Biochem J., 1997, 371-377, 323.
Ding et al., Protective effects of phosphodiesterase 2 inhibitor on depression- and-Anxiety-Like Behaviors: Involvement of antioxidant and anti-apotoic Mechanisms, Behaviorual Brain Research, 2014, 150-158, 268.
Domek-Lopacinska et al., The Effect of Selective Inhibition of Cyclic GMP Hydrolyzing Phosphodiesterases 2 and 5 on Learning and Memory Processes and Nitric Oxide Synthase Activity, Brain Research, 2008, 68-77, 1216.
Ducrot et al., CoMFA and CoMSIA 3D-Quantitative Structure-Activity Relationship Model on Benzodiaepine Derivatives, Inhibitors of Phosphodiesterase IV, J. of Computer Aided Molecular Designs, 2001, 767-785, 15.
Duran et al., The NO cascade, eNOS Location, and Microvascular Permeability, Cardiovascular Research, 2010, 254-261, 87.
Favot et al., VEGF-Induced HUVEC Migration and Proliferation, Schattauer GmbH Stuttgart, 2003, 3443-343, 90.
Gergega et al., Systematic Effect of Benzo-Annelation on Oxo-Hydroxy Tautomerism of Heterocyclic, J. Phys. Chem A., 2007, 4934-4943, 111.
Giuliano et al., Correction to Tautomerism in 4-Hydroxypyrimidine, S-Methyl-2-thiouracil, and 2-Thiouracil, The Journal of Physical Chemistry A, 2011, 8178-8179, 115.
Giuliano et al., Tautomerism in 4-Hydroxypyrimidine, S-Methyl-2-thiouracil, and 2-Thiouracil, J. Phys. Chem. A, 2010, 12725-12730, 114.
Haynes et al., Erythro-9-(2-Hydroxy-3-Nonyl) Adenine Inhibits Cyclic-3',5' Guanosine Monophosphate-Stimulated Phosphodiesterase to Reverse Hypoxic Pulmonary Vasoconstriction in the Perfused Rat Lung, The J. of Pharmacology, 1996, 752-757, 276.
Herring et al., NO-cGMP Pathway Increases the Hyperpolarisation-Activated Current ,I, and Heart Rate During Adrenergic Stimulation, Cardiovascular Research, 2001, 446-453, 52.
Hiramoto et al., Role of Phosphodiesterase 2 in Growth and Invasion of HUman Maligant Melanoma, Cellular Signaling, 2014, 1807-1817, 26.
Huang et al., A Fluroescence Polarization Assay for Cyclic Nucleotide Phosphodiesterases, J. of Biomolecular Screening, 2002, pp. 215-222, 7.
Jorgensen et al., Selective Inhibitors of PDE2, PDE9, and PDE10: Modulators of Activity of the Central Nervous System, Annual Reports in Medicinal Chemistry, 2013, pp. 37-55, 48.
Keravis et al., Cyclic Nucleotide Hydrolysis in Bovine Aortic Endothelial Cells in Culture: Differential Regulation in Cobblestone and Spindle Phenotypes, J. Vasc. Res, 2000, 235-249, 37.
Kheifets et al., Structure and Amide-Amide Tautomerism of 4-Hydroxypyrimidines. Determination of the Tautomeric Composition by 13C NMR Spectroscopy, Russ. J. of Organic Chemistry, 2000, 1373-1387, 36, 9.
Lieberman et al., Effectiveness of Antipsychotic Drugs in Patients with Chronic Schizophrenia, New England J. of Medicine, Sep. 22, 2005, pp. 1209-1223, 353, US.
Lopez et al., Solution and solid state (CPMAS) NMR Studies of the Tautomerism of Six-Membered Heterocyclic Compounds Related to 2-Pyridones, Spectroscopy, 2000, pp. 121-126, 14.
Masood et al., Anxiolytic Effects of Phosphodiesterase-2 Inhibitors Associated with Increased cGMP Signaling, J. of Pharmacology, 2009, 690-699, 331.
Masood et al., Reversal of Oxidative Stress-Induced Anxiety by Inhibition of Phosphodiesterase-2 in Mice, J. of Pharmacology and Experimental Therapeutics, 2008, 369-379, 326.
Michie et al., Rapid Regulation of PDE-2 and PDE-4 Cyclic AMP Phosphodiesterase Activity Folloiwng Ligation of the T Cell Antigen Receptor on Thymocytes: Analysis Using theSelctive Inhibitors Erythro-9-(2-Hydroxy-3Nonyl)-Adenine (EHNA) and Rolipram, Cell Signal, 1996, 97-110, 8.
Morita et al., Characterization of Phosphodiesterase 2A in Human Malignant Melanoma PMP Cells, Oncology Reports, 2013, 1275-1284, 29.
Netherton et al., Vascular Endothelial Cell Cyclic Nucleotide phosphodiesterases and Regulated Cell Migration: IMplications in Angiogenesis, Molecular Pharmacology, 2005, 263-272, 67.
P. C. Tfelt-Hansen et al., One Hundred Years of Migraine Research: Major Clinical and, Headache, 2011, 752-778, 51.
Pace et al., Dihydroxypyrimidine-4-Carboxamides as Novel Poten and Selective HIV Integrase Inhibitors, J. Med Chem., 2007, 2225-2239, 50.
Petrocchi et al., From dihydroxypyrimidine carboxylic acids to carboxamide, Bioorganic & Medicinal Chemistry Letters, 2007, 350-353, 17.
Plummer et al., Discovery of Poten, Selective, Bioavailable Phosphodiesterase 2 (PDE2) Inhibitors Active in an Osteoarthritis Pain Model, Part I: Transformation of Selective Pyrazolodiazepinone Phosphodiesterase 4 (PDE4) Inhibitors into Selective PDE2 Inhibitors, Biorganic & Medicinal Chemistry Letters, 2013, 3438-3442, 23.

(56) References Cited

OTHER PUBLICATIONS

Plummer et al., Discovery of potent selective bioavailable phosphodiesterase, Bioorganic & Medicinal Chemistry Letters, 2013, 3443-3447, 23.
Reierson et al., Repeated antidepressant therapy increases cyclic GMP signaling, Neurosci Letter, 2009, 149-153, 466 (3).
Rivet-Bastide et al., cGMP-stimulated Cyclic Nucleotide Phosphodiesterase Regulates the Basal, J. Clin. Invest, 1997, 2710-2718, 99.
Sadhu et al., Differential Expression of the Cyclic GMP-Stimulated Phosphodiesterase PDE2A in HUman Venous and Capillary Endothelial Cells, J. of Histochemistry & Cytochemistry, 1999, 895-905, 47.
Sanchez et al., Gas-Phase Tautomeric Equilibrium of 4-Hydroxypyrimidine, J. Am. Chem Soc., 2007, 6287-6290, 129.
Savai et al., Targeting Cancer with Phosphodiesterase Inhibitors, Expert Opinion, 2010, 117-131, 19.
Surapisitchat et al., Differential Regulation of Endothelial Cell Permeability by cGMP via Phosphodiesterases 2 and 3, Circulation Research, 2007, 811-818, 101.
Suvrana et al., Hydrolysis of N-Methyl-D-aspartate Receptor-Stimulated cAMP, J. of Pharmacology, 2002, 249-256, 302.
Van Staveren et al., The effects of phosphodiesterase inhibition on cyclic GMP and cyclic, Brain Research, 2001, 275-286, 888.
Vandecasteele, Cyclic GMP regulation of the L-type Ca2+ channel current, J. of Physiology, 2001, 329-340, 533.
Velardez et al., Role of Phosphodiesterase and Protein Kinase G on Nitric Oxide-Induced Inhibition of Prolactin Release from the Rat Anterior Pituitary, Europe J. of Endocrinology, 2000, 279-284, 143.
Wakabayashi et al., Involvement of Phosphodiesterase Isozymes in Osteoblastic, J. of Bone and Mineral Research, 2002, 249-253, 17.

\* cited by examiner

TRIAZOLYL PYRIMIDINONE COMPOUNDS AS PDE2 INHIBITORS

CROSS REFERENCE TO RELATED APPLICATIONS

This application is the National Stage of International Application No. PCT/US2016/021902 filed on Mar. 11, 2016, which claims the benefit under International Application No PCT/CN2015/074396, filed Mar. 17, 2015.

FIELD OF THE INVENTION

The invention relates generally to compounds which act as inhibitors of the phosphodiesterase (PDE) 2 enzyme, compositions and therapeutic uses thereof.

BACKGROUND OF THE INVENTION

Schizophrenia is a debilitating disorder affecting the psychic and motor functions of the brain. It is typically diagnosed in individuals in their early to mid-twenties and symptoms include hallucinations and delusions or at the other extreme, anhedonia or social withdrawal. Across the spectrum, the symptoms are indicative of cognitive impairment and functional disabilities. Notwithstanding improvements in antipsychotic treatments, current therapies, including typical (haloperidol) and atypical (clozapine or olanzapine) antipsychotics, have been less than acceptable and result in an extremely high rate of noncompliance or discontinuation of medication. Dissatisfaction with therapy is attributed to lack of efficacy or intolerable and unacceptable side effects. The side effects have been associated with significant metabolic, extrapyramidal, prolactic and cardiac adverse events. See, Lieberman et al., N. Engl. J. Med. (2005) 353:1209-1223.

While multiple pathways are believed to be involved with the pathogenesis of schizophrenia leading to psychosis and cognition deficits, much attention has focused on the role of glutamate/NMDA dysfunction associated with cyclic guanosine monophosphate (cGMP) levels and the dopaminergic receptors associated with cyclic adenosine monophosphate (cAMP). These ubiquitous secondary messengers are responsible for altering the function of many intracellular proteins. Cyclic AMP is thought to regulate the activity of cAMP-dependent protein kinase (PKA), which in turn phosphorylates and regulates many types of proteins including ion channels, enzymes and transcription factors. Similarly, cGMP is also responsible for downstream regulation of kinases and ion channels.

One pathway for affecting the levels of cyclic nucleotides, such as cAMP and cGMP, is to alter or regulate the enzymes that degrade these secondary messengers, known as 3', 5'-cyclic nucleotide specific phosphodiesterases (PDEs). The PDE superfamily includes twenty-one genes that encode for eleven families of PDEs. These families are further subdivided based on catalytic domain homology and substrate specificity and include the 1) cAMP specific, PDE4A-D, 7A and 7B, and 8A and 8B, 2) cGMP specific, PDE 5A, 6A-C, and 9A, and 3) those that are dual substrate, PDE 1A-C, 2A, 3A and 3B, 10A, and 11A. The homology between the families, ranging from 20% to 45%, suggests that it may be possible to develop selective inhibitors for each of these families.

PDE2 is highly expressed in the brain, but is also found in many other tissues as well, and therefore has a broad array of function and utility (J. A. Beavo, et al., Rev. Physio. Biochem. Pharm., 135, 67 (1999)). Amongst others, PDE2 has been shown to have therapeutic potential in neuronal development, learning, and memory (W. C. G. van Staveren, et al., Brain Res., 888, 275 (2001) and J. O'Donnell, et al., J. Pharm. Exp. Ther., 302, 249 (2002)); prolactin and aldosterone secretion (M. O. Velardez, et al., Eur. J. Endo., 143, 279 (2000) and N. Gallo-Payet, et al., Endo., 140, 3594 (1999)); bone cell differentiation, growth, and bone resorption (C. Allardt-Lamberg, et al., Biochem. Pharm., 59, 1133 (2000) and S. Wakabayashi, et al., J. Bone, Miner. Res., 17, 249 (2002); immunological response (M. D. Houslay, et al., Cell. Signal., 8, 97 (1996); vascular angiogenesis (T. Keravis, et al., J. Vasc. Res., 37, 235 (2000); inflammatory cell transit (S. L. Wolda, et al., J. Histochem. Cytochem., 47, 895 (1999); cardiac contraction (R. Fischmeister, et al., J. Clin. Invest., 99, 2710 (1997), P. Donzeau-Gouge, et al., J. Physiol., 533, 329 (2001), and D. J. Paterson, et Al., Card. Res., 52, 446 (2001); platelet aggregation (R. J. Haslam, et Al., Biochem. J., 323, 371 (1997); female sexual arousal disorder (C. P. Wayman, et al., EP Patent Publications EP10977707 and EP1097706); osteoarthritis pain (M. Plummer et. al., Bioorganic & Medicinal Chemistry Letters, 23(11), 3438-3442 and 3443-3447 (2013)); malignant melanoma (H. Morita, et al., Oncology Reports, 29, 1275-1284, 2013; Hiramoto, et al., Cell. Signal., 26(9), 1807-1817, 2014; and J. J. Bernard, et al., PloS ONE 9(10): e109862, 2014); heart failure (A. N. DeMaria, et al., J. Amer. Coll. Card. 63 (6), 570-602, 2014); pulmonary hypertension (K. J, Bubb, et al., Circulation, 130, 496-508, 2014); depression and anxiety (L. Ding, et al., Behav. Brain Res. 268, 150-158, 2014); and hypoxic pulmonary vasoconstriction (J. Haynes, et. al., J. Pharm. Exp. Ther., 276, 752 (1996). See also 2-Substituted-4,5-dihydroxypyrimidine-6-carboxamide Antiviral Targeted Libraries, Vincent Boyd et al., Journal of Combinatorial Chemistry (2009), 11(6), 1100-1104; From Dihydroxypyrimidine Carboxylic Acids to Carboxamide HIV-1 Integrase Inhibitors: SAR Around the Amide Moiety, Alessia Petrocchi et al., Bioorganic & Medicinal Chemistry Letters (2007), 17(2), 350-353; Dihydroxypyrimidine-4-carboxamides as Novel Potent and Selective HIV Integrase Inhibitors, Paola Pare et al., Journal of Medicinal Chemistry (2007), 50(9), 2225-2239; US2007135457, WO2012151567, US20090253677, US20070281917, WO2004096128, WO2003035077, WO2003035076, WO2007058646, WO2009117540, and U.S. Pat. No. 7,419, 969.

Inhibition of PDE2 (e.g., PDE2A) has been shown to enhance cognitive function across multiple preclinical models of cognitive performance that reflect improvements in recognition memory, social interactions and working memory, which are all deficient in schizophrenia (Boess et al., *Inhibition of Phosphodiesterase 2 Increases Neuronal cGMP, Synaptic Plasticity and Memory Performance*, Neuropharmacology, 47(7):1081-92, 2004). PDE2A inhibition was also shown to improve cognitive deficits that develop in aging and Alzheimer's disease (Domek-Lopacinska and Strosznajder, *The Effect of Selective Inhibition of Cyclic GMP Hydrolyzing Phosphodiesterases 2 and 5 on Learning and Memory Processes and Nitric Oxide Synthetase Activity in Brain During Aging*, Brain Research, 1216:68-77, 2008). The role of PDE2 inhibition in cognitive disorders was also shown in Brandon et al., *Potential CNS Applications for Phosphodiesterase Enzyme Inhibitors*, Annual Reports in Medicinal Chemistry 42: 4-5, 2007 (compound BAY 60-7550 was reported to have significant potency at other PDE isoforms, had high clearance and limited brain penetration). See also Jorgenson, et al, Annual Reports in Medicinal Chemistry 48: 37-55, 2013. "Selective Inhibitors of PDE2, PDE9, and PDE10: Modulators of Activity of the Central Nervous System".

PDE2 inhibitors have also been shown to have efficacy in preclinical models of anxiety and depression (Masood et al., Anxiolytic Effects of Phosphodiesterase-2 Inhibitors Associated with Increased cGMP Signaling, JPET 331(2):690-699, 2009; Masood et al., Reversal of Oxidative Stress-Induced Anxiety by Inhibition of Phosphodiesterase-2 in Mice, JPET 326(2):369-379, 2008; Reierson et al., Repeated Antidepressant Therapy Increases Cyclic GMP Signaling in Rat Hippocampus, Neurosci. Lett., 466(3):149-53, 2009). See also Ducrot et al., CoMFA and CoMSIA 3D-quantitative structure-activity relationship model on benzodiazepine derivatives, inhibitors of phosphodieserase IV, J Computer-Aided Molecular Design, 15: 767785, 2001; US20120214791; WO2012168817; WO2013034755; WO2013034758; WO2013034761; WO2005041957; WO2005061497; WO2006024640; WO2013161913; WO2010136493; WO 2013098373; WO 2009016498; U.S. Pat. Nos. 6,573,263; 8,598,155; and 8,680,116; WO2015012328; WO2014139983; WO2014019979; WO2014010732; WO2013000924; WO2012114222; WO2006072615; WO2005063723; M. Plummer et al., Bioorg Med Chem Lett 23(11), 3438, 2013; and M. Plummer et al., Bioorg Med Chem Lett 23(11), 3443, 2013.

An increase in vascular permeability has been shown to be attributable to increased activity of PDE2. PDE2 and PDE3 in the endothelium can act as a sensor or switch to detect normal versus pathological concentrations of cGMP and thus regulate endothelial permeability accordingly with potential relevance to migraine. See Surapisitchat et al., *Differential Regulation of Endothelial Cell Permeability by cGMP via Phosphodieserase 2 and 3*, Circulation Research, 2007; 101, pgs.: 811-818 and Duran et al., *The NO Cascade, eNOS Location and Microvascular Permeability*, Cardiovascular Res. (2010) 87, 254-261. Cerebral vasodilation is considered a major cause of migraine. See P. C. Tfelt-Hansen and P. J. Koehler, *One hundred years of migraine research: major clinical and scientific observations from 1910 to 2010*, Headache, 2011. 51(5), 752-578 and D. K. Arulmozhi et al., *Migraine: current therapeutic targets and future avenues*, Current Vascular Pharmacology, 2006, 4(2), 117-128. Therefore, PDE2 inhibition may have utility as a treatment or prophylactic for migraine.

The need for new and improved PDE2 modulators believed to be useful for treating diseases or disorders associated with PDE2 such as Alzheimer's disease, cognitive impairment associated with schizophrenia, depression, migraines, and the like continues to exist. Inhibitors of PDE2 are not only believed to be useful in treating schizophrenia but also a wide variety of conditions or disorders that would benefit from increasing levels of cAMP and/or cGMP within neurons, including a variety neurological, psychotic, anxiety and/or movement disorders. Accordingly, agents that inhibit PDE2 and PDE2A would be desirable as therapeutics for neurological and psychiatric disorders.

SUMMARY OF THE INVENTION

The present invention is directed to triazolyl pyrimidinone compounds which may be useful as therapeutic agents for the treatment of central nervous system and/or peripheral disorders associated with phosphodiesterase 2 (PDE2). The present invention also relates to the use of such compounds for treating neurological and psychiatric disorders, such as schizophrenia, psychosis, Alzheimer's, cognitive impairment, anxiety, depression, migraines, or Huntington's disease, Parkinson's disease, Parkinson's disease dementia (PDD), and other diseases associated with striatal hypofunction or basal ganglia dysfunction.

DETAILED DESCRIPTION OF THE INVENTION

The present invention is directed to triazolyl pyrimidinone compounds of formula I:

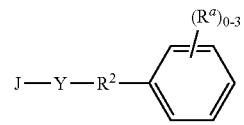

I or a pharmaceutically acceptable salt or solvate thereof, wherein:

J represents pyrimidinone optionally substituted with 1 to 2 groups selected from $C_{1-6}$alkyl, $C_{2-6}$alkenyl, $(CH_2)_nC_{3-10}$cycloalkyl, and $(CH_2)_nC_{6-10}$aryl, said alkyl and aryl optionally substituted with one to three groups of $R^a$;

Y is triazolyl optionally substituted with $R^b$;

$R^2$ is selected from the group consisting of $CR^xR^y$;

or $R^2$ and the available carbon atom and/or nitrogen atom of the Y triazolyl can combine to form an 8 to 10 membered heterocyclyl optionally interrupted with one or more heteroatoms selected from O, S, and N, and said heterocyclyl optionally substituted with 1 to 3 groups of $R^b$;

$R^x$ and $R^y$ are independently selected from the group consisting of H, $(CH_2)_nOR$, $C_{1-6}$alkyl, $C_{3-6}$ cycloalkyl, C(O)OR and $N(R)_2$, said alkyl optionally substituted with one to three groups of $R^a$;

or $R^x$ and $R^y$ can combine with the carbon atom to which they are attached to form a group selected from C=O, $C_{3-6}$ cycloalkyl and $C_{3-6}$ heterocyclyl;

R represents H, or $C_{1-6}$ alkyl, $R^a$ is selected from the group consisting of H, halo, CN, $(CH_2)_nOR$, $(O)_pC_{1-4}$haloalkyl, C(O)OR, $—O(CH_2)_nN(R)_2$, $(CHR)_nN(R)_2$, $NO_2$, $SCF_3$, $S(O)_sCF_3$, $S(O)_sR$, $SF_5$, $C_{3-10}$cycloalkyl, $O—C_{3-10}$ cycloalkyl, $C_{5-10}$heterocyclyl, and $C_{6-10}$aryl, said alkyl, cycloalkyl, heterocyclyl and aryl optionally substituted with one to three groups of $R^b$;

$R^b$ is selected from the group consisting of H, halo, $C_{1-6}$alkyl, $(CH_2)_nOR$, and $(O)_pC_{1-4}$haloalkyl;

n represents 0, 1, 2, 3, or 4;

s represents 0, 1, or 2; and p represents 0 or 1.

An embodiment of the invention of formula I is realized when the pyrimidinone J is represented by structural formula I^

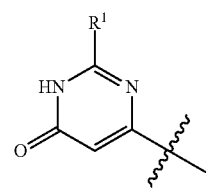

I^ wherein R¹ is selected from the group consisting of H, $C_{1-6}$alkyl, $C_{2-6}$alkenyl, $(CH_2)_nC_{3-10}$cycloalkyl, and $(CH_2)_n$$C_{6-10}$aryl, said alkyl and aryl optionally substituted with one to three groups of $R^a$.

Another embodiment of the invention of formula I is realized when Y is triazolyl wherein one of its nitrogen atoms is attached to R² and one of its carbon atoms is attached to J. Still another embodiment of the invention of formula I is realized when Y is triazolyl wherein one of its nitrogen atoms is attached to J and one of its carbon atoms is attached to R².

Another embodiment of the invention of formula I is realized when Y is triazolyl selected from the group consisting of

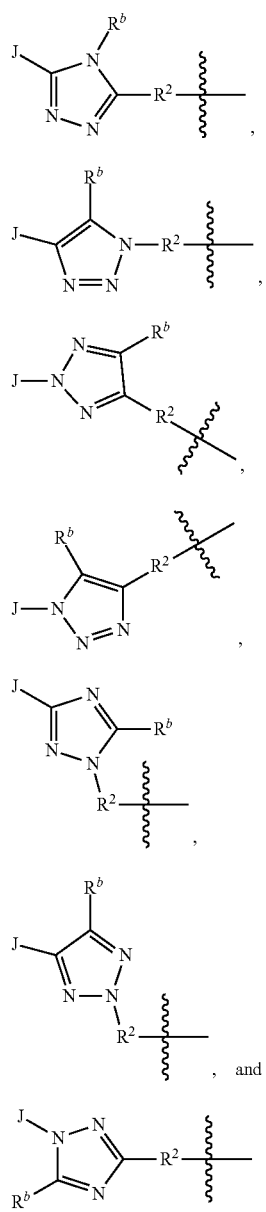

wherein R², and $R^b$ are as originally described and the ~ line represents the point of attachment.

An aspect of this subembodiment of the invention of formula I is realized when Y is (a), (b), (c), (d), (e), (f), or (g) and $R^b$ is hydrogen. Another aspect of this subembodiment of the invention of formula I is realized when Y is (a). Another aspect of this subembodiment of the invention of formula I is realized when Y is (b). Another aspect of this subembodiment of the invention of formula I is realized when Y is (c). Another aspect of this subembodiment of the invention of formula I is realized when Y is (d). Another aspect of this subembodiment of the invention of formula I is realized when Y is (e). Another aspect of this subembodiment of the invention of formula I is realized when Y is (f). Another aspect of this subembodiment of the invention of formula I is realized when Y is (g).

Another aspect of this subembodiment of the invention of formula I is realized when the triazole Y is (a), (b), (c), (d), or (e), and R² and $R^b$ on the triazolyl combine to form an optionally substituted ring fused to the triazole. A further aspect of this embodiment of the invention is realized when R² and $R^b$ on the triazolyl combine to form a group consisting of tetrahydrotriazolopyridinyl, dihydrotriazolooxazinyl, dihydropyrrolotriazolyl, and tetrahydrotriazoloazepinyl.

Another embodiment of the invention is realized when R¹ is selected from the group consisting of hydrogen, methyl, ethyl, isopropyl, propyl, butyl, isobutyl, pentyl, cyclopropyl, cyclobutyl, cyclopentyl, cyclohexyl, phenyl, ethenyl, propenyl, butenyl, and pentenyl.

Another embodiment of the invention is realized when R¹ is hydrogen.

Another embodiment of the invention is realized when R¹ is optionally substituted $C_{1-6}$alkyl. An aspect of this embodiment of the invention is realized when R¹ is optionally substituted methyl, ethyl, isopropyl, propyl, butyl, isobutyl, pentyl and the like. Still another aspect of this embodiment of the invention is realized when R¹ is methyl.

Still another embodiment of the invention is realized when R¹ is $(CH_2)_nC_{3-10}$cycloalkyl. An aspect of this embodiment of the invention is realized when R¹ is cyclopropyl, cyclobutyl, cyclopentyl, cyclohexyl and the like.

Yet another embodiment of the invention is realized when R¹ is $(CH_2)_nC_{6-10}$ aryl. An aspect of this embodiment of the invention is realized when the aryl of R¹ is optionally substituted phenyl.

Another embodiment of the invention is realized when R¹ is optionally substituted $C_{2-6}$alkenyl. An aspect of this embodiment of the invention is realized when R¹ is optionally substituted ethenyl, propenyl, butenyl or pentenyl.

Another embodiment of the invention is realized when R² is $CH(CH_2)_nCH_3$, $C(CH_3)_2$, $CH(CH(CH_3)_2)$, $CH_2$, $-C(=O)-$, $CH(CH_2)_nOH$, $C(CH_3)(OH)$, $CHC(O)OCH_3$, $CH(NHCH_3)$, $CH(CH_2)_n(OCH_3)$, CH-cyclopropyl, cyclobutyl, tetrahydrofuranyl. An aspect of this embodiment of the invention is realized when R² is $CH(CH_2)_nCH_3$, or $CHCH_3$.

Another embodiment of the invention is realized when $R^x$ and $R^y$ are independently selected from the group consisting of H, methyl, ethyl, propyl, isopropyl, butyl, isobutyl, pentyl, $(CH_2)_nOH$, C(O)OR, $NHCH_3$, $NH_2$, $NHCH_2CH_3$, $OCH_3$, $O(CH_2)_nCH_3$, said methyl, ethyl, propyl, isopropyl, butyl, isobutyl, and pentyl optionally substituted with 1 to 3 groups of OH.

Another embodiment of the invention is realized when one of $R^x$ and $R^y$ is hydrogen and the other is selected from the group consisting of $(CH_2)_nOR$, $C_{1-6}$alkyl, C(O)OR and $N(R)_2$, said alkyl optionally substituted with one to three groups of $R^a$.

Another embodiment of the invention is realized when $CR^xR^y$ of R² is selected from the group consisting of CH(CH$_2$)$_n$CH$_3$, C(CH$_3$)$_2$, CH(CH(CH$_3$)$_2$), CH$_2$, —C(=O)—, CH(CH$_2$)$_n$OH, C(CH$_3$)(OH), CHC(O)OCH$_3$, CH(NHCH$_3$), CH(CH$_2$)$_n$(OCH$_3$), CH-cyclopropyl, cyclobutyl, CH-cyclobutyl, tetrahydrofuranyl. An aspect of this embodiment of the invention is realized when R$^2$ is CH(CH$_2$)$_n$CH$_3$, or CHCH$_3$.

Still another embodiment of the invention is realized when R$^x$ and R$^y$ together with the carbon atom to which they are attached are combined to form a group selected from —C=O—, C$_{2-6}$ alkenyl, C$_{3-6}$ cycloalkyl and C$_{3-6}$ heterocyclyl. An aspect of this aspect of the invention is realized when R$^x$ and R$^y$ together with the carbon atom to which they are attached form —C=O—. Another aspect of this aspect of the invention is realized when R$^x$ and R$^y$ together with the carbon atom to which they are attached form C$_{2-6}$ alkenyl. Another aspect of this aspect of the invention is realized when R$^x$ and R$^y$ together with the carbon atom to which they are attached form C$_{3-6}$ cycloalkyl, selected from the group consisting of cyclopropyl, cyclobutyl, cyclopentyl and the like. Another aspect of this aspect of the invention is realized when R$^x$ and R$^y$ together with the carbon atom to which they are attached form C$_{3-6}$ heterocyclyl such as tetrahydrofuranyl.

Another embodiment of the invention is realized when R$^2$ and the available carbon atom and/or nitrogen atom of the Y triazolyl can combine to form an 8 to 10 membered heterocyclyl optionally interrupted with one or more heteroatoms selected from O, S, and N, and said heterocyclyl optionally substituted with 1 to 3 groups of R$^b$. An aspect of this embodiment is realized when the optionally substituted 8 to 10 membered heterocyclyl formed is a bicyclic ring structure or an optionally substituted 8 to 10 membered fused triazole having 3 to 5 carbon atoms. Another aspect of this embodiment is realized when the heterocyclyl formed is attached to the phenyl group of Formula I and Ia via a carbon atoms.

An aspect of this invention is realized when R$^2$ and the available carbon and/or nitrogen atom of the Y triazolyl combine to form a heterocyclyl selected from the group consisting of tetrahydrotriazolopyridinyl, dihydrotriazolooxazinyl, dihydropyrrolotriazolyl, and tetrahydrotriazoloazepinyl.

Another embodiment of the invention of formula I is realized when R$^a$ is selected from H, OH, halo, (CH$_2$)$_n$CH$_3$, CH(CH$_3$)$_2$, C(CH$_3$)$_3$, C(O)OCH$_3$, (CH$_2$)$_n$OCH$_3$, OC(CH$_3$)$_2$, CH$_2$F, CHF$_2$, (CH$_2$)$_n$CF$_3$, OCHF$_2$, OCF$_3$, SCH$_3$, SCF$_3$, SF$_5$, SOCF$_3$, SO$_2$CF$_3$, SO$_2$CH$_3$, CH$_2$NH$_2$, (CH$_2$)$_n$N(CH$_3$)$_2$, NO$_2$, CN, cyclobutyl, cyclopropyl, phenyl, naphthyl, pyrimidinyl, pyridyl, said groups, where appropriate, optionally substituted with one to three groups of R$^b$. Another embodiment of the invention of formula I is realized when R$^a$ is selected from OH, halo, (CH$_2$)$_n$CH$_3$, CH(CH$_3$)$_2$, C(CH$_3$)$_3$, (CH$_2$)$_n$OCH$_3$, OC(CH$_3$)$_2$, CH$_2$F, CHF$_2$, CF$_3$, OCHF$_2$, OCF$_3$, SCH$_3$, SCF$_3$, SF$_5$, SOCF$_3$, SO$_2$CF$_3$, SO$_2$CH$_3$, CH$_2$NH$_2$, (CH$_2$)$_n$N(CH$_3$)$_2$, NO$_2$, CN, cyclobutyl, cyclopropyl, and phenyl, said groups, where appropriate, optionally substituted with one to three groups of R$^b$.

Another embodiment of the invention of formula I is realized when R$^a$ on the phenyl group of the compound of Formula I and Ia is selected from the group consisting of halo, (CH$_2$)$_n$CH$_3$, CH$_2$F, (CH$_2$)$_n$CF$_3$, OCHF$_2$, OCF$_3$, and SF$_5$. Another aspect of this embodiment of the invention is realized when the phenyl group of Formula I and Ia is substituted with at least two R$^a$ groups. Still another aspect of this embodiment of the invention is realized when the phenyl group of Formula I and Ia is substituted with at least two R$^a$ groups selected from CF$_3$ and halo, wherein the halo is selected from fluorine and chlorine.

Another embodiment of the invention of formula I is realized when n is 0. Another embodiment of the invention of formula I is realized when n is 1. Another embodiment of the invention of formula I is realized when n is 2. Another embodiment of the invention of formula I is realized when n is 3. Still another embodiment of the invention of formula I is realized when n of R$^a$ is 0-1, 0-2, or 0-3.

Still another embodiment of the invention is realized when it is represented by structural formula Ia:

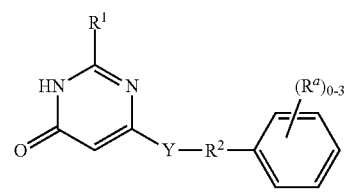

Ia or a pharmaceutically acceptable salt or solvate thereof. An aspect of this invention is realized when Y—R$^2$ is selected from the group consisting of

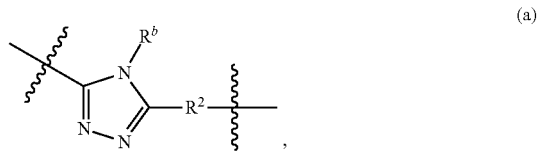

(a)

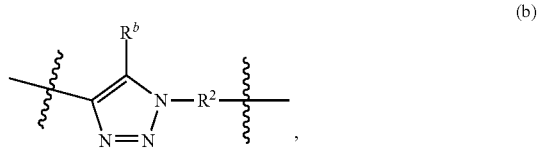

(b)

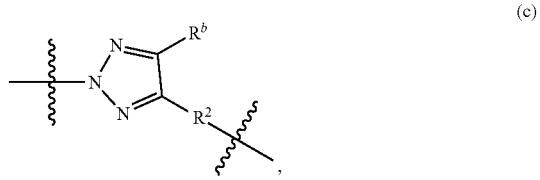

(c)

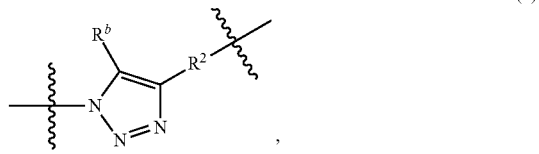

(d)

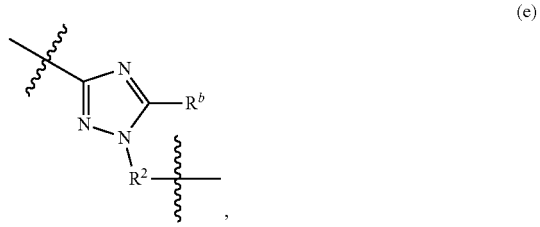

(e)

-continued

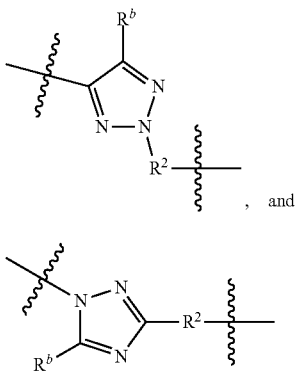

(f)

, and (g)

$R^b$ is hydrogen in (a), (b), (c), (d), (e), (f), and (g), $R^1$ is selected from the group consisting of H, or optionally substituted $C_{1-6}$alkyl cyclopropyl, cyclobutyl, and phenyl and $R^2$ is selected from the group consisting of $CH(CH_2)_n$ $CH_3$, $CHCH(CH_3)_2$, $CH_2$, —C═O—, $CH(CH_2)_nOH$, $C(CH_3)(OH)$, $CHC(O)OCH_3$, $CH(NHCH_3)$, $CH(CH_2)_n$ $(OCH_3)$, cyclobutyl, tetrahydrofuranyl. Another embodiment of this aspect of the invention of formula Ia is realized when $R^2$ is $CH(CH_2)_nCH_3$.

A subembodiment of the invention of formula Ia is realized when Y is (a). Another subembodiment of the invention of formula Ia is realized when Y is (b). Another subembodiment of the invention of formula Ia is realized when Y is (c). Another subembodiment of the invention of formula Ia is realized when Y is (d). Another subembodiment of the invention of formula Ia is realized when Y is (e). Still another subembodiment of the invention of formula Ia is realized when Y is (f). Yet another subembodiment of the invention of formula Ia is realized when Y is (g).

Another embodiment of the invention of formula Ia is realized when $R^2$ and the available carbon and/or nitrogen atoms of the Y triazolyl combine to form a $C_{8-10}$ heterocyclyl selected from the group consisting of optionally substituted tetrahydrotriazolopyridinyl, dihydrotriazolooxazinyl, dihydropyrrolotriazolyl, and tetrahydrotriazoloazepinyl.

Another aspect of the invention of formula Ia is realized when Y is (a), $R^b$ is H, $R^1$ is optionally substituted methyl, and $R^2$ is $CH(CH_2)_nCH_3$.

Another aspect of the invention of formula Ia is realized when Y is (b), $R^b$ is H, $R^1$ is optionally substituted methyl, and $R^2$ is $CH(CH_2)_nCH_3$.

Another aspect of the invention of formula Ia is realized when Y is (d), $R^b$ is H, $R^1$ is optionally substituted methyl, and $R^2$ is $CH(CH_2)_nCH_3$.

Another aspect of the invention of formula Ia is realized when Y is (f), $R^b$ is H, $R^1$ is optionally substituted methyl, and $R^2$ is $CH(CH_2)_nCH_3$.

The invention is also directed to a method for the treatment of central nervous system disorders associated with phosphodiesterase 2 (PDE2) using the compounds of Formula I. More specifically, the present invention relates to the use of such compounds for treating neurological and psychiatric disorders, such as schizophrenia, psychosis, Alzheimer's, cognitive impairment, anxiety, depression, migraines, or Huntington's disease, Parkinson's disease, Lewy body dementia, and other diseases associated with striatal hypofunction or basal ganglia dysfunction using the compounds of formula I.

Examples of compounds of the invention can be found throughout the specification.

The invention also encompasses pharmaceutical compositions containing a compound of formula I and methods for treatment or prevention of phosphodiesterase mediated diseases using compounds of formula I.

Where a variable occurs more than once in any formula of the invention, or in a substituent thereof, the individual occurrences of that variable are independent of each other, unless otherwise specified. Also, combinations of substituents/or variables are permissible only if such combinations result in stable compounds.

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Preferred alkyl groups for use in the invention are $C_{1-6}$ alkyl groups, having from one to six atoms. Exemplary alkyl groups include methyl, ethyl, n-propyl, isopropyl, n-butyl, isobutyl, tert-butyl, pentyl, hexyl, and the like. $C_0$ alkyl means a bond.

As used herein, the term "cycloalkyl," by itself or as part of another substituent, means a saturated cyclic hydrocarbon radical having the number of carbon atoms designated (e.g., $C_{3-12}$ cycloalkyl means a cycloalkyl group having from three to twelve carbon atoms). The term cycloalkyl as used herein includes mono-, bi- and tricyclic saturated carbocycles, spirocycles, and bridged and fused ring carbocycles.

Preferred cycloalkyl groups for use in the invention are monocyclic $C_{3-8}$ cycloalkyl groups, having from three to eight carbon atoms. Exemplary monocyclic cycloalkyl groups include cyclopropyl, cyclobutyl, cyclopentyl, cyclohexyl and the like. Exemplary bridged cycloalkyl groups include adamantyl and norbornyl. Exemplary fused cycloalkyl groups include decahydronaphthalene.

As used herein, the term "aryl," by itself or as part of another substituent, means an aromatic cyclic hydrocarbon radical. Preferred aryl groups have from six to ten carbons atoms. The term "aryl" includes multiple ring systems as well as single ring systems. Preferred aryl groups for use in the invention include phenyl and naphthyl.

The term "aryl" also includes fused cyclic hydrocarbon rings which are partially aromatic (i.e., one of the fused rings is aromatic and the other is non-aromatic). An exemplary aryl group which is partially aromatic is indanyl.

The term heterocyclyl, heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocyclyl, heterocycle or heterocyclic includes heteroaryl moieties. Examples of such heterocyclic elements include, but are not limited to, azepinyl, benzodioxolyl, benzimidazolyl, benzisoxazolyl, benzofurazanyl, benzopyranyl, benzothiopyranyl, benzofuryl, benzothiazolyl, benzothienyl, benzotriazolyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyrazolopyridinyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl, and triazolyl. The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure.

When a heterocyclyl group as defined herein is substituted, the substituent may be bonded to a ring carbon atom of the heteroaryl group, or on a ring heteroatom (i.e., a nitrogen, oxygen or sulfur), which has a valence which permits substitution. Preferably, the substituent is bonded to a ring carbon atom. Similarly, when a heteroaryl group is defined as a substituent herein, the point of attachment may be at a ring carbon atom of the heteroaryl group, or on a ring heteroatom (i.e., a nitrogen, oxygen or sulfur), which has a valence which permits attachment. Preferably, the attachment is at a ring carbon atom.

As used herein, the term "halo" or "halogen" includes fluoro, chloro, bromo and iodo.

The compounds of the invention may have one or more asymmetric centers. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of the compounds of the invention. The present invention includes all stereoisomers of formulae (I) and pharmaceutically acceptable salts thereof.

It should be appreciated by any one skilled in the art that the compounds of this invention can exist in several tautomeric forms as shown below:

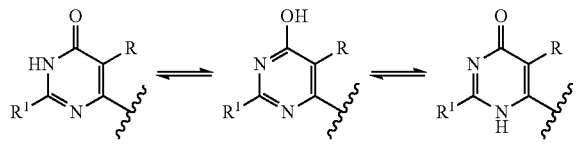

Previous researchers have studied similar compounds and found that one of these tautomers can exist as the predominant form depending on structures and conditions. See B. M. Giuliano, et al. J. Phys. Chem. A, 114, 12725-12730, 2010; B. M. Giuliano, et al. J. Phys. Chem. A, 115, 8178-8179, 2011; A. Gerega, et al. J. Phys. Chem. A, 111, 4934-4943, 2007; R. Sanchez, et al., J. Amer. Chem. Soc., 129(19), 6287-6290, 2007; C. Lopez, et al., Spectroscopy 14, 121-126, 2000; and G. M. Kheifets, et al., Russ. J. Org. Chem., 36(9), 1373-1387, 2000. For brevity and simplicity, we have represented the compounds of the present invention using Formula I and Ia and they are intended to represent all possible tautomeric forms for these compounds without regard to what actually is the predominant tautomeric form in existence for a particular compound.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of the compound bound to PDE2 enzyme, of crystalline products or crystalline intermediates that are derivatized, if necessary, with a reagent containing an asymmetric center of known absolute configuration.

If desired, racemic mixtures of the compounds may be separated so that the individual enantiomers or diastereomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer or diastereomer of a compound may be obtained by stereoselective synthesis using optically pure starting materials or reagents of known configuration by methods well known in the art.

In the compounds of the invention the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic formula I and Ia. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically enriched compounds within generic formula I and Ia can be prepared without undue experimentation by conventional techniques well known to those skilled in the art or by processes analogous to those described in the Schemes and Examples herein using appropriate isotopically enriched reagents and/or intermediates.

The term "substantially pure" means that the isolated material is at least 90% pure, and preferably 95% pure, and even more preferably 99% pure as assayed by analytical techniques known in the art.

For purposes of this specification, the following abbreviations have the indicated meanings:

Ac=acetyl
ACN=acetonitrile
AcO=acetate
BOC=t-butyloxycarbonyl
CBZ=carbobenzoxy

CDI=carbonyldiimidazole
DBU=1,8-Diazabicycloundec-7-ene
DCC=1,3-dicyclohexylcarbodiimide
DCE=1,2-dichloroethane
(dF(CF3)ppy)=2-(2,4-difluorophenyl)-5-trifluoromethyl-pyridine
DI=de-ionized
DIAD=Diisopropyl azodicarboxylate
DIBAL=diisobutyl aluminum hydride
DIPEA or DIEA=N,N-diisoproylethylamine, also known as Hunig's base
DMA=dimethylacetamide
DMAP=4-(dimethylamino)pyridine
DMF=dimethylformamide
DMP=Dess-Martin periodinane
DPPA=Diphenylphosphoryl azide
DPPP=1,3-bis(diphenylphosphino)propane
Dtbbpy=4,4'-di-tert-butyl-2,2'-dipyridyl
EDC or EDCI=1-(3-dimethylaminopropyl)-3-ethylcarbodiimide hydrochloride
EDTA=ethylenediaminetetraacetic acid, tetrasodium salt
EtOAc=ethyl acetate
FAB=fast atom bombardment
FMOC=9-fluorenylmethoxycarbonyl
HMPA=hexamethylphosphoramide
HATU=O-(7-Azabenzotriazol-1-yl)-N,N,N',N'-tetramethyluronium hexafluorophosphate
HOAt=1-Hydroxy-7-azabenzotriazole or 3H-[1,2,3]triazolo[4,5-b]pyridin-3-ol
HOBt=1-hydroxybenzotriazole
HRMS=high resolution mass spectrometry
IBCF=isobutyl chloroformate
KHMDS=potassium hexamethyldisilazane
LC-MS=Liquid chromatography-mass spectrometry
LDA=lithium diisopropylamide
LiHMDS=lithium hexamethyldisilazane
MCPBA=meta-chloroperbenzoic acid
MMPP=magnesium monoperoxyphthlate hexahydrate
Ms=methanesulfonyl=mesyl
MsO=methanefulfonate=mesylate
MTBE=Methyl t-butyl ether
NBS=N-bromosuccinimide
NMM=4-methylmorpholine
NMP=N-methylpyrrolidinone
NMR=Nuclear magnetic resonance
PCC=pyridinium chlorochromate
PDC=pyridinium dichromate
Ph=phenyl
PPTS=pyridinium p-toluene sulfonate
pTSA=p-toluene sulfonic acid
PyH.Br$_3$=pyridine hydrobromide perbromide
r.t./RT=room temperature
rac.=racemic
T3P=2,4,6-Tripropyl-1,3,5,2,4,6-trioxatriphosphinane 2,4,6-trioxide
TEA=triethylamine
TFA=trifluoroacetic acid
TfO=trifluoromethanesulfonate=triflate
THF=tetrahydrofuran
TLC=thin layer chromatography
TMSCl=trimethylsilyl chloride The compounds of the present invention may contain one or more stereogenic centers and can thus occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

All patents, patent applications and publications cited herein, whether supra or infra, are hereby incorporated by reference in their entirety and are deemed representative of the prevailing state of the art.

It will be understood that, as used herein, references to the compounds of present invention are meant to also include the pharmaceutically acceptable salts, and also salts that are not pharmaceutically acceptable when they are used as precursors to the free compounds or in other synthetic manipulations. The compounds of the present invention may be administered in the form of a pharmaceutically acceptable salt. The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, cupric, cuprous, ferric, ferrous, lithium, magnesium, manganic, manganous, potassium, sodium, zinc and the like salts. Particular embodiments include the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylamino-ethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments are citric, hydrobromic, hydrochloric, maleic, phosphoric, sulfuric, fumaric, and tartaric acids. It will be understood that, as used herein, references to the compounds of the present invention are meant to also include the pharmaceutically acceptable salts.

Exemplifying the invention are the specific compounds disclosed in the Examples and herein. The subject compounds may be useful in a method of treating a neurological or psychiatric disorder associated with PDE2 dysfunction in a patient such as a mammal in need of such inhibition comprising the administration of an effective amount of the compound. In addition to primates, especially humans, a variety of other mammals can be treated according to the method of the present invention. The subject compounds may be useful in a method of inhibiting PDE2 activity in a patient such as a mammal in need of such inhibition comprising the administration of an effective amount of the compound. The subject compounds also may be useful for treating a neurological or psychiatric disorder associated with striatal hypofunction or basal ganglia dysfunction in a mammalian patient in need thereof. In addition to primates, especially humans, a variety of other mammals can be treated according to the method of the present invention.

The present invention is directed to a compound of the present invention or a pharmaceutically acceptable salt thereof for use in medicine. The present invention is further directed to a use of a compound of the present invention or a pharmaceutically acceptable salt thereof for the manufacture of a medicament for treating a neurological or psychiatric disorder associated with PDE2 function in a mammalian patient in need thereof. The present invention is further directed to a use of a compound of the present invention or a pharmaceutically acceptable salt thereof for the manufacture of a medicament for treating a neurological or psychiatric disorder associated with striatal hypofunction or basal ganglia dysfunction in a mammalian patient in need thereof.

"Treating" or "treatment of" a disease state includes: 1) inhibiting the disease state, i.e., arresting the development of the disease state or its clinical symptoms; 2) or relieving the disease state, i.e., causing temporary or permanent regression of the disease state or its clinical symptoms.

The subject treated in the present methods is generally a mammal, in particular, a human being, male or female, in whom therapy is desired. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with such disorders with an effective amount of the compound of the present invention.

Applicants propose that inhibitors of PDE2, including PDE2A, will provide therapeutic benefit to those individuals suffering from psychiatric and cognitive disorders. The unique and exclusive distribution of PDE2A in the medium spiny projection neurons of the striatum, which form the principle site for cortical and dopaminergic input within basal ganglia, suggests that it may be possible and desirable to identify inhibitors of PDE2 to enhance cellular signaling. Without wishing to be bound by any theory, applicants believe that inhibition of PDE2A in the striatum will result in increased cAMP/cGMP signaling and striatal output, which has the potential to restore behavioral inhibition that is impaired in cognitive disease such as schizophrenia. Regulation and integration of glutamatergic and dopaminergic inputs will enhance cognitive behavior, while suppressing or reducing unwanted behavior. Thus, in one embodiment, compounds of the invention provide a method for treating or ameliorating diseases or conditions in which striatal hypofunction is a prominent feature or ones in which basal ganglia dysfunction plays a role, such as, Parkinson's disease, Parkinson's disease dementia (PDD), Huntington's disease, schizophrenia, obsessive-compulsive disorders, addiction and psychosis. Other conditions for which the inhibitors described herein may have a desirable and useful effect include those requiring a reduction in activity and reduced response to psychomotor stimulants or where it would be desirable to reduce conditional avoidance responses, which is often predictive of clinical antipsychotic activity.

In another embodiment the compounds of this invention there is provided a method for treating or ameliorating diseases or conditions in neuronal development, learning, and memory, prolactin and aldosterone secretion, bone cell differentiation, growth, and bone resorption, immunological response, vascular angiogenesis, inflammatory cell transit, cardiac contraction, platelet aggregation, female sexual arousal disorder, and hypoxic pulmonary vasoconstriction.

As used herein, the term "selective PDE2 inhibitor" refers to an organic molecule that effectively inhibits an enzyme from the PDE2 family to a greater extent than enzymes from the PDE 1, and 3-11 families. In one embodiment, a selective PDE2 inhibitor is an organic molecule having a Ki for inhibition of PDE2 that is less than or about one-tenth that for a substance that is an inhibitor for another PDE enzyme. In other words, the organic molecule inhibits PDE2 activity to the same degree at a concentration of about one-tenth or less than the concentration required for any other PDE enzyme. Preferably, a selective PDE2 inhibitor is an organic molecule, having a Ki for inhibition of PDE2 that is less than or about one-hundredth that for a substance that is an inhibitor for another PDE enzyme. In other words, the organic molecule inhibits PDE2 activity to the same degree at a concentration of about one-hundredth or less than the concentration required for any other PDE enzyme. Preferably, a selective PDE2 inhibitor is an organic molecule, having a Ki for inhibition of PDE2 that is less than or about five-hundredth that for a substance that is an inhibitor for another PDE enzyme. In other words, the organic molecule inhibits PDE2 activity to the same degree at a concentration of about five-hundredth or less than the concentration required for any other PDE enzyme. A "selective PDE2 inhibitor" can be identified, for example, by comparing the ability of an organic molecule to inhibit PDE2 activity to its ability to inhibit PDE enzymes from the other PDE families. For example, an organic molecule may be assayed for its ability to inhibit PDE2 activity, as well as PDE1A, PDE1B, PDE1C, PDE3A, PDE3B, PDE4A, PDE4B, PDE4C, PDE4D, PDE5A, PDE6A, PDE6B, PDE6C, PDE7A, PDE7B, PDE8A, PDE8B, PDE9A, PDE10 and/or PDE11A.

Phosphodiesterase enzymes including PDE2 have been implicated in a wide range of biological functions. This has suggested a potential role for these enzymes in a variety of disease processes in humans or other species. The compounds of the present invention may have utility in treating a variety of neurological and psychiatric disorders.

In a specific embodiment, compounds of the present invention provide a method for treating schizophrenia or psychosis comprising administering to a patient in need thereof an effective amount of a compound of the present invention. The Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorders. As used herein, the term "schizophrenia or psychosis" includes the diagnosis and classification of these mental disorders as described in DSM-IV-TR and the term is intended to include similar disorders described in other sources. Disorders and conditions encompassed herein include, but are not limited to, conditions or diseases such as schizophrenia or psychosis, including schizophrenia (paranoid, disorganized, catatonic, undifferentiated, or residual type), schizophreniform disorder, schizoaffective disorder, for example of the delusional type or the depressive type, delusional disorder, psychotic disorder, brief psychotic disorder, shared psychotic disorder, psychotic disorder due to a general medical condition and substance-induced or drug-induced (for example psychosis induced by alcohol, amphetamine, cannabis, cocaine, hallucinogens, inhalants, opioids, phencyclidine, ketamine and other dissociative anaesthetics, and other psychostimulants), psychosispsychotic disorder, psychosis associated with affective disorders, brief reactive psychosis, schizoaffective psychosis, "schizophrenia-spectrum" disorders such as schizoid or schizotypal personality disorders, personality disorder of the paranoid type, personality disorder of the schizoid type, illness associated with psychosis (such as major depression, manic depressive (bipolar) disorder, Alzheimer's disease and post-traumatic stress syndrome), including both the positive and the negative symptoms of schizophrenia and other psychoses.

In another specific embodiment, the compounds of the present invention provide a method for treating cognitive disorders comprising administering to a patient in need thereof an effective amount of a compound of the present invention. The DSM-IV-TR also provides a diagnostic tool that includes cognitive disorders including dementia, delirium, amnestic disorders and age-related cognitive decline. As used herein, the term "cognitive disorders" includes the diagnosis and classification of these disorders as described in DSM-IV-TR and the term is intended to include similar disorders described in other sources. Disorders and conditions encompassed herein include, but are not limited to, disorders that comprise as a symptom a deficiency in attention and/or cognition, such as dementia (associated with Alzheimer's disease, ischemia, multi-infarct dementia, trauma, intracranial tumors, cerebral trauma, vascular problems or stroke, alcoholic dementia or other drug-related dementia, AIDS, HIV disease, Parkinson's disease, Parkinson's disease dementia (PDD), Huntington's disease, Pick's disease, Creutzfeldt Jacob disease, perinatal hypoxia, other general medical conditions or substance abuse), Alzheimer's disease, multi-infarct dementia, AIDS-related dementia, and Fronto temporal dementia, delirium, amnestic disorders or age related cognitive decline.

In another specific embodiment, compounds of the present invention provide a method for treating anxiety disorders comprising administering to a patient in need thereof an effective amount of a compound of the present invention. The DSM-IV-TR also provides a diagnostic tool that includes anxiety disorders as generalized anxiety disorder, obsessive-compulsive disorder and panic attack. As used herein, the term "anxiety disorders" includes the diagnosis and classification of these mental disorders as described in DSM-IV-TR and the term is intended to include similar disorders described in other sources. Disorders and conditions encompassed herein include, but are not limited to, anxiety disorders such as, acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition.

In another specific embodiment, compounds of the present invention provide a method for treating substance-related disorders and addictive behaviors comprising administering to a patient in need thereof an effective amount of a compound of the present invention. The DSM-IV-TR also provides a diagnostic tool that includes persisting dementia, persisting amnestic disorder, psychotic disorder or anxiety disorder induced by substance abuse, and tolerance of, dependence on or withdrawal from substances of abuse. As used herein, the term "substance-related disorders and addictive behaviors" includes the diagnosis and classification of these mental disorders as described in DSM-IV-TR and the term is intended to include similar disorders described in other sources. Disorders and conditions encompassed herein include, but are not limited to, substance-related disorders and addictive behaviors, such as substance-induced delirium, persisting dementia, persisting amnestic disorder, psychotic disorder or anxiety disorder, drug addiction, tolerance, and dependence or withdrawal from substances including alcohol, amphetamines, cannabis, cocaine, hallucinogens, inhalants, nicotine, opioids, phencyclidine, sedatives, hypnotics or anxiolytics.

In another specific embodiment, compounds of the present invention provide a method for treating obesity or eating disorders associated with excessive food intake, and complications associated therewith, comprising administering to a patient in need thereof an effective amount of a compound of the present invention. At present, obesity is included in the tenth edition of the International Classification of Diseases and Related Health Problems (ICD-10) (1992 World Health Organization) as a general medical condition. The DSM-IV-TR also provides a diagnostic tool that includes obesity in the presence of psychological factors affecting medical condition. As used herein, the term "obesity or eating disorders associated with excessive food intake" includes the diagnosis and classification of these medical conditions and disorders described in ICD-2 and DSM-IV-TR and the term is intended to include similar disorders described in other sources. Disorders and conditions encompassed herein include, but are not limited to, obesity, bulimia nervosa and compulsive eating disorders.

In another specific embodiment, compounds of the present invention provide a method for treating mood and depressive disorders comprising administering to a patient in need thereof an effective amount of a compound of the present invention. As used herein, the term "mood and depressive disorders" includes the diagnosis and classification of these medical conditions and disorders described in the DSM-IV-TR and the term is intended to include similar disorders described in other sources. Disorders and conditions encompassed herein include, but are not limited to, bipolar disorders, mood disorders including depressive disorders, major depressive episode of the mild, moderate or severe type, a manic or mixed mood episode, a hypomanic mood episode, a depressive episode with atypical features, a depressive episode with melancholic features, a depressive episode with catatonic features, a mood episode with post-partum onset, post-stroke depression; major depressive disorder, dysthymic disorder, minor depressive disorder, premenstrual dysphoric disorder, post-psychotic depressive disorder of schizophrenia, a major depressive disorder superimposed on a psychotic disorder such as delusional disorder or schizophrenia, a bipolar disorder, for example, bipolar I disorder, bipolar II disorder, cyclothymic disorder, depression including unipolar depression, seasonal depression and post-partum depression, premenstrual syndrome (PMS) and premenstrual dysphoric disorder, mood disorders due to a general medical condition, and substance-induced mood disorders.

In another specific embodiment, compounds of the present invention provide a method for treating pain comprising administering to a patient in need thereof an effective amount of a compound of the present invention. Particular pain embodiments are bone and joint pain (osteoarthritis), repetitive motion pain, dental pain, cancer pain, myofascial pain (muscular injury, fibromyalgia), perioperative pain (general surgery, gynecological), chronic pain and neuropathic pain.

In other specific embodiments, compounds of the invention provide methods for treating other types of cognitive, learning and mental related disorders including, but not limited to, learning disorders, such as a reading disorder, a mathematics disorder, or a disorder of written expression, attention-deficit/hyperactivity disorder, age-related cognitive decline, pervasive developmental disorder including autistic disorder, attention disorders such as attention-deficit hyperactivity disorder (ADHD) and conduct disorder; an NMDA receptor-related disorder, such as autism, depression, benign forgetfulness, childhood learning disorders and closed head injury; a neurodegenerative disorder or condition, such as neurodegeneration associated with cerebral trauma, stroke, cerebral infarct, epileptic seizure, neurotoxin poisoning, or hypoglycemia-induced neurodegeneration; multi-system atrophy; movement disorders, such as akinesias and akinetic-rigid syndromes (including, Parkinson's disease, Parkinson's disease dementia (PDD), drug-induced parkinsonism, post-encephalitic parkinsonism, progressive supranuclear palsy, multiple system atrophy, corticobasal degeneration, parkinsonism-ALS dementia complex and basal ganglia calcification), medication-induced parkinsonism (such as, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Huntington's disease, dyskinesia associated with dopamine agonist therapy, Gilles de la Tourette's syndrome, epilepsy, muscular spasms and disorders associated with muscular spasticity or weakness including tremors; dyskinesias, including tremor (such as, rest tremor, postural tremor, intention tremor and essential tremor), restless leg syndrome, chorea (such as Sydenham's chorea, Huntington's disease, benign hereditary chorea, neuroacanthocytosis, symptomatic chorea, drug-induced chorea and hemiballism), myoclonus (including, generalised myoclonus and focal myoclonus), tics (including, simple tics, complex tics and symptomatic tics), dystonia (including, generalised, iodiopathic, drug-induced, symptomatic, paroxymal, and focal (such as blepharospasm, oromandibular, spasmodic, spasmodic torticollis, axial dystonia, hemiplegic and dystonic writer's cramp)); urinary incontinence; neuronal damage (including ocular damage, retinopathy or macular degeneration of the eye, tinnitus, hearing impairment and loss, and brain edema); emesis; and sleep disorders, including insomnia and narcolepsy.

Of the disorders above, the treatment of schizophrenia, bipolar disorder, depression, including unipolar depression, seasonal depression and post-partum depression, premenstrual syndrome (PMS) and premenstrual dysphoric disorder, learning disorders, pervasive developmental disorders, including autistic disorder, attention disorders including Attention-Deficit/Hyperactivity Disorder, autism, tic disorders including Tourette's disorder, anxiety disorders including phobia and post-traumatic stress disorder, cognitive disorders associated with dementia, AIDS dementia, Alzheimer's, Parkinson's, Huntington's disease, spasticity, myoclonus, muscle spasm, tinnitus and hearing impairment and loss are of particular importance.

Angiogenesis is the physiological process through which new blood vessels form, and agents that inhibit this process have been shown to be effective treatments for some cancers. As initiation of angiogenesis involves migration and proliferation of vascular endothelial cells, and agents that elevate cAMP inhibit these processes, PDE2 inhibition may have utility as a treatment for cancer. See Savai, et al, *Targeting cancer with phosphodiesterase inhibitors*, Expert Opin. Investig. Drugs (2010) 19(1):117-131. PDE2 has been shown to be expressed in human vascular endothelial cells (VECs) and inhibition of PDE2 by treatment with selective inhibitors inhibited VEGF promoted migration of VECs. See Netherton and Maurice, *Vascular Endothelial Cell Cyclic Nucleotide Phosphodiesterases and Regulated Cell Migration: Implications in Angiogenesis*, Mol Pharmacol (2005) 67:263-272 and Favot, et al, *VEGF-induced HUVEC migration and proliferation are decreased by PDE2 and PDE4 inhibitors*. Thromb Haemost (2003) 90:334-343. Reduction of PDE2 activity with either small molecule inhibitors or PDE2A siRNA suppressed cell growth and invasion in a human malignant melanoma PMP cell line. See Hiramoto, et al, *Role of phosphodiesterase 2 in growth and invasion of human malignant melanoma cells*, Cellular Signalling (2014), 26:1807-1817. Reduction of PDE2 activity with a small molecule inhibitor attenuated tumor formation in a mouse model of ultraviolet light B-induced tumorigenesis. See Bernard, et al, *PDE2 is a Novel Target for Attenuating Tumor Formation in a Mouse Model of UVB Induced Skin Carcinogenesis*, PLoS ONE (2014), 9(10):e109862. Thus, in another specific embodiment, compounds of the invention provide methods for treating, preventing, controlling, and/or reducing, attenuating cancers, such as malignant melanomas, skin cancer, and the like.

The subject compounds may be further useful in a method for the prevention, treatment, control, amelioration, or reduction of risk of the diseases, disorders and conditions noted herein. The subject compounds are further useful in a method for the prevention, treatment, control, amelioration, or reduction of risk of the aforementioned diseases, disorders and conditions in combination with other agents. The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefore, contemporaneously or sequentially with a compound of the present invention. When a compound of the present invention is used contemporaneously with one or more other drugs, a pharmaceutical composition in unit dosage form containing such other drugs and the compound of the present invention may be desirable. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. Accordingly, the pharmaceutical compositions of the present invention include those that also contain one or more other active ingredients, in addition to a compound of the present invention. The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

Accordingly, the subject compounds may be used alone or in combination with other agents which are known to be beneficial in the subject indications or other drugs that affect receptors or enzymes that either increase the efficacy, safety, convenience, or reduce unwanted side effects or toxicity of the compounds of the present invention. The subject compound and the other agent may be co-administered, either in concomitant therapy or in a fixed combination.

In one embodiment, the subject compound may be employed in combination with anti-Alzheimer's agents, AChEis (Aricept (donepezil)) and NMDA blocker Namenda (memantine), beta-secretase inhibitors, gamma-secretase inhibitors, HMG-CoA reductase inhibitors, NSAID's including ibuprofen, vitamin E, and anti-amyloid antibodies.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, atypical antipsychotics, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MAO-B inhibitors, antioxidants, Ata adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisulpride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In another embodiment, the subject compound may be employed in combination with an antidepressant or antianxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-HT$_{1A}$ agonists or antagonists, especially 5-HT$_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans. The terms "administration of" and or "administering a" compound should be understood to mean providing a compound of the invention or a prodrug of a compound of the invention to the individual in need of treatment.

The term "composition" as used herein is intended to encompass a product comprising specified ingredients in predetermined amounts or proportions, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by mixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredients are mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions, oily suspensions, dispersible powders or granules, oil-in-water emulsions, and sterile injectable aqueous or oleagenous suspension may be prepared by standard methods known in the art. By "pharmaceutically acceptable" it is meant the carrier, diluent or excipient must be compatible with the other ingredients of the formulation and not deleterious to the recipient thereof.

The subject compounds are further useful in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.001 to 10 mg/kg of body weight daily are administered to the patient, e.g., humans and elderly humans. The dosage range will generally be about 0.5 mg to 1.0 g per patient per day which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

Several methods, schemes, and examples for preparing representative compounds of this invention are illustrated below and can be found in further detail in U.S. Pat. No. 7,144,913, which is incorporated by reference herein in its entirety. Starting materials and the requisite intermediates are in some cases commercially available, or can be prepared according to literature procedures or as illustrated herein. The compounds of this invention may be prepared by employing reactions as shown in the following schemes, in addition to other standard manipulations that are known in the literature or exemplified in the experimental procedures. Substituent numbering as shown in the schemes does not necessarily correlate to that used in the claims and often, for clarity, a single substituent is shown attached to the compound where multiple substituents are allowed under the definitions hereinabove. Reactions used to generate the compounds of this invention are prepared by employing conditions as shown in the schemes and examples herein, as well as using other standard manipulations such as ester hydrolysis, cleavage of protecting groups, etc., as may be known in the literature or exemplified in the experimental procedures. Starting materials are made according to procedures known in the art or as illustrated herein.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood.

The representative examples of the compounds of the invention are illustrated in the following non-limiting schemes and Examples.

General

Starting materials used were obtained from commercial sources or prepared in other examples, unless otherwisely noted.
The progress of reactions was often monitored by TLC or LC-MS. The LC-MS was recorded using one of the following methods.
Method A XBridge Shield RP18: 2.5×50 mm, 3.5 um, 1.0 uL injection, 1.00 mL/min flow rate, 90-900 amu scan range, 190-400 nm UV range, 10-95% (over 2.2 min) gradient with MeCN and water (0.04% aq. $NH_3$), hold 1 min; 3.6 minute total run time.
Method B: Supelco Ascentis Express C18, 3×50 mm, 2.7 um column. 2.0 uL injection, 1.25 ml/min flow rate, 170-900 amu scan range, 200-400 nm UV range, 10-99% (over 2.0 min) gradient with MeCN (0.05% TFA) and water (0.05%); 3 minute total run time.
Method C: Supelco Ascentis Express C18, 3×100 mm, 2.7 um column. 2.0 uL injection, 1.00 ml/min flow rate, 170-900 amu scan range, 200-400 nm UV range, 10-99% (over 4.0 min) gradient with MeCN (0.05% TFA) and water (0.05%); 5 minute total run time.
Method D: Waters Acquity UPLC, HSS C18 1.8 um, 2.1×50 mm, MeCN and water with 0.1% trifluoroacetic acid, 1 mL/min flow rate, gradient 5%-100% MeCN over 1.4 min.
Method E: Waters Acquity UPLC, HSS C18 1.8 um, 2.1×50 mm, MeCN and water with 0.1% formic acid, 1 mL/min flow rate, gradient 5%-100% MeCN over 1.4 min.
Method F: Shimadzu: 3.0×50 mm, 2.2 um, 1.0 uL injection, 1.00 mL/min flow rate, 90-900 amu scan range, 190-400 nm UV range, 5-100% (over 2.2 min) gradient with MeCN (0.05% TFA) and water (0.05% TFA), hold 1 min; 3.6 minute total run time.
Method G: Titan C18: 2.1×50 mm, 1.9 um, 1.0 uL injection, 0.80 mL/min flow rate, 90-900 amu scan range, 190-400 nm UV range, 5-100% (over 2.1 min) gradient with MeCN (0.05% TFA) and water (0.05% TFA), hold 0.5 min; 3.0 minute total run time.
Method H: ZORBAX Eclipse Plus C18: 3.0×50 mm, 1.8 um, 1.0 uL injection, 1.00 mL/min flow rate, 90-900 amu scan range, 190-400 nm UV range, 5-100% (over 2.1 min) gradient with MeCN (0.1% FA) and water (0.1% FA), hold 0.5 min; 3.0 minute total run time.
Method I: XBridge C18: 4.6×50 mm, 3.5 um, 1.0 uL injection, 1.50 mL/min flow rate, 90-900 amu scan range, 190-400 nm UV range, 10-95% (over 2.2 min) gradient with MeCN and water (5 μM $NH_4HCO_3$), hold 1 min; 3.6 minute total run time.

NMR was recorded at room temperature unless noted otherwise on Varian Inova 400 or 500 MHz spectrometers with the solvent peak used as the reference or on Bruker 300 or 400 MHz spectrometers with the TMS peak used as internal reference.

The methods used for the preparation of the compounds of this invention are illustrated by the following schemes. Unless specified otherwise, all starting materials used are commercially available.

Scheme 1.

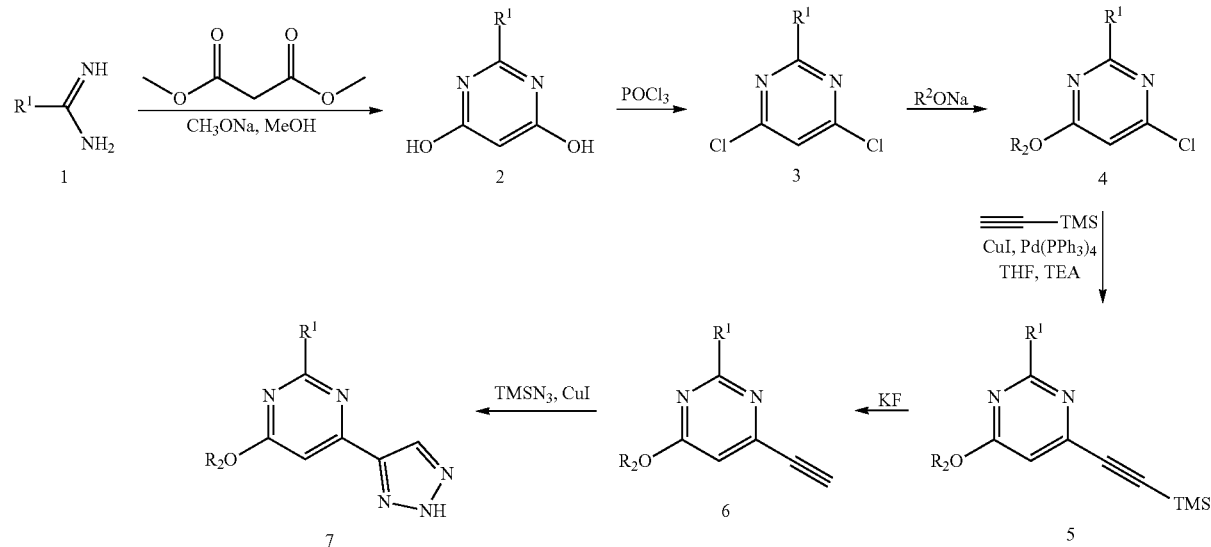

Scheme 1 illustrates a synthetic sequence for the preparation of ethynylpyrimidine derivatives such as 6 and pyrimidinyltriazoles such as 7 from amidines. Amidine 1 is condensed with β-diester to afford diolpyrimidine 2. The diolpyrimidine 2 is converted to dichloropyrimidine 3 using POCl₃. The dichloropyrimidine 3 is substituted by an alcohol to afford monochloropyrimidine 4, which is converted to ethynylpyrimidine 5 via a Sonogashira reaction. The TMS group of 5 is removed using fluoride source such as potassium fluoride to afford intermediate 6, which is subsequently converted to triazole 7 through a cycloaddition reaction with TMS-azide.

dines such as 8. Alkynylpyrimidines such as 11 are prepared via a palladium-catalyzed cross-coupling reaction of chloropyrimidines such as 8 with either an alkynyl boronate ester such as 9 or a terminal alkyne such as 10.

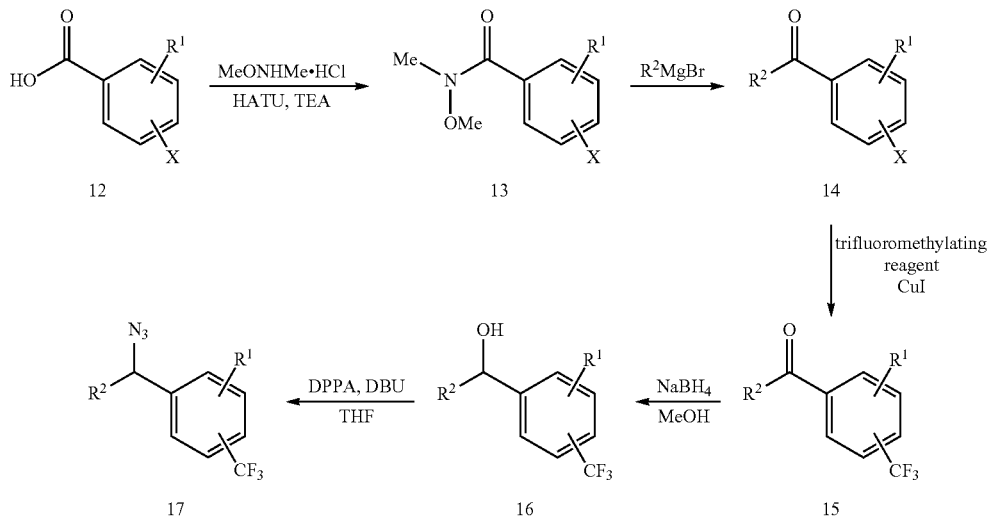

Scheme 3.

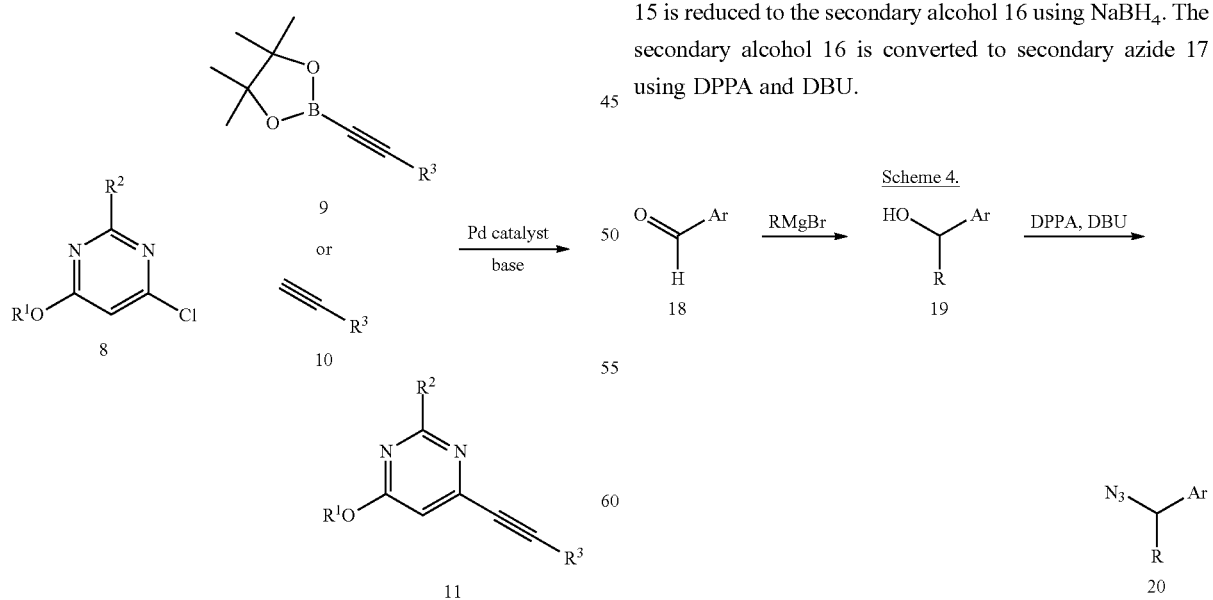

Scheme 2.

Scheme 3 illustrates a synthetic sequence for the preparation of benzylic azides such as 17 from benzoic acid derivatives such as 12. The coupling of arylcarboxylic acid 12 and N,O-dimethylhydroxylamine hydrochloride gives the Weinreb amide 13. Ketone 14 is obtained by addition of a Grignard reagent R²MgBr to Weinreb amide 13. The aryl halide 14 can be transformed to trifluoromethyl aromatic compound 15 using a trifluoromethylating reagent. Ketone 15 is reduced to the secondary alcohol 16 using NaBH₄. The secondary alcohol 16 is converted to secondary azide 17 using DPPA and DBU.

Scheme 4.

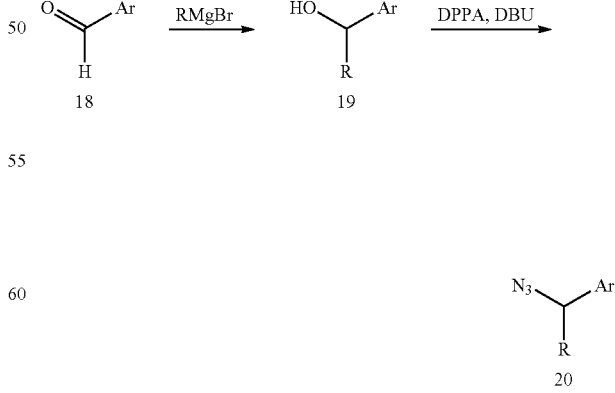

Scheme 2 illustrates a synthetic sequence for the synthesis of alkynylpyrimidines such as 11 from chloroalkoxypyrimi- Scheme 4 illustrates a synthetic sequence for the preparation of benzylic azides such as 20 from aldehyde derivatives such as 18. Addition of a Grignard reagent RMgBr to aldehyde 18 gives secondary alcohol 19. Secondary alcohol 19 is converted to the secondary azide 20 using DPPA and DBU.

Scheme 5.

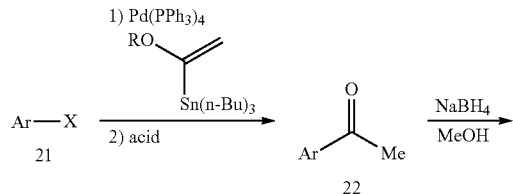

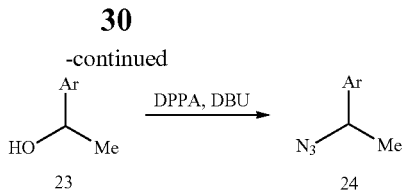

Scheme 5 illustrates a synthetic sequence for the preparation of azides such as 24 from aryl halides such as 21. Aryl halide 21 is converted to ketone 22 using a Stille reaction followed by hydrolysis. The ketone 22 is reduced to alcohol 23, which is then converted to azide 24 using DPPA and DBU.

Scheme 6.

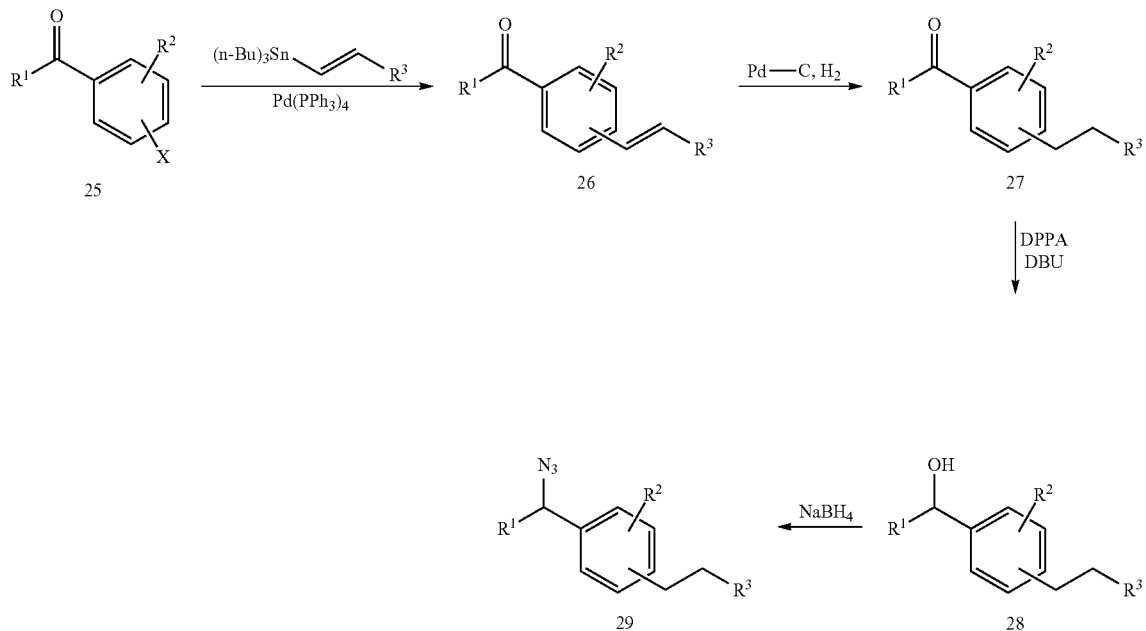

Scheme 6 illustrates a synthetic sequence for the syntheses of azides such as 29 from ketones such as 25. Aryl halide 25 is converted to arylalkene 26 using a Stille reaction. Alkene 26 is reduced to alkane 27. Arylketone 27 is reduced to alcohol 28, which is subsequently converted to azide 29 using DPPA and DBU.

Scheme 7.

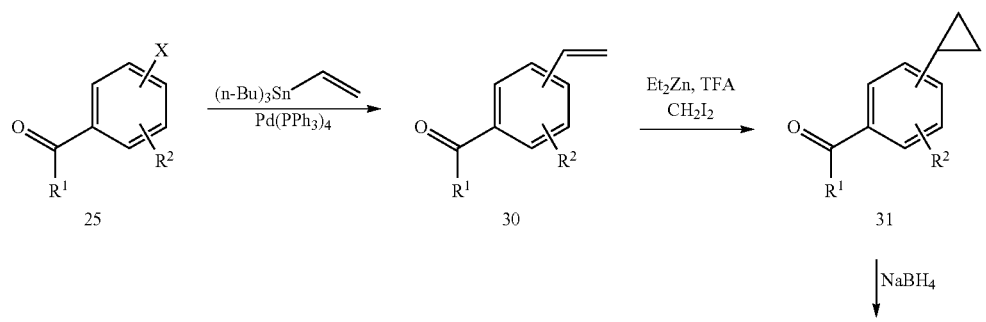

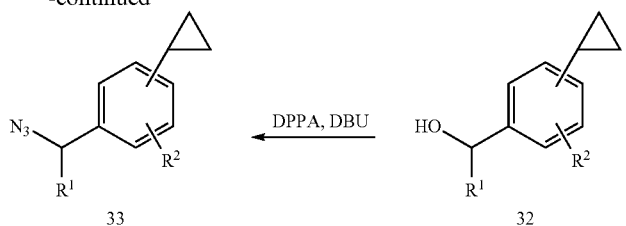

Scheme 7 illustrates a synthetic sequence for the preparation of benzylic azides such as 33 from ketones such as 25. 25 is converted to olefin 30 via a Stille coupling with a vinyl stannane. Subsequent cyclopropanation provides ketone 31, which may be converted to the azide 33 via sequential reduction and azidization with DPPA and DBU.

Scheme 8.

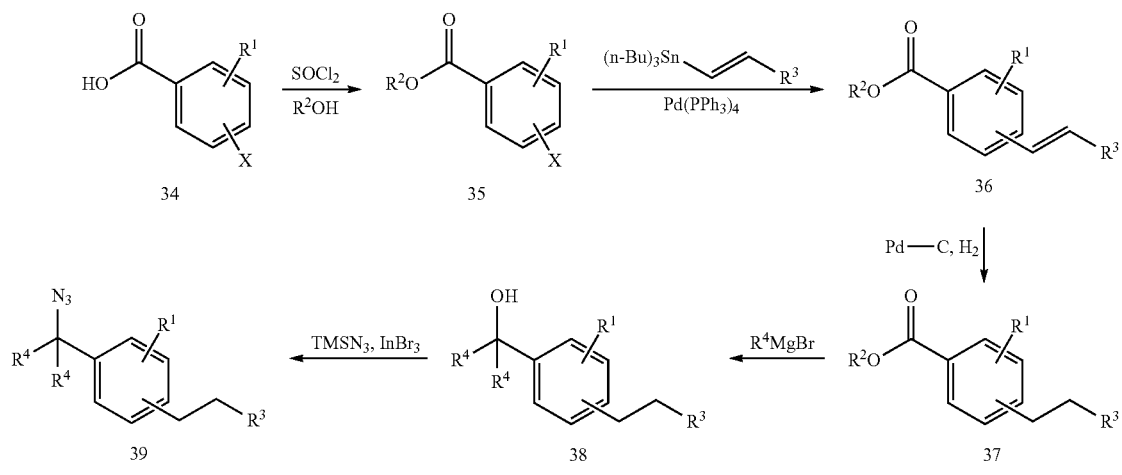

Scheme 8 illustrates a synthetic sequence for the synthesis of azides such as 39 from benzoic acids such as 34. Arylcarboxylic acid 34 is converted to ester 35 under acidic conditions. Aryl halide 35 is converted to arylalkene 36 via a Stille reaction. The alkene 36 is reduced to alkane 37 with a palladium catalyst under an atmosphere of hydrogen. Arylcarboxylate 37 is converted to tertiary alcohol 38 via a nucleophilic addition using a Grignard reagent R⁴MgBr. Alcohol 38 is converted to azide 39 using TMS-azide in the presence of InBr₃.

Scheme 9.

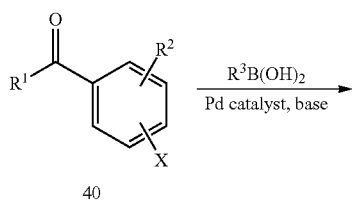

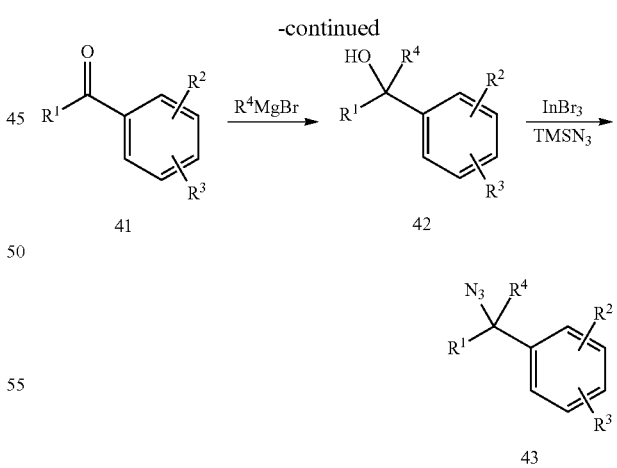

Scheme 9 illustrates a synthetic sequence for the syntheses of azides such as 43 from ketones such as 39. Aryl halide 39 is converted to substituted arylketone 40 via a Suzuki reaction. Addition of a Grignard reagent such as R⁴MgBr to arylketone 41 forms tertiary alcohol 42, which is subsequently converted to azide 43 using TMS-azide in the presence of InBr₃.

Scheme 10.

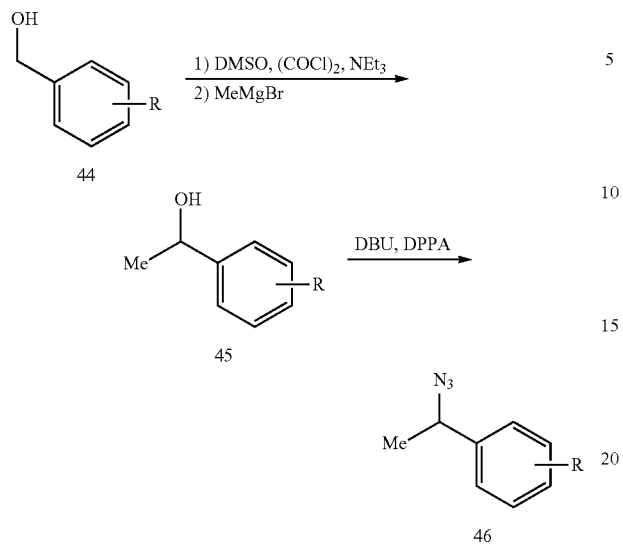

Scheme 10 illustrates a synthetic sequence for the synthesis of azides such as 46 from alcohols such as 44. Benzylic alcohol 44 is oxidized to the aldehyde via a Swern reaction. The resulting aldehyde is then treated with methylmagnesium bromide to provide secondary benzylic alcohol 45, which is subsequently converted to azide 46 with DBU and DPPA.

Scheme 11.

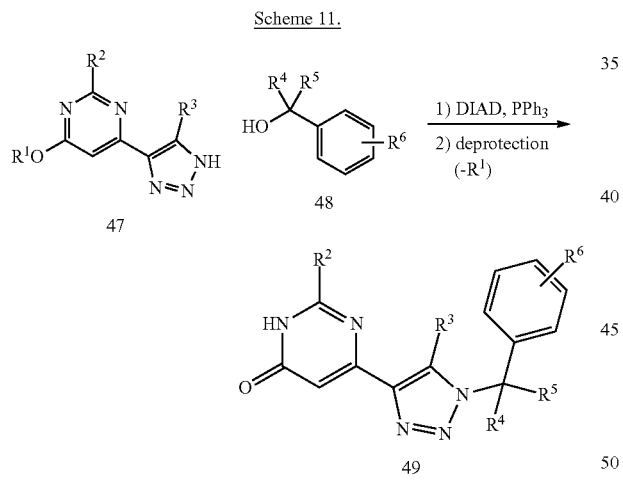

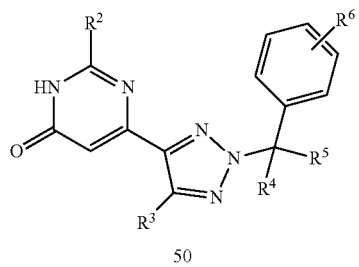

Scheme 11 illustrates a synthetic sequence for the preparation of triazolylpyrimidinone derivatives such as 49 and 50 from precursors such as N—H triazole 47 and benzylic alcohol 48 via a Mitsunobu reaction.

Scheme 12.

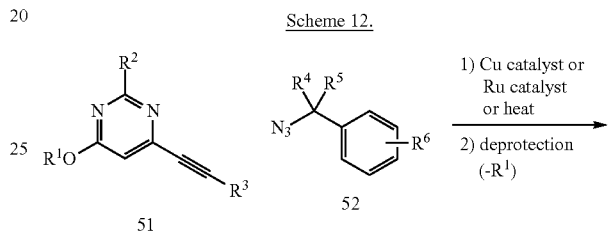

Alternatively, as illustrated in Scheme 12, triazole derivatives such as 49 are prepared via a metal-catalyzed cycloaddition of alkynes such as 51 and azides such as 52 followed by deprotection.

Scheme 13.

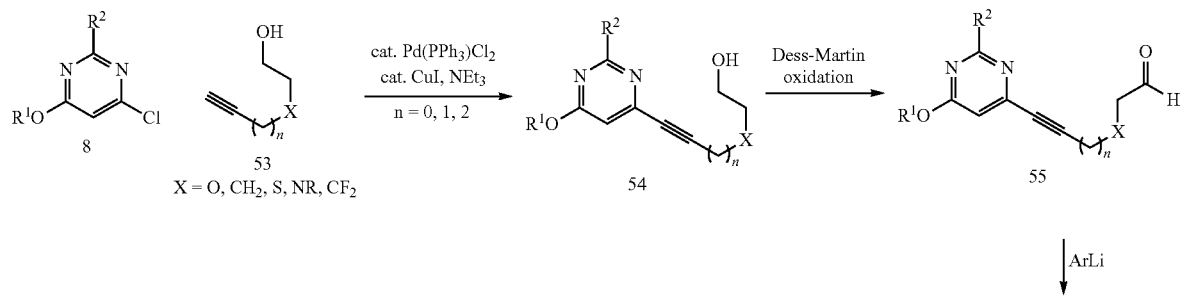

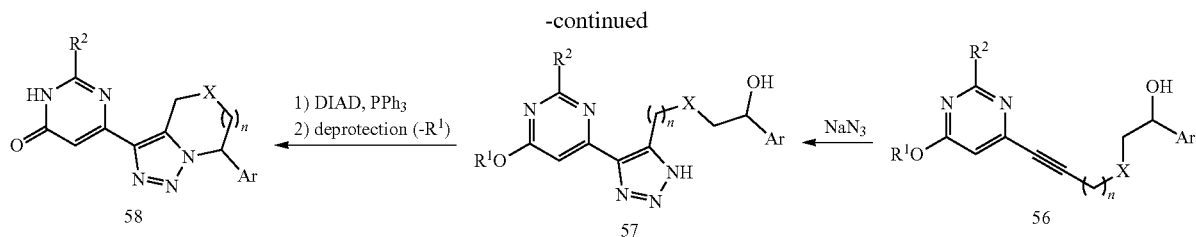

Scheme 13 illustrates a 6-step synthetic sequence for the synthesis of triazole derivatives such as 58 from chloro pyrimidines such as 8 and terminal alkynes such as 53. Palladium-catalyzed cross-coupling of 8 and 53 yields alkynylpyrimidine 54. Alcohol intermediate 54 is oxidized to aldehyde 55 which is then derivatized with aryllithium reagents to furnish intermediate 56. Cycloaddition of compounds like 56 with sodium azide affords triazolyl alcohols such as 57 which can be transformed into bicyclic triazole derivatives 58 via a Mitsunobu reaction followed by deprotection.

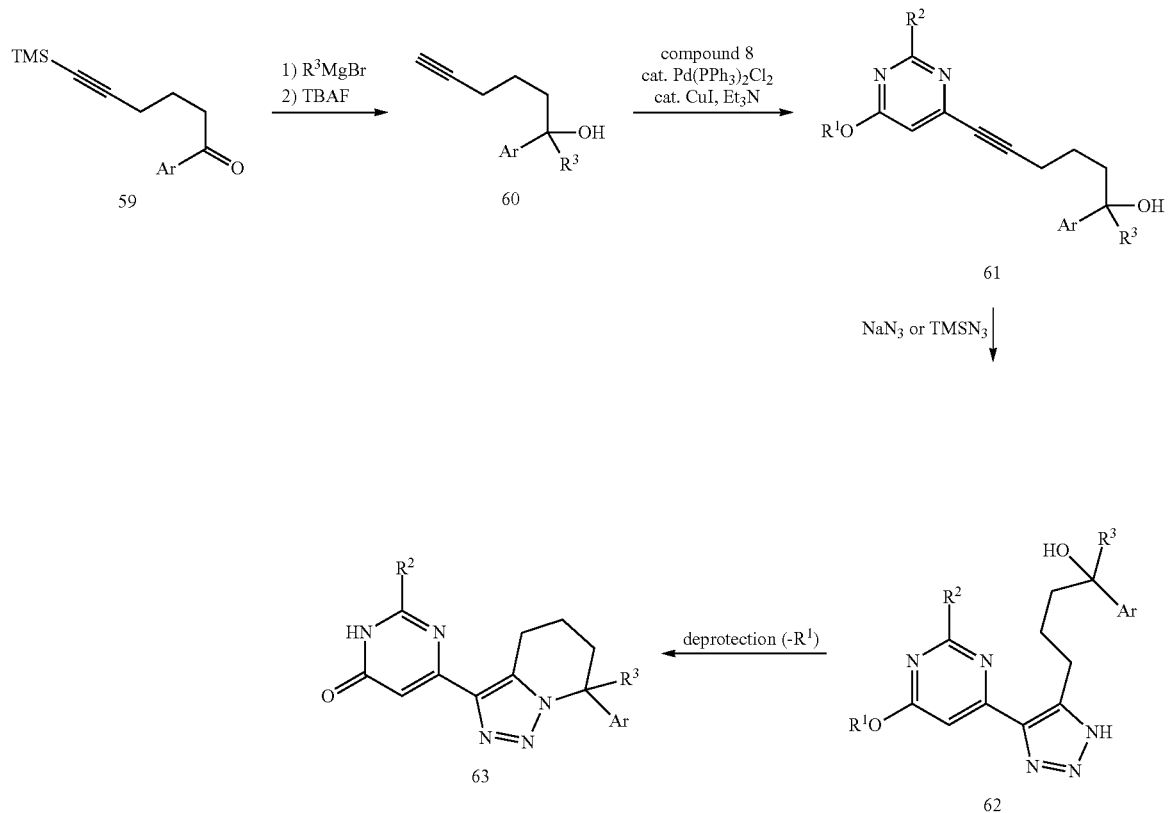

Scheme 14 illustrates a synthetic sequence for the preparation of triazole derivatives such as 63 from ketones such as 59. Grignard addition of $R^3$MgBr to ketone 59 provides tertiary alcohol intermediate 60. Palladium-catalyzed cross coupling of 60 with chloropyrimidine 8 affords the alkynylpyrimidine 61 which is converted to triazole intermediate 62 through cycloaddition with sodium azide. Deprotection of 62 affords triazole derivatives 63.

Scheme 15.

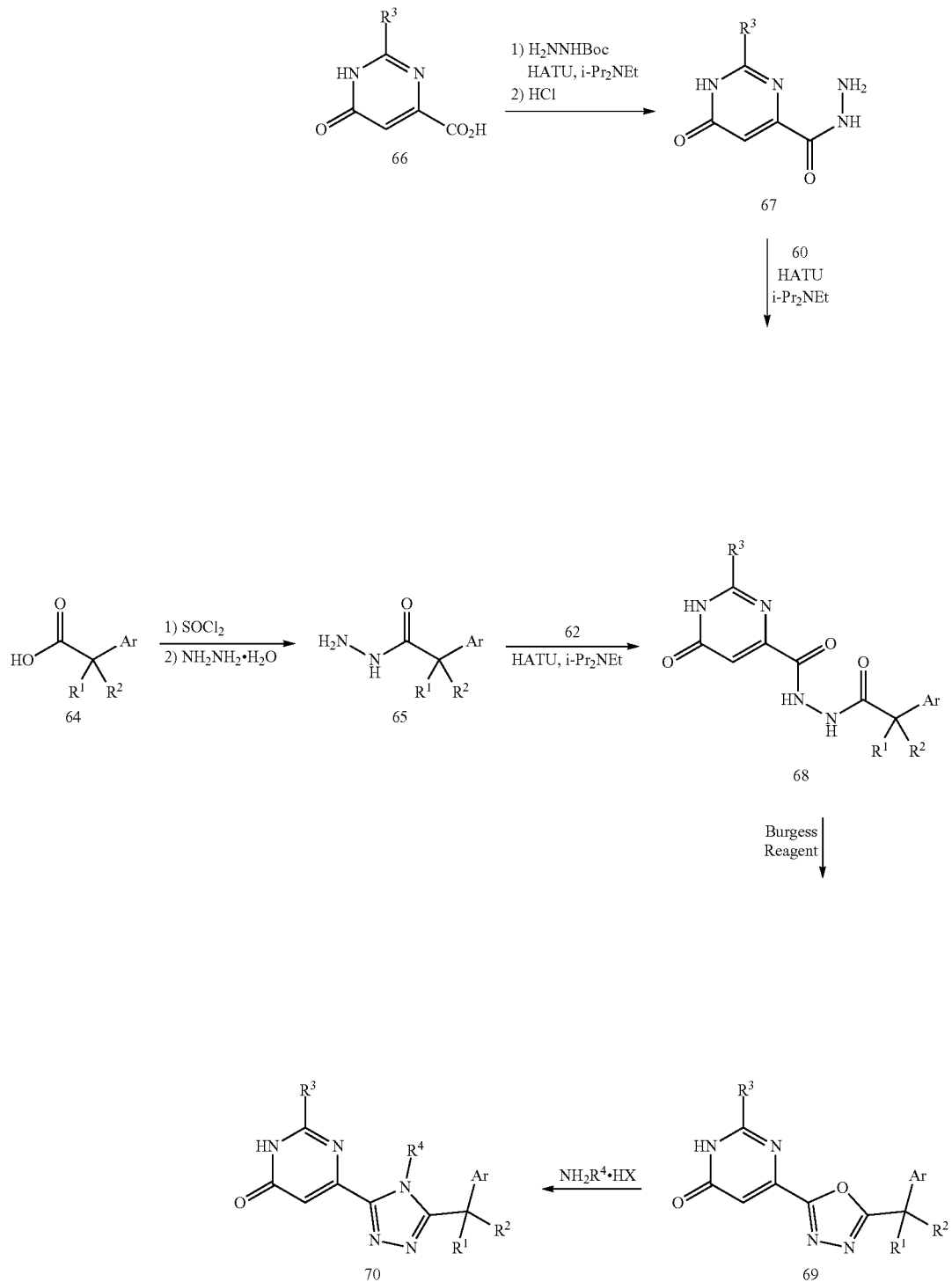

Scheme 15 illustrates a synthetic sequence for the preparation of 1,2,4-triazole derivatives such as 70 from carboxylic acids such as 64 and 66. Transformation of 64 to hydrazide 65 is accomplished via activation with $SOCl_2$ followed by addition of hydrazine. Coupling of hydrazide 65 with pyrimidine acid 66 provides intermediate 68 which can be dehydrated with Burgess reagent to provide oxadiazole intermediate 69. Condensation of 69 with various amines provides triazole derivatives 70. Alternatively, pyrimidinone hydrazide 67, derived from coupling of 66 with Boc-hydrazide followed by deprotection, may be converted to the intermediate 69 which can be transformed into triazoles such as 70 as described above.

Scheme 16.

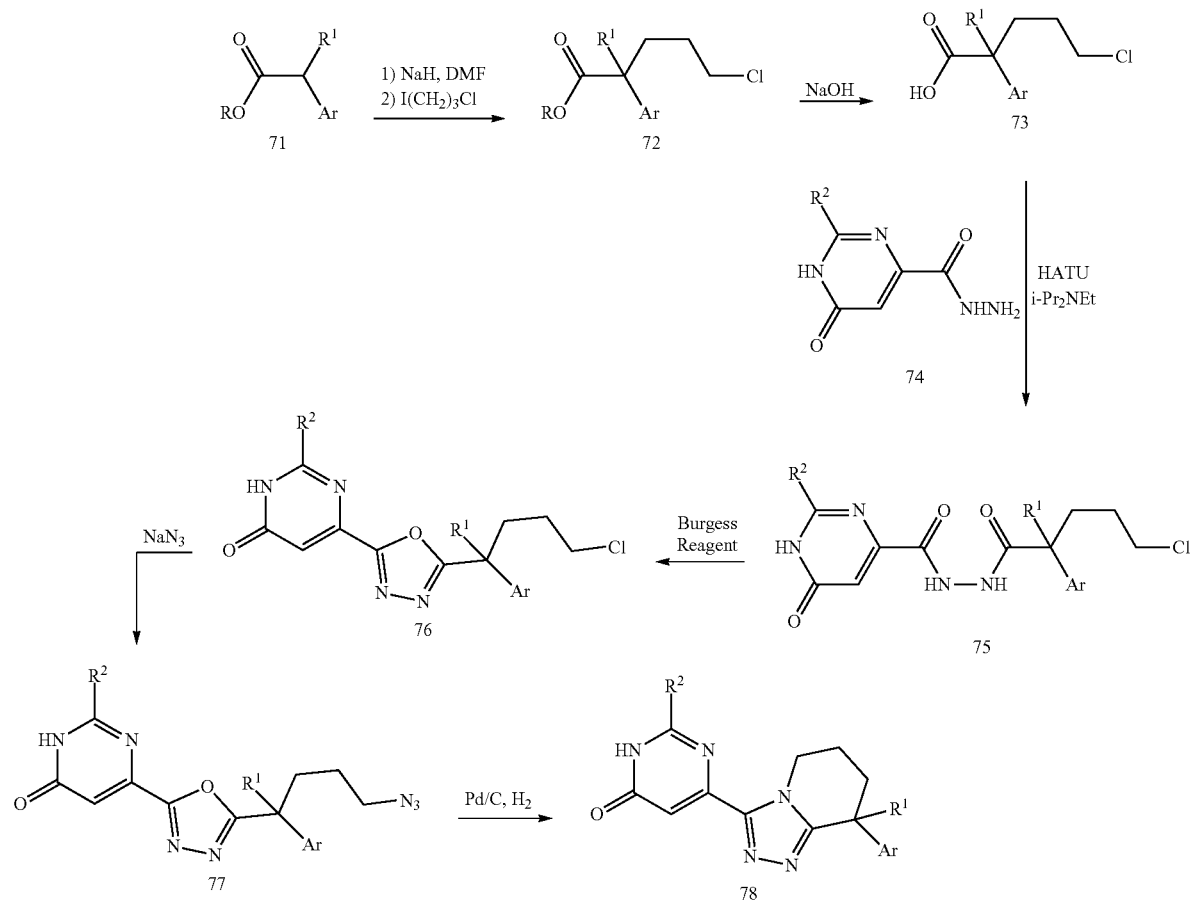

Scheme 16 illustrates a synthetic sequence for the preparation of triazole derivatives such as 78 from aryl acetic acid derivatives such as 71. Alkylation of 71 with 1-chloro-3-iodopropane provides the halogenated ester intermediate 72. Saponification of 72 with sodium hydroxide followed by coupling with hydrazides such as 74 provides the hydrazide intermediate 75. Dehydration of 75 with Burgess reagent provides oxadiazole 76. Nucleophilic displacement with sodium azide provides azido-oxadiazole 77 which is converted to the triazole 78 via sequential reduction of the azide with hydrogen and intramolecular condensation.

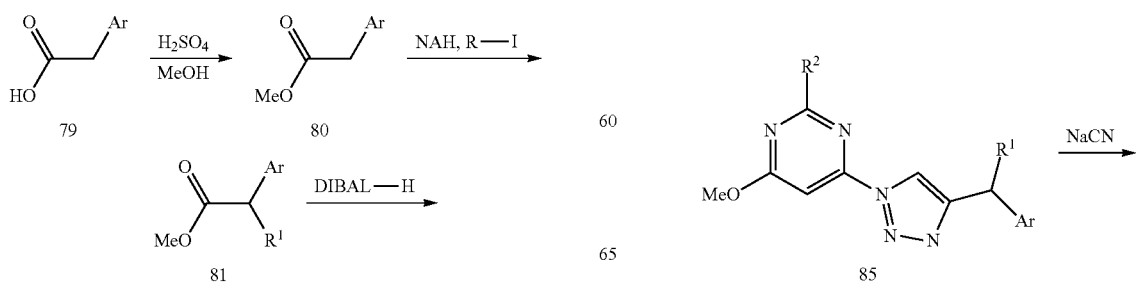

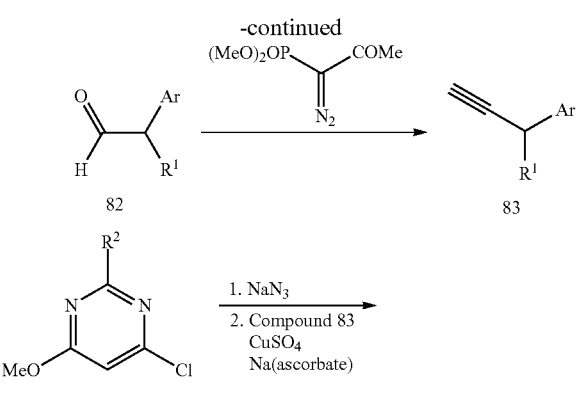

-continued

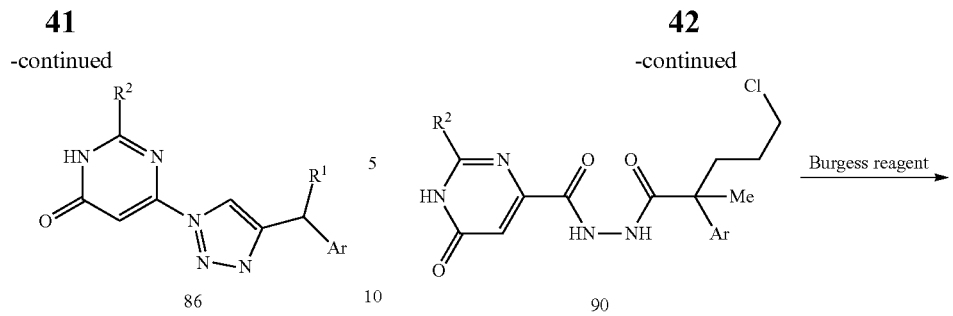

86

Scheme 17 illustrates a synthetic sequence for the preparation of 1,2,3-triazolylpyrimidinones such as 86 from aryl acetic acid derivatives such as 79. Alkylation of an ester such as 80, obtained from esterification of 79 under acidic conditions, with an alkyl iodide provides compound 81. 81 is reduced with DIBAL-H to afford the aldehyde 82 which can be converted to the alkyne 83. Alkyne 83 undergoes cycloaddition with an azide, obtained from an $S_NAr$ reaction of 84 with sodium azide, to furnish 85 which can be deprotected with sodium cyanide to provide 1,2,3-triazolylpyrimidine derivatives such as 86.

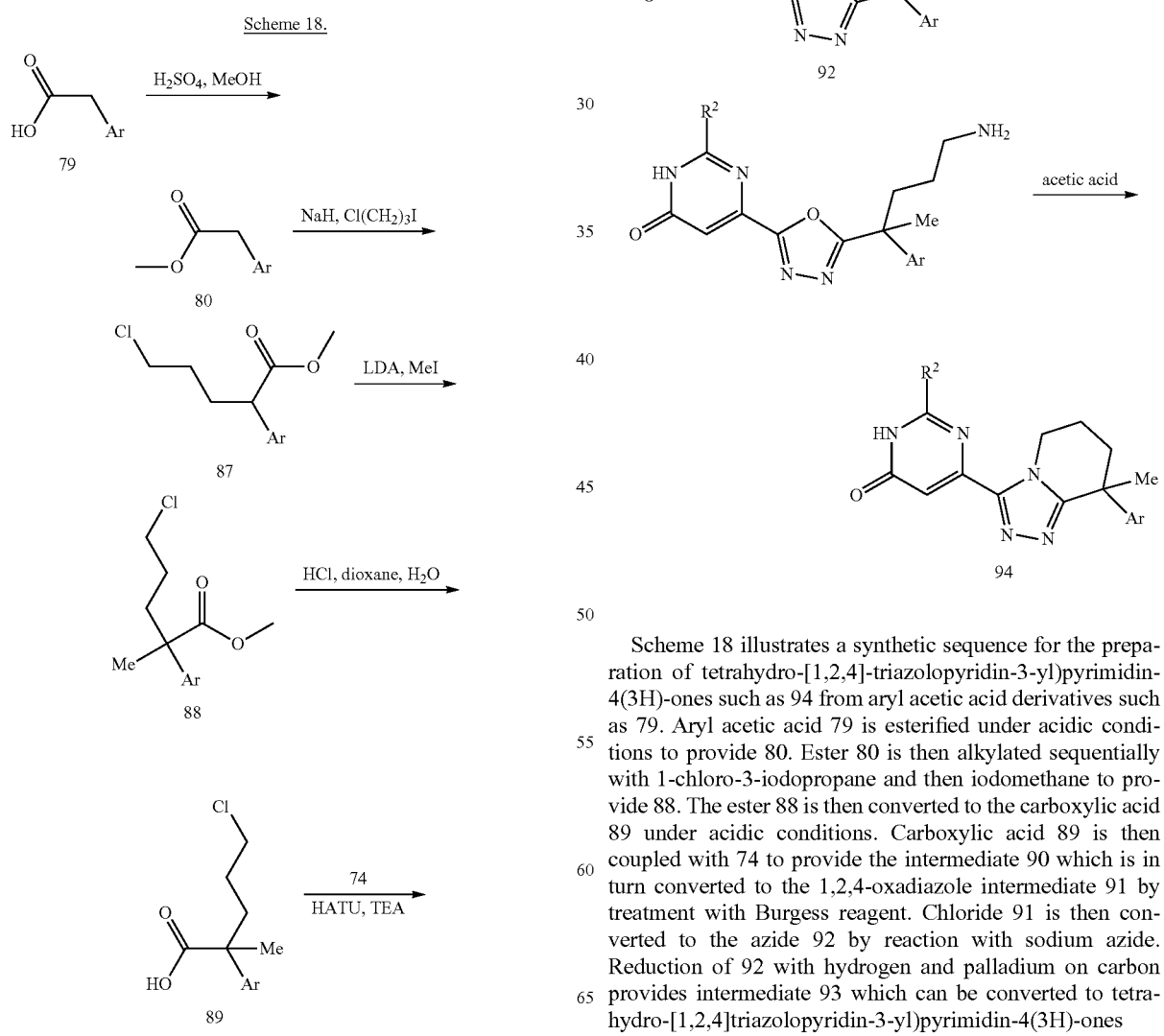

Scheme 18 illustrates a synthetic sequence for the preparation of tetrahydro-[1,2,4]-triazolopyridin-3-yl)pyrimidin-4(3H)-ones such as 94 from aryl acetic acid derivatives such as 79. Aryl acetic acid 79 is esterified under acidic conditions to provide 80. Ester 80 is then alkylated sequentially with 1-chloro-3-iodopropane and then iodomethane to provide 88. The ester 88 is then converted to the carboxylic acid 89 under acidic conditions. Carboxylic acid 89 is then coupled with 74 to provide the intermediate 90 which is in turn converted to the 1,2,4-oxadiazole intermediate 91 by treatment with Burgess reagent. Chloride 91 is then converted to the azide 92 by reaction with sodium azide. Reduction of 92 with hydrogen and palladium on carbon provides intermediate 93 which can be converted to tetrahydro-[1,2,4]triazolopyridin-3-yl)pyrimidin-4(3H)-ones such as 94.

Scheme 19.

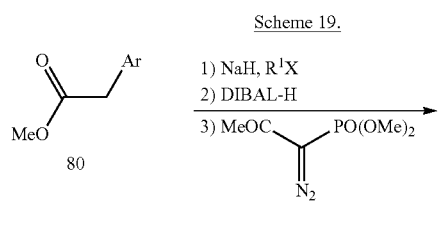

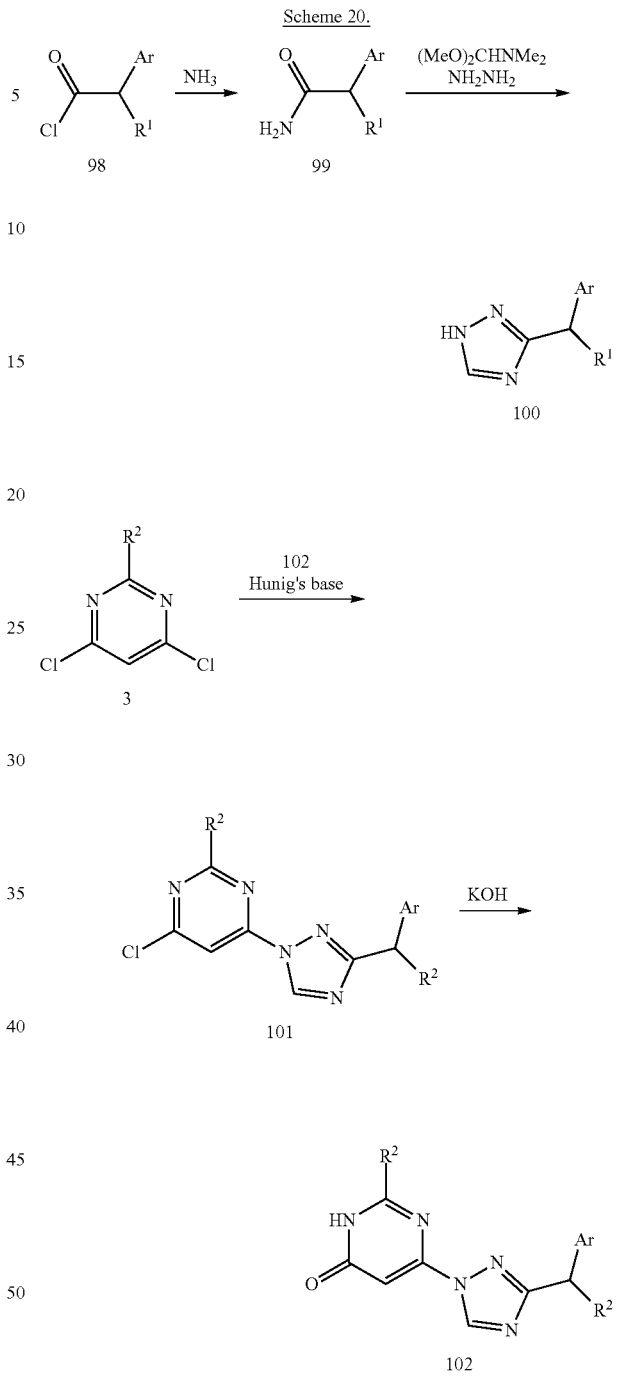

Scheme 19 illustrates a synthetic sequence for the preparation of 1,2,3-triazol-2-yl-pyrimidin-4(3H)-ones such as 97 from methyl arylacetate derivatives such as 80. Methyl arylacetate 80 can be converted to alkyne 83 in three step sequence consisting of alkylation, reduction, and treatment with dimethyl (1-diazo-2-oxopropyl)phosphonate. A 1,3-dipolar cycloaddition reaction of 83 with trimethylsilyl azide furnishes triazole 95. Reaction of 95 with pyrimidine 3 under basic conditions provides intermediate 96 which can be converted to 1,2,3-triazol-2-yl-pyrimidin-4(3H)-ones such as 97 by treatment with potassium hydroxide.

Scheme 20 illustrates a synthetic sequence for the preparation of 1,2,4-triazol-1-yl-pyrimidin-4(3H)-ones such as 102 from arylacetic acid derivatives such as 98. Amide intermediates such as 99 can be prepared from acid chlorides such as 98 by treatment with ammonia. 1,2,4-Triazoles such as 100 are prepared from primary amides such as 99 by treatment with dimethylformamide dimethyl acetal followed by a condensation reaction with hydrazine. Reaction of triazoles such as 100 with dichloropyrimidines such as 3 under basic conditions provides intermediate 101 which can be converted to 1,2,4-triazol-1-yl-pyrimidin-4(3H)-ones such as 102 by treatment with potassium hydroxide.

Scheme 21.

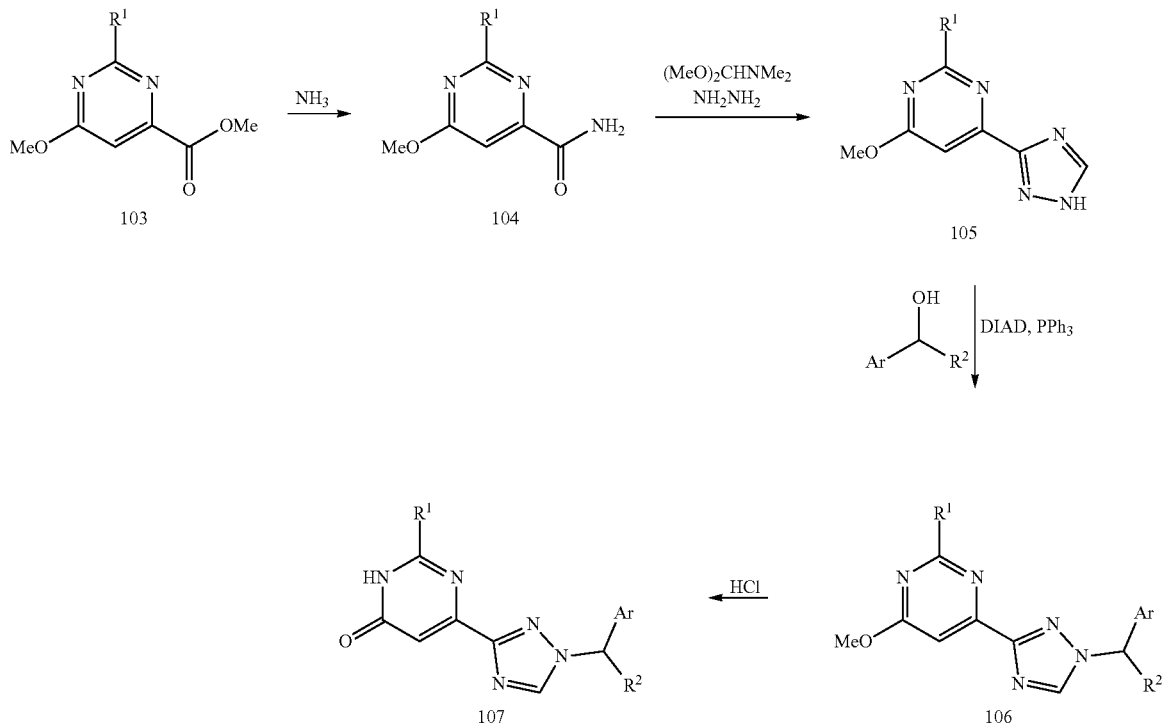

Scheme 21 illustrates a synthetic sequence for the preparation of 1,2,4-triazol-3-yl-pyrimidin-4(3H)-ones such as 107 from pyrimidines such as 103. Treatment of ester 103 with ammonia furnishes primary amide 104 which can subsequently be converted to triazoles such as 105 by treatment with dimethylformamide dimethylacetal followed by condensation with hydrazine. Triazole 105 is alkylated under Mitsunobu conditions to provide intermediate 106 which is deprotected under acidic conditions to furnish 1,2,4-triazol-3-yl-pyrimidin-4(3H)-ones such as 107.

Scheme 22 illustrates a synthetic sequence for the preparation of tetrahydro-[1,2,3]-triazolo[1,5-a]pyridin-3-yl-pyrimidin-4(3H)-ones such as 111 from alkynylpyrimidines such as 108. Triazole intermediates such as 109 are prepared via a ruthenium-catalyzed 1,3-dipolar cycloaddition reaction between alkyne 108 and para-methoxybenzyl azide. Triazole 109 can be converted to tetrahydro-[1,2,3]-triazolo[1,5-a]pyridin-3-yl-pyrimidin-4(3H)-ones such as 111 by sequential treatment with potassium hydroxide and then TFA.

Scheme 22.

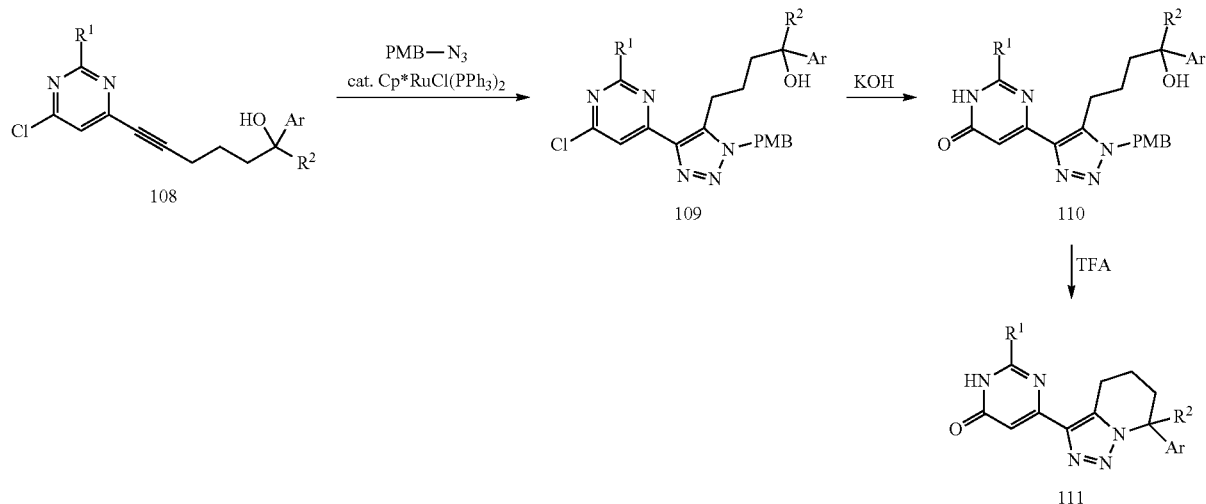

Scheme 23.

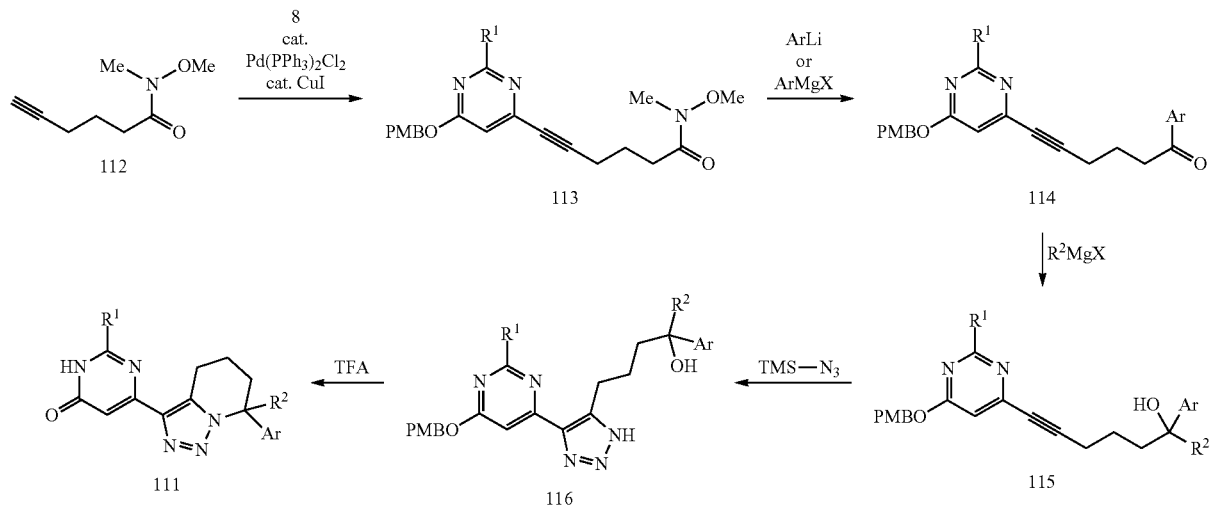

Scheme 23 illustrates a synthetic sequence for the preparation of tetrahydro-[1,2,3]-triazolo[1,5-a]pyridin-3-yl-pyrimidin-4(3H)-ones such as 111 from alkynylamides such as 112. Sonogashira coupling of alkynyl amides such as 112 with chloropyrimidines such as 8 provides alkynylpyrimidine amides such as 113. Amide 113 are converted to ketones such as 114 by treatment with aryllithium or Grignard reagents. Ketones such as 114 are then converted to tertiary alcohols such as 115 by treatment with Grignard reagents. 1,3-Dipolar cycloaddition of alkynes such as 115 with trimethylsilylazide provides triazolylpyrimidine intermediates such as 116 which can be converted to tetrahydro-[1,2,3]-triazolo[1,5-a]pyridin-3-yl-pyrimidin-4(3H)-ones such as 111 by treatment with trifluoroacetic acid.

Preparatory Examples 1 and 2

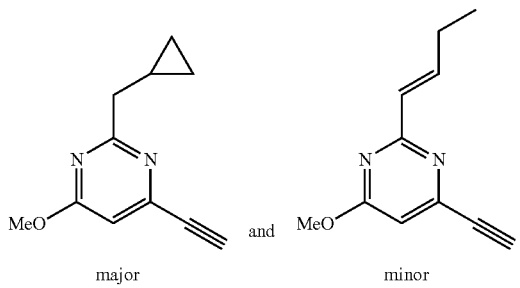

2-(Cyclopropylmethyl)-4-ethynyl-6-methoxy-pyrimidine and (E)-2-(but-1-enyl)-4-ethynyl-6-methoxypyrimidine (Scheme 1)

Step 1. 2-(Cyclopropylmethyl)pyrimidine-4,6-diol

To a mixture of NaOMe (4.95 g, 92.0 mmol) in methanol (80 mL) was added 2-cyclopropylacetimidamide hydrochloride (6.00 g, 44.8 mmol) at RT. The reaction mixture was stirred at RT for 5 minutes and then dimethyl malonate (5.91 g, 44.8 mmol) was added. The reaction mixture was stirred at 65° C. for 16 h. The resulting mixture was cooled and filtered. The filter cake was washed with methanol (80 mL). The combined filtrate was diluted with water (320 mL). The pH of the mixture was adjusted to 2 with aqueous 5M HCl. Then the mixture was filtered. The filter cake was washed with diethyl ether (20 mL) and dried to afford the title compound as a solid, which was used in next step without further purification. MS=167.1 (M+1).

Step 2. 4,6-Dichloro-2-(cyclopropylmethyl)pyrimidine and (E)-2-(but-1-enyl)-4,6-dichloropyrimidine A mixture of 2-(cyclopropylmethyl)pyrimidine-4,6-diol (3.80 g, 22.9 mmol) in phosphorus oxychloride (50 mL) was stirred at 100° C. for 2 h. The resulting solution was cooled and concentrated under reduced pressure. The residue was quenched with ice and water (100 g). The resulting mixture was extracted with EtOAc (3×100 mL). The combined organic extracts were washed with brine (2×100 mL), dried over anhydrous $Na_2SO_4$, and filtered. The filtrate was concentrated under reduced pressure to afford a mixture of the crude title compounds as a liquid. This mixture was used in the next step without further purification. MS=203.1 (M+1).

Step 3. 4-Chloro-2-(cyclopropylmethyl)-6-methoxy-pyrimidine and (E)-2-(but-1-enyl)-4-chloro-6-methoxypyrimidine To a solution of 4,6-dichloro-2-(cyclopropylmethyl)-pyrimidine and (E)-2-(but-1-enyl)-4,6-dichloropyrimidine (3.80 g, 18.7 mmol) in methanol (100 mL) was added NaOMe (1.01 g, 18.7 mmol). The reaction mixture was stirred at RT for 16 h. The resulting mixture was filtered. The filter cake was washed with methanol (200 mL). The eluent was concentrated under reduced pressure. The residue was diluted with EtOAc (200 mL). The resulting suspension was filtered and washed with EtOAc (100 mL). The filtrate was concentrated under reduced pressure to afford a mixture of the crude title compounds as a gum. This mixture was used in next step without further purification. MS=199.1 (M+1).

Step 4. 2-(Cyclopropylmethyl)-4-methoxy-6-((trimethylsilyl)ethynyl)pyrimidine and (E)-2-(but-1-enyl)-4-methoxy-6-((trimethylsilyl)ethynyl)pyrimidine To a solution of 4-chloro-2-(cyclopropylmethyl)-6-methoxypyrimidine and (E)-2-(but-1-enyl)-4-chloro-6-methoxypyrimidine (1.0 g, 5.0 mmol) in THF (4 mL) and TEA (6 mL) were added CuI (96.0 mg, 0.5 mmol), Pd(PPh$_3$)$_4$ (0.582 g, 0.5 mmol) and ethynyltrimethylsilane (0.79 g, 8.1 mmol). The reaction mixture was purged with nitrogen 3 times and stirred at 50° C. for 16 h. The resulting mixture was cooled to RT, diluted with water (60 mL) and extracted with EtOAc (3×60 mL). The combined organic extracts were washed with brine (80 mL), dried over anhydrous Na$_2$SO$_4$ and filtered. The filtrate was concentrated under reduced pressure. The residue was purified by silica gel chromatography (5-20% ethyl acetate in petroleum ether) to furnish the title compound after concentration. MS=261.2 (M+1).

Step 5. 2-(Cyclopropylmethyl)-4-ethynyl-6-methoxypyrimidine and (E)-2-(but-1-enyl)-4-ethynyl-6-methoxypyrimidine To a mixture of 2-(cyclopropylmethyl)-4-methoxy-6-((trimethylsilyl)ethynyl) pyrimidine and (E)-2-(but-1-enyl)-4-methoxy-6-((trimethylsilyl)ethynyl)-pyrimidine (1.27 g, 4.9 mmol) in THF (6 mL) was added a solution of KF (0.31 g, 5.4 mmol) in water (3 mL). The reaction mixture was stirred at 25° C. for 24 h. The resulting mixture was diluted with water (50 mL) and extracted with EtOAc (3×50 mL). The combined organic extracts were washed with brine (60 mL), dried with anhydrous Na$_2$SO$_4$, and filtered. The filtrate was concentrated under reduced pressure. The residue was purified by silica gel chromatography (5-20% ethyl acetate in petroleum ether) to furnish a mixture of the title compounds. MS=189.1 (M+1).

TABLE 1

The following compounds were prepared using procedures similar to those described in Preparatory Examples 1 and 2 using the appropriate starting materials.

| Preparatory Example No. | Structure | IUPAC Name | Exact Mass [M + H]$^+$ or [M + Na]$^+$ |
|---|---|---|---|
| 3 | 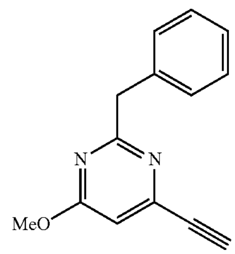 [SMILES: C#Cc1cc(OC)nc(Cc2ccccc2)n1] | 2-benzyl-4-ethynyl-6-methoxypyrimidine | Calc'd 225.1, found 225.1 |
| 4 | 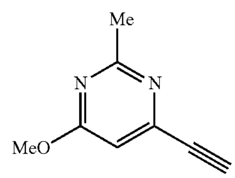 | 4-ethynyl-6-methoxy-2-methylpyrimidine | Calc'd 149.1, found 149.2 |
| 5 | 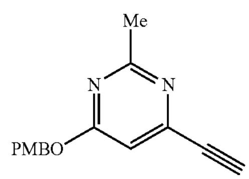 | 4-ethynyl-6-((4-methoxybenzyl)oxy)-2-methylpyrimidine | Calc'd 255.1, found 255.0 |

Preparatory Example 6

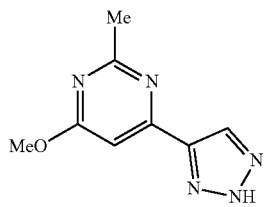 [SMILES: COc1cc(-c2cn[nH]n2)nc(C)n1]

4-Methoxy-2-methyl-6-(2H-1,2,3-triazol-4-yl)pyrimidine (Scheme 1)

4-Methoxy-2-methyl-6-(2H-1,2,3-triazol-4-yl)pyrimidine

To a solution of azidotrimethylsilane (1.17 g, 10.1 mmol) and 4-ethynyl-6-methoxy-2-methylpyrimidine (1.00 g, 6.75 mmol) in DMF (13.5 mL) and MeOH (1.5 mL) was added CuI (0.129 g, 0.7 mmol). The reaction mixture was purged with nitrogen 3 times, sealed and stirred at 100° C. for 4 h. The resulting mixture was cooled to RT and concentrated under vacuum. The residue was purified by silica gel chromatography (50% ethyl acetate in petroleum ether) to furnish the title compound. MS=192.0 (M+1).

Preparatory Example 7

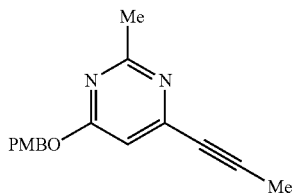

4-((4-Methoxybenzyl)oxy)-2-methyl-6-(prop-1-yn-1-yl)pyrimidine (Scheme 2)

4-((4-Methoxybenzyl)oxy)-2-methyl-6-(prop-1-yn-1-yl)pyrimidine

A solution of 4-chloro-6-((4-methoxybenzyl)oxy)-2-methylpyrimidine (250 mg, 0.944 mmol) and 4,4,5,5-tetramethyl-2-(prop-1-yn-1-yl)-1,3,2-dioxaborolane (314 mg, 1.889 mmol) in THF (2.5 ml) and water (0.5 ml) was degassed with nitrogen for 5 minutes. Then PdCl$_2$(dppf)-CH$_2$Cl$_2$ (38.6 mg, 0.047 mmol) and K$_2$CO$_3$ (392 mg, 2.83 mmol) were added and the reaction was heated to 60° C. overnight. The reaction was cooled to RT and diluted with water and ethyl acetate. The organic extract was separated and concentrated. The residue was then purified by silica gel chromatography (0-30% ethyl acetate in hexanes) to furnish the title compound. MS=268.96 (M+1).

Preparatory Example 8

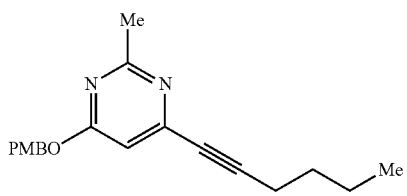

4-(Hex-1-yn-1-yl)-6-((4-methoxybenzyl)oxy)-2-methylpyrimidine (Scheme 2)

4-(Hex-1-yn-1-yl)-6-((4-methoxybenzyl)oxy)-2-methylpyrimidine

A solution of 4-chloro-6-((4-methoxybenzyl)oxy)-2-methylpyrimidine (500 mg, 1.889 mmol), hex-1-yne (0.425 ml, 3.78 mmol), and triethylamine (0.790 ml, 5.67 mmol) in THF (4 ml) was degassed with nitrogen for 5 minutes. Then bis(triphenylphosphine)palladium(II) chloride (106 mg, 0.151 mmol) and copper(I) iodide (43.2 mg, 0.227 mmol) were added and the reaction was heated to 65° C. overnight. The reaction was cooled to RT and concentrated. The residue was then purified by silica gel chromatography (ISCO 40 g silica cartridge; 0-30% ethyl acetate in hexanes) to furnish the title compound. MS=310.95 (M+1).

Preparatory Example 9

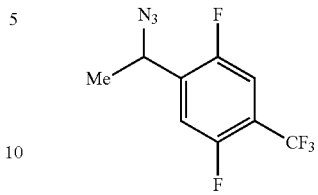

1-(1-Azidoethyl)-2,5-difluoro-4-(trifluoromethyl)benzene (Scheme 3)

Step 1.
4-Bromo-2,5-difluoro-N-methoxy-N-methylbenzamide

HATU (3.53 g, 9.3 mmol) was added to a solution of 4-bromo-2,5-difluorobenzoic acid (2.00 g, 8.4 mmol) in NMP (6 mL) at 0° C. The reaction suspension was stirred at 0° C. for 10 minutes. To the suspension was added N,O-dimethylhydroxylamine (0.670 g, 11.0 mmol). Then triethylamine (2.4 mL, 16.9 mmol) was added to the reaction mixture. The reaction was stirred at RT for 16 h. The resulting suspension was diluted with water (100 mL) and extracted with EtOAc (3×30 mL). The combined organic extracts were washed with brine (50 mL), dried with anhydrous Na$_2$SO$_4$ and filtered. The filtrate was concentrated under reduced pressure. The residue was purified by silica gel chromatography (35% ethyl acetate in petroleum ether) to furnish the title compound. MS=280.0/282.0 (M+1).

Step 2. 1-(4-Bromo-2,5-difluorophenyl)ethanone

To a solution of 4-bromo-2,5-difluoro-N-methoxy-N-methylbenzamide (1.82 g, 6.5 mmol) in THF (3.7 mL) was added MeMgBr (1 M in THF, 16.3 mL, 16.3 mmol) at 0° C. under an atmosphere of nitrogen. The reaction solution was stirred at RT for 4 h. The resulting suspension was quenched with saturated NH$_4$Cl solution (100 mL) and extracted with EtOAc (2×100 mL). The combined organic extracts were washed with brine (2×100 mL), dried over anhydrous Na$_2$SO$_4$, and filtered. The filtrate was concentrated under reduced pressure. The residue was purified by silica gel chromatography (4% of ethyl acetate in petroleum ether) to furnish the title compound. $^1$H NMR (400 MHz, CDCl$_3$) δ: 7.64 (dd, J=8.4 Hz, 6.0 Hz, 1H), 7.42 (dd, J=9.6 Hz, 5.2 Hz, 1H), 2.63 (s, 3H).

Step 3.
1-(2,5-Difluoro-4-(trifluoromethyl)phenyl)ethanone

To a solution of 1-(4-bromo-2,5-difluorophenyl)ethanone (0.800 g, 3.4 mmol) in NMP (3 mL) were added methyl 2,2-difluoro-2-(fluorosulfonyl)acetate (2.62 g, 13.6 mmol) and CuI (0.648 g, 3.4 mmol). The mixture was purged with nitrogen 3 times and stirred at 130° C. for 16 h under an atmosphere of nitrogen. The mixture was cooled to RT and diluted with EtOAc (100 mL). The organic layer was washed with brine (2×100 mL), dried with anhydrous Na$_2$SO$_4$, and filtered. The filtrate was concentrated under reduced pressure. The residue was purified by silica gel chromatography (11% of ethyl acetate in petroleum ether) to furnish the title compound. MS=223.9 (M+1).

Step 4.
1-(2,5-Difluoro-4-(trifluoromethyl)phenyl)ethanol

To a solution of 1-(2,5-difluoro-4-(trifluoromethyl)phenyl)ethanone (0.200 g, 0.9 mmol) in MeOH (2 mL) cooled to 0° C. was added NaBH$_4$ (33.8 mg, 0.9 mmol). The reaction mixture was stirred for 2 h at 0° C. The resulting mixture was concentrated under reduced pressure. The residue was diluted with EtOAc (50 mL) and washed with brine (2×50 mL). The combined organic extracts were dried with anhydrous Na$_2$SO$_4$ and filtered. The filtrate was concentrated under reduced pressure. The residue was purified by silica gel chromatography (40% ethyl acetate in petroleum ether) to furnish the title compound. $^1$H NMR (400 MHz, CDCl$_3$) δ: 7.42 (dd, J=10.8 Hz, 5.6 Hz, 1H), 7.27 (dd, J=9.0 Hz, 5.6 Hz, 1H), 5.21 (q, J=6.4 Hz, 1H), 1.51 (d, J=6.4 Hz, 3H).

Step 5. 1-(1-Azidoethyl)-2,5-difluoro-4-(trifluoromethyl)benzene

DBU (0.24 mL, 1.6 mmol) was added dropwise to a solution of 1-(2,5-difluoro-4-(trifluoromethyl)phenyl)ethanol (1.20 g, 0.5 mmol) and DPPA (0.438 g, 1.6 mmol) in THF (1.5 mL) cooled to 0° C. The reaction solution was stirred at RT for 16 h. The resulting solution was concentrated under reduced pressure. The residue was diluted with hexane (20 mL) and the mixture was stirred at RT for 30 minutes. Then it was filtered through a plug of silica gel. The filtrate was concentrated under reduced pressure to afford the crude title compound as a liquid, which was used in next step without further purification. MS=223.9 (M−28+H).

TABLE 2

The following compounds were prepared according to the procedures similar to those detailed in Preparatory Example 9 using the appropriate starting materials.

| Preparatory Example No. | Structure | IUPAC Name | Exact Mass [M − 28 + H]$^+$ |
|---|---|---|---|
| 10 | 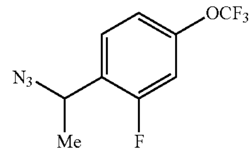 [SMILES: CC(N=[N+]=[N-])c1ccc(OC(F)(F)F)cc1F] | 1-(1-azidoethyl)-2-fluoro-4-(trifluoromethoxy)benzene | Calc'd 222.1, found 222.0 |
| 11 | 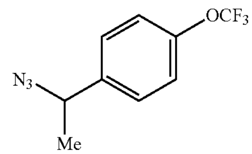 [SMILES: CC(N=[N+]=[N-])c1ccc(OC(F)(F)F)cc1] | 1-(1-azidoethyl)-4-(trifluoromethoxy)benzene | Calc'd 204.1, found 203.9 |
| 12 | 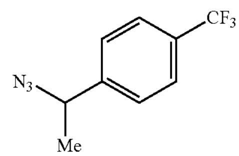 [SMILES: CC(N=[N+]=[N-])c1ccc(C(F)(F)F)cc1] | 1-(1-azidoethyl)-4-(trifluoromethyl)benzene | Calc'd 188.1, found 188.2 |
| 13 | 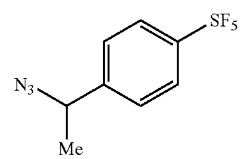 | 1-(1-azidoethyl)-4-(pentafluorothio)benzene | Calc'd 246.0, found 245.9 |
| 14 | 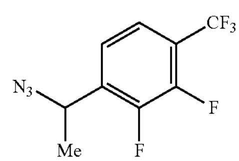 [SMILES: CC(N=[N+]=[N-])c1ccc(C(F)(F)F)c(F)c1F] | 1-(1-azidoethyl)-2,3-difluoro-4-(trifluoromethyl)benzene | Calc'd 224.1, found 224.1 |

Preparatory Example 15

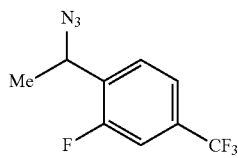 [SMILES: CC(N=[N+]=[N-])c1ccc(C(F)(F)F)cc1F]

1-(1-Azidoethyl)-2-fluoro-4-(trifluoromethyl)benzene (Scheme 4)

Step 1.
1-(2-Fluoro-4-(trifluoromethyl)phenyl)ethanol

Methylmagnesium bromide (3.0 M in diethyl ether, 1.0 mL, 3.0 mmol) was added dropwise to a solution of 2-fluoro-4-(trifluoromethyl)-benzaldehyde (0.300 g, 1.6 mmol) in THF (4.0 mL) cooled to −78° C. The reaction mixture was warmed to RT and stirred under an atmosphere of nitrogen for 1 h. The resulting solution was quenched with saturated NH$_4$Cl solution (10 mL), diluted with brine (30 mL), and extracted with EtOAc (3×40 mL). The combined organic extracts were dried over anhydrous Na$_2$SO$_4$ and filtered. The filtrate was concentrated under reduced pressure to afford the crude title compound as a liquid, which was used in next step without further purification. $^1$H NMR (300 MHz, CD$_3$OD) δ: 7.78-7.73 (m, 1H), 7.51 (d, J=8.1 Hz, 1H), 7.39 (d, J=10.2 Hz, 1H), 5.18 (q, J=6.6 Hz, 1H), 1.47 (d, J=6.6 Hz, 3H).

Step 2. 1-(1-Azidoethyl)-2-fluoro-4-(trifluoromethyl)benzene

The title compound was prepared using procedures similar to those described in Preparatory Example 9, step 5 using 1-(2-fluoro-4-(trifluoromethyl) phenyl)ethanol to afford the title compound as a liquid. MS=206.0 (M−28+H).

Preparatory Example 20

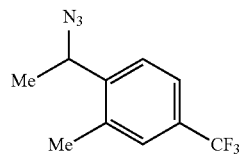

1-(1-Azidoethyl)-2-methyl-4-(trifluoromethyl)benzene (Scheme 5)

Step 1. 1-(2-Methyl-4-(trifluoromethyl)phenyl)ethanone

To a mixture of tributyl(1-ethoxyvinyl)stannane (1.81 g, 5.02 mmol) and 1-bromo-2-methyl-4-(trifluoromethyl)benzene (0.800 g, 3.4 mmol) in toluene (1.5 mL) was added tetrakis(triphenylphosphine)palladium(0) (0.387 g, 0.3 mmol). The mixture was purged with nitrogen 3 times and stirred at 120° C. for 2.5 h. The resulting mixture was cooled to RT and diluted with EtOAc (80 mL). The mixture was washed with saturated Na$_2$CO$_3$ solution (2×10 mL), brine (10 mL), dried with anhydrous Na$_2$SO$_4$ and filtered. The filtrate was concentrated under reduced pressure to afford the crude 1-(1-ethoxyvinyl)-2-methyl-4-(trifluoromethyl) benzene as a liquid. 1-(1-Ethoxyvinyl)-2-methyl-4-(trifluoromethyl)benzene was dissolved in THF (4 mL) and treated with HCl (6 M in water, 2.6 mL). The reaction solution was

TABLE 3

The following compounds were prepared according to procedures similar to those described in preparatory example 15 using the appropriate starting materials.

| Preparatory Example No. | Structure | IUPAC Name | Exact Mass [M]$^+$ or $^1$H NMR |
|---|---|---|---|
| 16 | 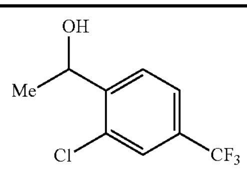 | 1-(2-chloro-4-(trifluoromethyl)phenyl)ethanol | Calc'd 224.0/226.0, found 224.1/226.0 |
| 17 | 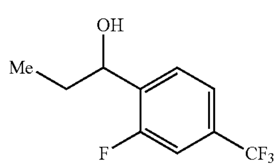 [SMILES: CCC(O)c1ccc(C(F)(F)F)cc1F] | 1-(2-fluoro-4-(trifluoromethyl)phenyl)propan-1-ol | $^1$H NMR (500 MHz, DMSO-d$_6$) δ: 7.71 (t, J = 9 Hz, 1), 7.59-7.57 (m, 2H), 5.47 (d, J = 5 Hz, 1H), 4.80 (q, J = 6 Hz, 1H), 1.65-1.59 (m, 2H), 0.84 (t, J = 7 Hz, 3H). |
| 18 | 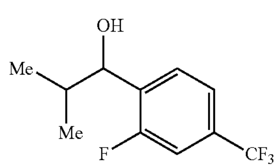 [SMILES: CC(C)C(O)c1ccc(C(F)(F)F)cc1F] | 1-(2-fluoro-4-(trifluoromethyl)phenyl)-2-methylpropan-1-ol | $^1$H NMR (500 MHz, DMSO-d$_6$) δ: 7.68 (m, 1H), 7.56 (m, 2H), 5.44 (d, J = 4.5 Hz, 1H), 4.62 (m, 1H), 1.83 (m, 1H), 0.84 (d, J = 6.5 Hz, 3H), 0.79 (d, J = 7 Hz, 3H). |
| 19 | | cyclopropyl(2-fluoro-4-(trifluoromethyl)phenyl)methanol | $^1$H NMR (500 MHz, DMSO-d$_6$) δ: 7.70 (m, 1H), 7.45 (d, J = 8 Hz, 1H), 7.31 (d, J = 10 Hz, 1H), 4.42 (d, J = 8 Hz, 1H), 2.11 (s, 1H), 1.21 (m, 1H), 0.66 (m, 1H), 0.56-0.47 (m, 3H). | stirred at RT for 2 h. The resulting solution was quenched with saturated Na$_2$CO$_3$ (10 mL) solution and extracted with EtOAc (3×20 mL). The combined organic extracts were washed with brine (2×5 mL), dried with anhydrous Na$_2$SO$_4$ and filtered. The filtrate was concentrated under reduced pressure. The residue was purified by silica gel chromatography (0-25% ethyl acetate in petroleum ether) to furnish the title compound. $^1$H NMR (300 MHz, CDCl$_3$) δ: 7.74 (d, J=8.4 Hz, 1H), 7.53 (d, J=8.4 Hz, 1H), 7.51 (s, 1H), 2.63 (s, 3H), 2.56 (s, 3H).

Step 2. 1-(5-(Trifluoromethyl)pyridin-2-yl)ethanol

The title compound was prepared using procedures similar to those described in Preparatory Example 9, step 4 using 1-(2-methyl-4-(trifluoromethyl)phenyl) ethanone as the starting material. $^1$H NMR (400 MHz, CDCl$_3$) δ: 7.67 (d, J=8.4 Hz, 1H), 7.51 (d, J=8.4 Hz, 1H), 7.41 (s, 1H), 5.19 (q, J=6.8 Hz, 1H), 2.41 (s, 3H), 1.49 (d, J=6.8 Hz, 3H).

Step 3. 1-(1-Azidoethyl)-2-methyl-4-(trifluoromethyl)benzene

The title compound was prepared using procedures similar to those described in Preparatory Example 9, step 5 using 1-(2-methyl-4-(trifluoromethyl)phenyl)ethanol as the starting material. MS=202.0 (M−28+H).

Preparatory Example 21

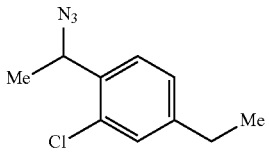 [SMILES: CCc1ccc(C(C)N=[N+]=[N-])c(Cl)c1]

1-(1-Azidoethyl)-2-chloro-4-ethylbenzene (Scheme 6)

Step 1. 1-(2-Chloro-4-vinylphenyl)ethanone

The title compound was prepared using procedures similar to those described in Preparatory Example 20, step 1 using 1-(4-bromo-2-chlorophenyl)ethanone and tributylvinylstannane as the starting materials. MS=180.9/182.9 (M+1).

Step 2. 1-(2-Chloro-4-ethylphenyl)ethanone

To a solution of 1-(2-chloro-4-vinylphenyl)ethanone (1.10 g, 6.1 mmol) in EtOAc (30 mL) was added 10% palladium on carbon (0.100 g). The reaction mixture was purged with hydrogen 3 times and stirred under hydrogen balloon for 1 h at RT. The solids were filtered out. The filtrate was concentrated under reduced pressure to furnish the crude title compound as a liquid, which was used in next step without further purification. MS=183.0/185.0 (M+1).

Step 3. 1-(2-Chloro-4-ethylphenyl)ethanol

The title compound was prepared using procedures similar to those described in Preparatory Example 9, step 4 using 1-(2-chloro-4-ethylphenyl)ethanone as the starting material. MS=184.0/186.0.

Step 4. 1-(1-Azidoethyl)-2-chloro-4-ethylbenzene

The title compound was prepared using procedures similar to those described in preparatory example 9, step 5 using 1-(2-chloro-4-ethylphenyl)ethanol as the starting material. MS=182.0/184.0. (M−28+H)

Preparatory Example 22

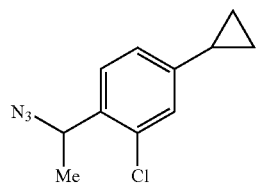 [SMILES: CC(N=[N+]=[N-])c1ccc(C2CC2)cc1Cl]

1-(1-Azidoethyl)-2-chloro-4-cyclopropylbenzene (Scheme 7)

Step 1. 1-(2-Chloro-4-vinylphenyl)ethanone

Tributyl(vinyl)stannane (2.45 g, 7.7 mmol) was added to a mixture of 1-(4-bromo-2-chlorophenyl)ethanone (1.50 g, 6.4 mmol) in DMF (10.0 mL) at RT. The reaction mixture was purged with nitrogen 3 times, then to the mixture was added tetrakis(triphenylphosphine) palladium(0) (0.74 g, 0.6 mmol). The reaction mixture was purged with nitrogen 3 times again and stirred under nitrogen atmosphere at 100° C. for 3 h. The resulting mixture was cooled and concentrated under reduced pressure. The residue was diluted with ethyl acetate (300 mL) and washed with brine (2×20 mL), dried with anhydrous Na$_2$SO$_4$ and filtered. The filtrate was concentrated under reduced pressure. The residue was purified by column chromatography over silica gel (5% EA in petroleum ether) to afford the title compound. $^1$H NMR (400 MHz, CDCl$_3$) δ: 7.59 (d, J=8.0 Hz, 1H), 7.47 (d, J=0.8 Hz, 1H), 7.36 (dd, J=8.0 and 0.8 Hz, 1H), 6.69 (dd, J=17.6 and 10.8 Hz, 1H), 5.87 (d, J=17.6 Hz, 1H), 5.44 (d, J=10.8 Hz, 1H), 2.68 (s, 3H).

Step 2. 1-(2-Chloro-4-cyclopropylphenyl)ethanone

A solution of trifluoroacetic acid (1.1 mL, 14.2 mmol) in DCM (10.0 mL) was added dropwise to a solution of diethylzinc (1.0 M in hexane, 14.2 mL, 14.2 mmol) in DCM (40 mL) at 0° C. The reaction suspension was stirred at 0° C. for 10 minutes. To the reaction suspension was added a solution of diiodomethane (1.1 mL, 14.2 mmol) in DCM (2 mL) at 0° C. The reaction suspension was stirred at 0° C. for 10 minutes. Then a solution of 1-(2-chloro-4-vinylphenyl) ethanone (0.570 g, 3.2 mmol) in DCM (2 mL) was added dropwise to the reaction suspension at 0° C. The reaction mixture was stirred at 0° C. for 30 minutes and warmed to RT. After 16 h, the resulting suspension was quenched with saturated NH$_4$Cl solution (50 mL) and extracted with dichloromethane (3×50 mL). The combined organic extracts were washed with brine (100 mL), dried with anhydrous Na$_2$SO$_4$ and filtered. The filtrate was concentrated under reduced pressure. The residue was purified by column chromatography over silica gel (100% hexanes) to afford the title compound. $^1$H NMR (400 MHz, CDCl$_3$) δ: 7.52 (d, J=8.0

Hz, 1H), 7.09 (d, J=0.8 Hz, 1H), 6.98-6.93 (dd, J=8.0 and 0.8 Hz, 1H), 2.65 (s, 3H), 1.92-1.86 (m, 1H), 1.08-1.03 (m, 2H), 0.78-0.73 (m, 2H).

Step 3. 1-(2-Chloro-4-cyclopropylphenyl)ethanol

NaBH$_4$ (78.0 mg, 2.0 mmol) was added to a solution of 1-(2-chloro-4-cyclopropylphenyl)ethanone (0.200 g, 1.03 mmol) in MeOH (5.0 mL). The reaction solution was stirred at RT for 2 h. The resulting solution was concentrated under reduced pressure. The residue was purified by column chromatography over silica gel (gradient from 10-20% of ethyl acetate in petroleum ether) to furnish the title compound. $^1$H NMR (400 MHz, CDCl$_3$) δ: 7.44 (d, J=8.4 Hz, 1H), 7.03-6.99 (m, 2H), 5.25 (q, J=6.4 Hz, 1H), 1.90-1.82 (m, 1H), 1.47 (d, J=6.4 Hz, 3H), 0.98-0.92 (m, 2H), 0.70-0.66 (m, 2H).

Step 4. 1-(1-Azidoethyl)-2-chloro-4-cyclopropylbenzene

The title compound was prepared using a procedure similar to that described for preparatory example 9, step 5 using 1-(2-chloro-4-cyclopropylphenyl)ethanol as the starting material. MS=194.0/196.0 (M−28+H).

Preparatory Example 23

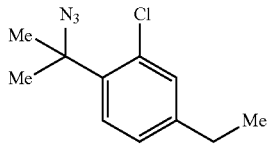 [SMILES: CCc1ccc(C(C)(C)N=[N+]=[N-])c(Cl)c1]

1-(2-Azidopropan-2-yl)-2-chloro-4-ethylbenzene (Scheme 8)

Step 1. Methyl 4-bromo-2-chlorobenzoate

SOCl$_2$ (1.5 mL, 20.4 mmol) was added dropwise to a solution of 4-bromo-2-chlorobenzoic acid (4.00 g, 17.0 mmol) in MeOH (100 mL) cooled to 0° C. The reaction mixture was stirred for 24 h at RT and was stirred for additional 24 h at 60° C. The resulting mixture was cooled. The pH of the reaction mixture was adjusted to 8 with aqueous NaOH (1 M). The mixture was concentrated under reduced pressure. The residue was dissolved in EtOAc (100 mL) and washed with brine (100 mL). The organic extract was dried with anhydrous Na$_2$SO$_4$ and filtered. The filtrate was concentrated under reduced pressure to afford the title compound as a liquid, which was used in next step without further purification. MS=247.8/249.8/251.8 (M).

Step 2. Methyl 2-chloro-4-vinylbenzoate

The title compound was prepared using procedures similar to those described in preparatory example 20, step 1 using methyl 4-bromo-2-chlorobenzoate and tributylvinylstannane as the starting materials. MS=196.0/198.0 (M).

Step 3. Methyl 2-chloro-4-ethylbenzoate

The title compound was prepared using procedures similar to those described in Preparatory Example 21, step 2 using methyl 2-chloro-4-vinylbenzoate as the starting material. MS=197.9/199.9 (M).

Step 4. 2-(2-Chloro-4-ethylphenyl)propan-2-ol

Methylmagnesium bromide (1 M in THF, 11.6 mL, 11.6 mmol) was added dropwise to a solution of methyl 2-chloro-4-ethylbenzoate (0.460 g, 2.3 mmol) in THF (5 mL) cooled to 0° C. under and atmosphere of nitrogen. The reaction mixture was stirred for 3 h at 0° C. The resulting mixture was quenched with saturated NH$_4$Cl solution (30 mL) and EtOAc (100 mL). The organic extract was washed with brine (2×100 mL), dried over anhydrous Na$_2$SO$_4$ and filtered. The filtrate was concentrated under reduced pressure. The residue was purified by silica gel chromatography (20% ethyl acetate in petroleum ether) to furnish the title compound. MS=198.0/199.9 (M).

Step 5. 1-(2-Azidopropan-2-yl)-2-chloro-4-ethylbenzene

To a solution of 2-(2-chloro-4-ethylphenyl)propan-2-ol (35.0 mg, 0.2 mmol) in DCM (0.5 mL) were added InBr$_3$ (12.5 mg, 0.04 mmol) and TMS-azide (0.100 g, 0.9 mmol) at RT under an atmosphere of nitrogen. The reaction mixture was stirred for 16 h at RT. The resulting mixture was diluted with EtOAc (50 mL), and washed with brine (2×50 mL). The organic extract was dried with anhydrous Na$_2$SO$_4$ and filtered. The filtrate was concentrated under reduced pressure to afford the crude title compound as a liquid, which was used directly in the next step without further purification. MS=196.0/198.1. (M−28+H).

TABLE 4

The following compounds were prepared using procedures similar to those described in preparatory example 23 using the appropriate starting materials.

| Preparatory Example No. | Structure | IUPAC Name | Exact Mass [M − 28 + H]$^+$ |
| --- | --- | --- | --- |
| 24 | ![structure] | 1-(2-azidopropan-2-yl)-2-chloro-4-(trifluoromethyl)benzene | Calc'd 236.1/238.1, found 236.1/238.1 |

TABLE 4-continued

The following compounds were prepared using procedures similar to those described in preparatory example 23 using the appropriate starting materials.

| Preparatory Example No. | Structure | IUPAC Name | Exact Mass [M − 28 + H]+ |
|---|---|---|---|
| 25 | 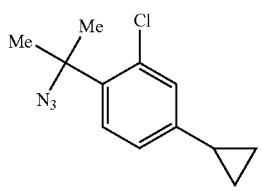 [SMILES: CC(C)(N=[N+]=[N-])c1ccc(C2CC2)cc1Cl] | 1-(2-azidopropan-2-yl)-2-methyl-4-(trifluoromethyl)benzene | Calc'd 216.1, found 216.0 |
| 26 | 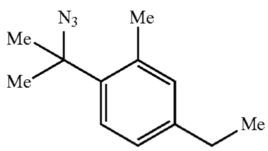 | 1-(2-azidopropan-2-yl)-4-ethyl-2-methylbenzene | Calc'd 176.2, found 176.2 |

Preparatory Example 27

1-(2-Azidopropan-2-yl)-2-chloro-4-cyclopropylbenzene (Scheme 9)

Step 1. 1-(2-Chloro-4-cyclopropylphenyl)ethanone

A mixture of 1-(4-bromo-2-chlorophenyl)ethanone (2.50 g, 10.7 mmol), cyclopropyl boronic acid (0.966 g, 11.2 mmol), $Pd(OAc)_2$ (0.240 g, 1.1 mmol), $PCy_3 \cdot HBF_4$ (0.394 g, 1.1 mmol) and $K_3PO_4$ (6.82 g, 32.1 mmol) in toluene (10 mL) was purged with nitrogen 3 times, sealed and stirred under nitrogen atmosphere for 3 h at 80° C. The resulting mixture was cooled to RT, diluted with water (100 mL) and the product was extracted with EtOAc (3×40 mL). The combined organic extracts were washed with brine (100 mL), dried with anhydrous $Na_2SO_4$ and filtered. The filtrate was concentrated under reduced pressure. The residue was purified by silica gel chromatography (3% ethyl acetate in petroleum ether) to furnish the title compound. MS=195.1/197.0 (M).

Step 2. 2-(2-Chloro-4-cyclopropylphenyl)propan-2-ol

The title compound was prepared using procedures similar to those described in Preparatory Example 15, step 1 using 1-(2-chloro-4-cyclopropylphenyl)ethanone as the starting material. $^1$H NMR (400 MHz, $CDCl_3$) δ: 7.50 (d, J=8.4 Hz, 1H), 7.05 (d, J=2.0 Hz, 1H), 6.94 (dd, J=8.0 Hz, 2.0 Hz, 1H), 1.87-1.83 (m, 1H), 1.70 (s, 6H), 1.00-0.95 (m, 2H), 0.71-0.69 (m, 2H).

Step 3. 1-(2-Azidopropan-2-yl)-2-chloro-4-cyclopropylbenzene

The title compound was prepared using procedures similar to those described in Preparatory Example 23, step 5 using 2-(2-chloro-4-cyclopropylphenyl) propan-2-ol as the starting material. MS=208.0/209.9. (M−28+H)

TABLE 5

The following compound was prepared using procedures similar to those described in Preparatory Example 27 using the appropriate starting materials.

| Preparatory Example No. | Structure | IUPAC Name | Exact Mass [M − 28 + H]+ |
|---|---|---|---|
| 28 | 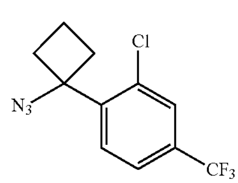 [SMILES: [N-]=[N+]=NC1(c2ccc(C(F)(F)F)cc2Cl)CCC1] | 1-(1-azidocyclobutyl-2-chloro-4-(trifluoromethyl)benzene | Calc'd 248.1/250.1, found 248.1/250.1 |

Preparatory Example 29

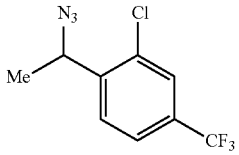 [SMILES: CC(N=[N+]=[N-])c1ccc(C(F)(F)F)cc1Cl]

1-(1-azidoethyl)-2-chloro-4-(trifluoromethyl)benzene (Scheme 10)

Step 1. 1-(2-Chloro-4-(trifluoromethyl)phenyl)ethan-1-ol

DMSO (7.73 ml, 109 mmol) was added to a −78° C. solution of oxalyl chloride (4.77 ml, 54.5 mmol) in dichloromethane (100 ml). The mixture was stirred for 10 minutes before the addition of (2-chloro-4-(trifluoromethyl)-phenyl)methanol (7.65 g, 36.3 mmol) as a solution in dichloromethane (100 ml). This mixture was stirred for 30 minutes at −78° C. and then treated with triethylamine (25.3 ml, 182 mmol). The resulting mixture was stirred for 20 minutes at −78° C. and then warmed to RT and stirred for 1 h. The reaction was then quenched with saturated NaHCO$_3$ solution and the aqueous layer was extracted with dichloromethane. The organic extracts were combined and washed with 1N HCl, water, and then dried over Na$_2$SO$_4$. This mixture was filtered and concentrated. The crude aldehyde was then dissolved in THF (85 ml) and the solution was cooled to 0° C. before the addition of methylmagnesium bromide (15.74 ml, 47.2 mmol). After 5 minutes the reaction was quenched with saturated NH$_4$Cl solution and the product was extracted with ethyl acetate. The organic extract was dried over Na$_2$SO$_4$, filtered, and concentrated. The product was purified by silica gel chromatography (0-30% ethyl acetate in hexanes) to furnish the title compound. $^1$H NMR (500 MHz, CDCl$_3$) δ: 7.78 (d, J=8 Hz, 1H), 7.62 (s, 1H), 7.58 (d, J=8 Hz, 1H), 5.34 (q, J=6 Hz, 1H), 2.15 (broad, 1H), 1.53 (d, J=6 Hz, 3H).

Step 2. 1-(1-Azidoethyl)-2-chloro-4-(trifluoromethyl)benzene

DBU (161 μl, 1.069 mmol) was added to a solution of 1-(2-chloro-4-(trifluoromethyl)phenyl)ethanol (200 mg, 0.890 mmol) and diphenylphosphoryl azide (230 μl, 1.069 mmol) in THF (1.78 mL). The reaction was stirred overnight at RT. The mixture was concentrated and filtered through silica gel eluting with hexanes (~50 mL). The eluent was concentrated and the crude azide was used directly in the next step.

Examples 1 and 2

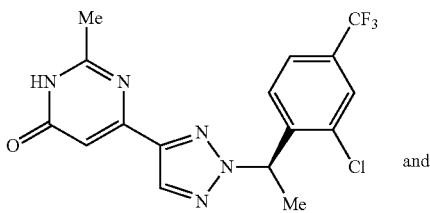

and

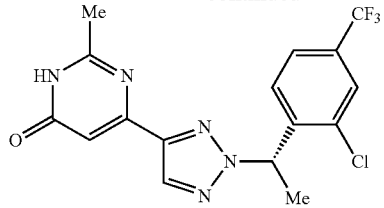

(R)- and (S)-6-(2-(1-(2-Chloro-4-(trifluoromethyl)phenyl)ethyl)-2H-1,2,3-triazol-4-yl)-2-methylpyrimidin-4(3H)-one (Scheme 11)

Step 1. 4-(2-(1-(2-Chloro-4-(trifluoromethyl)phenyl)ethyl)-2H-1,2,3-triazol-4-yl)-6-methoxy-2-methylpyrimidine To a mixture of 4-methoxy-2-methyl-6-(2H-1,2,3-triazol-4-yl)pyrimidine (0.100 g, 0.5 mmol), 1-(2-chloro-4-(trifluoromethyl)phenyl)ethanol (0.129 g, 0.6 mmol) and triphenylphosphine (0.274 g, 1.0 mmol) in THF (2 mL) cooled to 0° C. was added DIAD (0.3 mL, 1.6 mmol). The reaction solution was stirred at RT for 6 h. The resulting mixture was diluted with water (50 mL) and EtOAc (50 mL). The organic extract was washed with brine (50 mL), dried with anhydrous Na$_2$SO$_4$ and filtered. The filtrate was concentrated under vacuum. The residue was purified by silica gel chromatography (10% ethyl acetate in petroleum ether) to furnish the racemic title compounds. MS=398.2/400.2 (M+1).

Step 2. (R)- and (S)-6-(2-(1-(2-chloro-4-(trifluoromethyl)phenyl)ethyl)-2H-1,2,3-triazol-4-yl)-2-methylpyrimidin-4(3H)-one A solution of 4-(2-(1-(2-chloro-4-(trifluoromethyl)phenyl)ethyl)-2H-1,2,3-triazol-4-yl)-6-methoxy-2-methylpyrimidine (80.0 mg, 0.2 mmol) in HCl (saturated in EtOAc, 2 mL) was stirred at 90° C. for 4 h. The resulting mixture was cooled to RT and diluted with saturated NaHCO$_3$ solution (30 mL) and EtOAc (30 mL). The organic extract was dried with anhydrous Na$_2$SO$_4$ and filtered. The filtrate was concentrated under vacuum. The residue was purified by silica gel chromatography (50% ethyl acetate in petroleum ether) to furnish the racemic title compound. The enantiopure title compounds were resolved by Chiral HPLC (Phenomenex Lux 5 u Cellulose-4 column; 20% ethanol in hexanes). The faster-eluting enantiomer of the title compound was obtained as a solid (Example 1): $^1$H NMR (300 MHz, CDCl$_3$) δ: 12.90 (br, 1H), 8.18 (s, 1H), 7.68 (s, 1H), 7.47 (d, J=8.1 Hz, 1H), 7.24 (d, J=8.1 Hz, 1H), 6.95 (s, 1H), 6.41 (q, J=7.2 Hz, 1H), 2.57 (s, 3H), 2.01 (d, J=7.2 Hz, 3H). MS=384.1/386.1 (M+1). The slower-eluting enantiomer of the title compound was obtained as a solid (Example 2): $^1$H NMR (300 MHz, CDCl$_3$) δ: 12.70 (br, 1H), 8.20 (s, 1H), 7.68 (s, 1H), 7.47 (d, J=8.7 Hz, 1H), 7.24 (d, J=8.7 Hz, 1H), 6.91 (s, 1H), 6.41 (q, J=7.2 Hz, 1H), 2.57 (s, 3H), 2.01 (d, J=7.2 Hz, 3H). MS=384.0/386.1 (M+1).

TABLE 6

The following compounds were prepared using procedures similar to those described for Examples 1 and 2 using the appropriate starting materials. Racemic products were separated using chiral columns specified in the table. For those pairs of enantiomers, the fast-eluting isomer is listed first. This convention for listing enantiomers from chiral HPLC separations will be used in all the subsequent tables. Where an "*" appears in any structure in a table it is intended to indicate a single stereoisomer where the absolute stereochemistry has not been determined.

| Example No. | Structure | IUPAC Name | Exact Mass [M + H]⁺ | Chiral column |
|---|---|---|---|---|
| 3 | 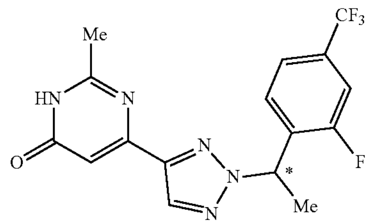 [SMILES: Cc1nc(-c2cnn(C(C)c3ccc(C(F)(F)F)cc3F)n2)cc(=O)[nH]1] | (R)- or (S)-6-(2-(1-(2-fluoro-4-(trifluoromethyl)phenyl)ethyl)-2H-1,2,3-triazol-4-yl)-2-metylpyrimidin-4(3H)-one | Calc'd 368.1, found 368.1 | Lux Cellulose-4 |
| 4 | 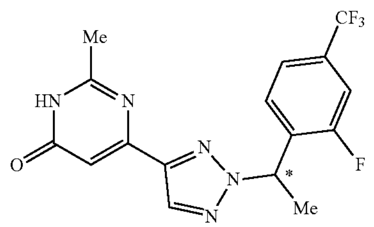 [SMILES: Cc1nc(-c2cnn(C(C)c3ccc(C(F)(F)F)cc3F)n2)cc(=O)[nH]1] | (S)- or (R)-6-(2-(1-(2-fluoro-4-(trifluoromethyl)phenyl)ethyl)-2H-1,2,3-triazol-4-yl)-2-metylpyrimidin-4(3H)-one | Calc'd 368.1, found 368.1 | Lux Cellulose-4 |
| 5 | 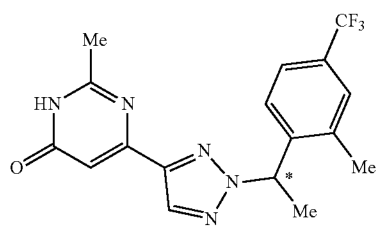 [SMILES: Cc1nc(-c2cnn(C(C)c3ccc(C(F)(F)F)cc3C)n2)cc(=O)[nH]1] | (R)- or (S)-2-methyl-6-(2-(1-(2-methyl-4-(trifluoromethyl)phenyl)ethyl)-2H-1,2,3-triazol-4-yl)pyrimidin-4(3H)-one | Calc'd 364.1, found 364.0 | (R,R)WHE LK-01 |
| 6 | 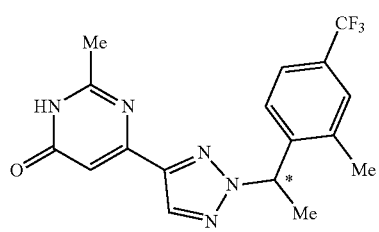 [SMILES: Cc1nc(-c2cnn(C(C)c3ccc(C(F)(F)F)cc3C)n2)cc(=O)[nH]1] | (S)- or (R)-2-methyl-6-(2-(1-(2-methyl-4-(trifluoromethyl)phenyl)ethyl)-2H-1,2,3-triazol-4-yl)pyrimidin-4(3H)-one | Calc'd 364.1, found 363.9 | (R,R)WHE LK-01 |
| 7 | 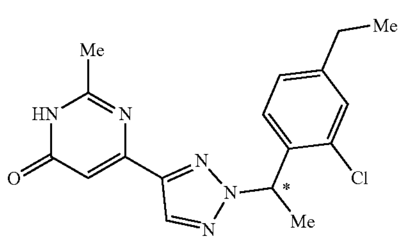 [SMILES: CCc1ccc(C(C)n2ncc(-c3cc(=O)[nH]c(C)n3)n2)c(Cl)c1] | (R)- or (S)-6-(2-(1-(2-chloro-4-ethylphenyl)ethyl)-2H-1,2,3-triazol-4-yl)-2-methylpyrimidin-4(3H)-one | Calc'd 344.1, found 344.0 | (R,R)WHE LK-01 |
| 8 | 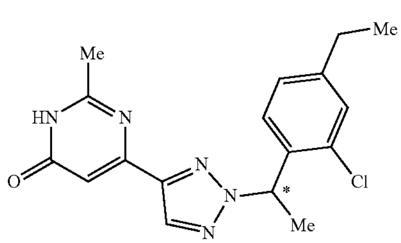 [SMILES: CCc1ccc(C(C)n2ncc(-c3cc(=O)[nH]c(C)n3)n2)c(Cl)c1] | (S)- or (R)-6-(2-(1-(2-chloro-4-ethylphenyl)ethyl)-2H-1,2,3-triazol-4-yl)-2-methylpyrimidin-4(3H)-one | Calc'd 344.1, found 344.0 | (R,R)WHE LK-01 |

Examples 9 and 10

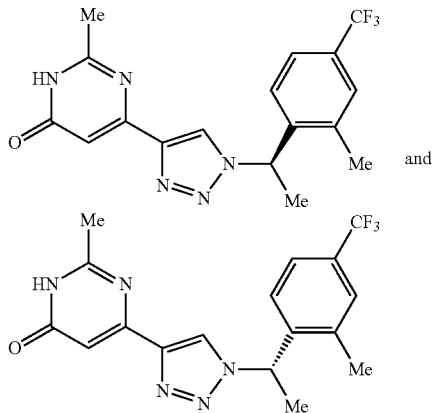

(R)- and (S)-2-methyl-6-(1-(1-(2-methyl-4-(trifluoromethyl)phenyl)-ethyl)-1H-1,2,3-triazol-4-yl)pyrimidin-4(3H)-one (Scheme 12)

Step 1. 4-Methoxy-2-methyl-6-(1-(1-(2-methyl-4-(trifluoromethyl)phenyl)ethyl)-1H-1,2,3-triazol-4-yl)pyrimidine To a solution of 1-(1-azidoethyl)-2-methyl-4-(trifluoromethyl)benzene (0.224 g, 1.0 mmol) in acetonitrile (1 mL) were added $CuSO_4 \cdot 5H_2O$ (0.244 g, 1.0 mmol), copper (63.0 mg, 1.0 mmol), 4-ethynyl-6-methoxy-2-methylpyrimidine (0.145 g, 1.0 mmol) and $Na_2CO_3$ (1 mL, 2 M in water). The reaction mixture was stirred at RT for 16 h in air. The resulting mixture was concentrated under reduced pressure. The residue was diluted with EtOAc (40 mL), washed with water (2×10 mL) and brine (10 mL). The separated organic layer was dried with anhydrous $Na_2SO_4$ and filtered. The filtrate was concentrated under reduced pressure. The residue was purified by silica gel chromatography (0-40% ethyl acetate in petroleum ether) to afford the title compound as a solid. MS=378.1 (M+1).

Step 2. (R)- and (S)-2-methyl-6-(1-(1-(2-methyl-4-(trifluoromethyl)phenyl)ethyl)-1H-1,2,3-triazol-4-yl)pyrimidin-4(3H)-one To a solution of 4-methoxy-2-methyl-6-(1-(1-(2-methyl-4-(trifluoromethyl)phenyl)ethyl)-1H-1,2,3-triazol-4-yl)pyrimidine (0.180 g, 0.5 mmol) in acetonitrile (8 mL) were added NaI (0.286 g, 1.9 mmol) and TMSCl (0.207 g, 1.9 mmol). The reaction solution was stirred at 70° C. for 2.5 h. The resulting mixture was cooled to RT and concentrated under reduced pressure. The residue was diluted with EtOAc (40 mL), washed with water (2×10 mL) and then washed with brine (10 mL). The organic extract was dried with anhydrous $Na_2SO_4$ and filtered. The filtrate was concentrated under reduced pressure. The residue was purified by Prep-HPLC (Column, X Select $C^{18}$; 32-47% acetonitrile in water+0.05% TFA) to furnish the racemic title compound. The racemic title compound was resolved by chiral HPLC (Chiralpak IA; 10% ethanol in hexanes) to furnish the enantiopure compounds. The faster-eluting enantiomer of the title compound was obtained as a solid (Example 9): $^1$H NMR (400 MHz, DMSO-$d_6$) δ: 12.46 (br, 1H), 8.71 (s, 1H), 7.62-7.58 (m, 2H), 7.46-7.44 (m, 1H), 6.70 (s, 1H), 6.28 (q, J=7.2 Hz, 1H), 2.48 (s, 3H), 2.33 (s, 3H), 1.93 (d, J=7.2 Hz, 3H). MS=364.2 (M+1). The slower-eluting enantiomer of the title compound was obtained as a solid (Example 10): $^1$H NMR (400 MHz, DMSO-$d_6$) δ: 12.48 (br, 1H), 8.71 (s, 1H), 7.62-7.58 (m, 2H), 7.46-7.44 (m, 1H), 6.70 (s, 1H), 6.28 (q, J=7.2 Hz, 1H), 2.48 (s, 3H), 2.33 (s, 3H), 1.93 (d, J=7.2 Hz, 3H). MS=364.2 (M+1).

TABLE 7

The following compounds were prepared using procedures similar to those described for Examples 9 and 10 using the appropriate starting materials.

| Example No. | Structure | IUPAC Name | Exact Mass [M + H]$^+$ |
| --- | --- | --- | --- |
| 11 | 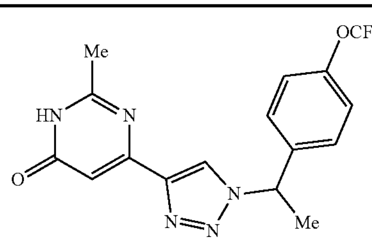 | 2-methyl-6-(1-(1-(4-(trifluoromethoxy)phenyl)ethyl)-1H-1,2,3-triazol-4-yl)pyrimidin-4(3H)-one | Calc'd 366.1, found 366.2 |
| 12 | 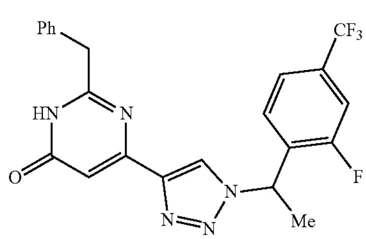 [SMILES: CC(c1ccc(C(F)(F)F)cc1F)n1cc(-c2cc(=O)[nH]c(Cc3ccccc3)n2)nn1] | 2-benzyl-6-(1-(1-(2-fluoro-4-(trifluoromethyl)phenyl)ethyl-1H-1,2,3-triazol-4-yl)pyrimidin-4(3H)-one | Calc'd 444.1, found 444.1 |

TABLE 7-continued

The following compounds were prepared using procedures similar to those described for Examples 9 and 10 using the appropriate starting materials.

| Example No. | Structure | IUPAC Name | Exact Mass [M + H]+ |
|---|---|---|---|
| 13 | 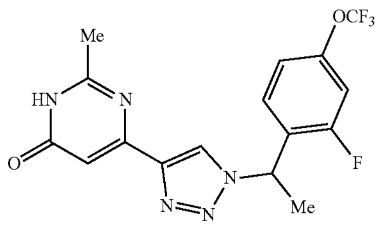 [SMILES: Cc1nc(-c2cn(C(C)c3ccc(OC(F)(F)F)cc3F)nn2)cc(=O)[nH]1] | 6-(1-(1-(2-fluoro-4-(trifluoromethoxy)phenyl)ethyl)-1H-1,2,3-triazol-4-yl)-2-methylpyrimidin-4(3H)-one | Calc'd 384.1, found 384.1 |
| 14 | 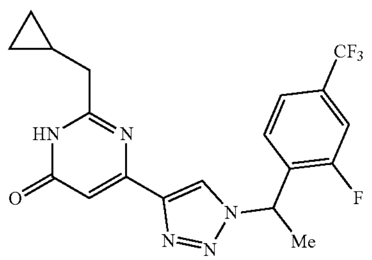 [SMILES: CC(c1ccc(C(F)(F)F)cc1F)n1cc(-c2cc(=O)[nH]c(CC3CC3)n2)nn1] | 2-(cyclopropylmethyl)-6-(1-(1-(2-fluoro-4-(trifluoromethyl)phenyl)ethyl)-1H-1,2,3-triazol-4-yl)pyrimidin-4(3H)-one | Calc'd 408.1, found 408.1 |
| 15 | 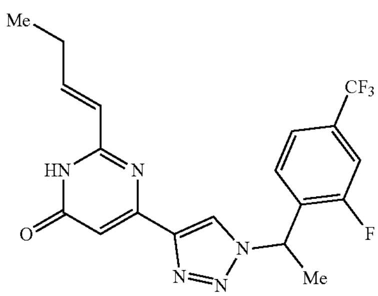 [SMILES: CC/C=C/c1nc(-c2cn(C(C)c3ccc(C(F)(F)F)cc3F)nn2)cc(=O)[nH]1] | (E)-2-(but-1-enyl)-6-(1-(1-(2-fluoro-4-(trifluoromethyl)phenyl)ethyl)-1H-1,2,3-triazol-4-yl)pyrimidin-4(3H)-one | Calc'd 408.1, found 408.1 |
| 16 | 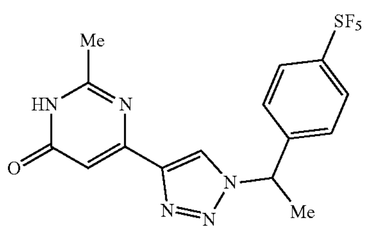 [SMILES: Cc1nc(-c2cn(C(C)c3ccc(C(F)(F)F)cc3)nn2)cc(=O)[nH]1] | 2-methyl-6-(1-(1-(4-(pentafluorosulfanyl)phenyl)ethyl)-1H-1,2,3-triazol-4-yl)pyrimidin-4(3H)-one | Calc'd 408.1, found 408.1 |

TABLE 8

The following compounds were prepared using preocedures similar to those described for examples 9 and 10 using the appropriate starting materials. Racemic products were separated using the chiral columns specified in the table.

| Example No. | Structure | IUPAC Name | Exact Mass [M + H]+ | Chiral column |
|---|---|---|---|---|
| 17 | 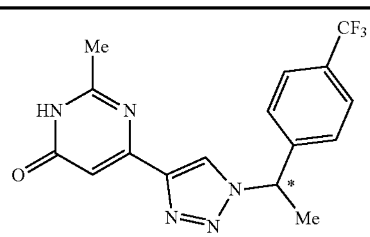 | (R)- or (S)-2-methyl-6-(1-(1-(4-(trifluoromethyl)phenyl)ethyl)-1H-1,2,3-triazol-4-yl)pyrimidin-4(3H)-one | Calc'd 350.1, found 350.2 | CHIRAL PAK IC |

TABLE 8-continued

The following compounds were prepared using preocedures similar to those described for examples 9 and 10 using the appropriate starting materials. Racemic products were separated using the chiral columns specified in the table.

| Example No. | Structure | IUPAC Name | Exact Mass [M + H]+ | Chiral column |
|---|---|---|---|---|
| 18 | 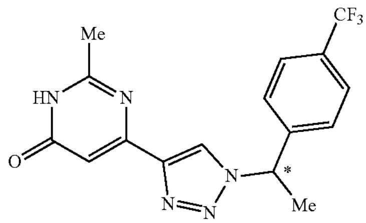 [SMILES: Cc1nc(-c2cn(C(C)c3ccc(C(F)(F)F)cc3)nn2)cc(=O)[nH]1] | (S)- or (R)-2-methyl-6-(1-(1-(4-(trifluoromethyl)phenyl)ethyl)-1H-1,2,3-triazol-4-yl)pyrimidin-4(3H)-one | Calc'd 350.1, found 350.2 | CHIRAL PAK IC |
| 19 | 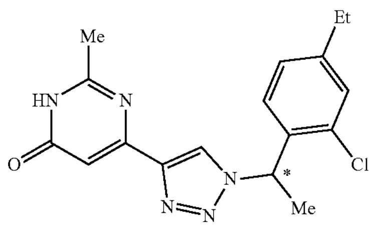 [SMILES: CCc1ccc(C(C)n2cc(-c3cc(=O)[nH]c(C)n3)nn2)c(Cl)c1] | (R)- or (S)-6-(1-(1-(2-chloro-4-ethylphenyl)ethyl)-1H-1,2,3-triazol-4-yl)-2-methylpyrimidin-4(3H)-one | Calc'd 344.1/346.1, found 344.2/346.2 | CHIRAL CEL OJ-H |
| 20 | 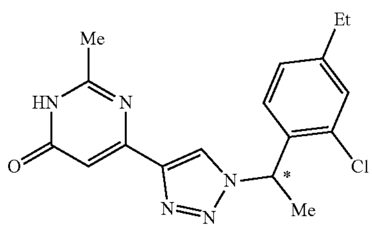 [SMILES: CCc1ccc(C(C)n2cc(-c3cc(=O)[nH]c(C)n3)nn2)c(Cl)c1] | (S)- or (R)-6-(1-(1-(2-chloro-4-ethylphenyl)ethyl)-1H-1,2,3-triazol-4-yl)-2-methylpyrimidin-4(3H)-one | Calc'd 344.1, found 344.1/346.2 | CHIRAL CEL OJ-H |
| 21 | 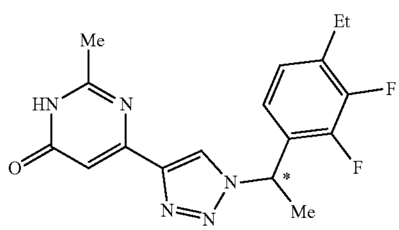 [SMILES: CCc1ccc(C(C)n2cc(-c3cc(=O)[nH]c(C)n3)nn2)c(F)c1F] | (R)- or (S)-6-(1-(1-(2,3-difluoro-4-(trifluoromethyl)phenyl)ethyl)-1H-1,2,3-triazol-4-yl)-2-methylpyrimidin-4(3H)-one | Calc'd 386.1, found 386.0 | (R,R) WHELK-01 |
| 22 | 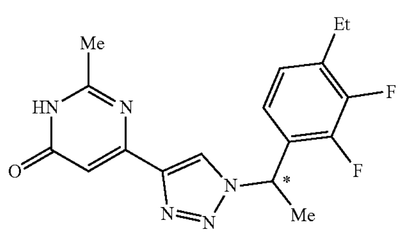 [SMILES: CCc1ccc(C(C)n2cc(-c3cc(=O)[nH]c(C)n3)nn2)c(F)c1F] | (S)- or (R)-6-(1-(1-(2,3-difluoro-4-(trifluoromethyl)phenyl)ethyl)-1H-1,2,3-triazol-4-yl)-2-methylpyrimidin-4(3H)-one | Calc'd 386.1, found 386.0 | (R,R) WHELK-01 |
| 23 | 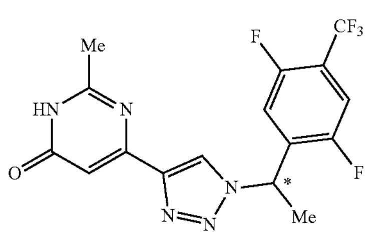 [SMILES: Cc1nc(-c2cn(C(C)c3cc(F)c(C(F)(F)F)cc3F)nn2)cc(=O)[nH]1] | (R)- or (S)-6-(1-(1-(2,5-difluoro-4-(triufluoromethyl)phenyl)ethyl)-1H-1,2,3-triazol-4-yl)-2-methylpyrimidin-4(3H)-one | Calc'd 386.1, found 386.0 | (R,R) WHELK-01 |

TABLE 8-continued

The following compounds were prepared using preocedures similar to those described for examples 9 and 10 using the appropriate starting materials. Racemic products were separated using the chiral columns specified in the table.

| Example No. | Structure | IUPAC Name | Exact Mass [M + H]+ | Chiral column |
|---|---|---|---|---|
| 24 | 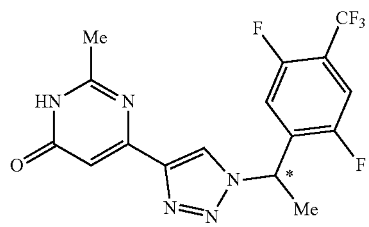 [SMILES: Cc1nc(-c2cn(C(C)c3cc(F)c(C(F)(F)F)cc3F)nn2)cc(=O)[nH]1] | (S)- or (R)-6-(1-(1-(2,5-difluoro-4-(triufluoromethyl)phenyl)ethyl)-1H-1,2,3-triazol-4-yl)-2-methylpyrimidin-4(3H)-one | Calc'd 386.1, found 386.0 | (R,R) WHELK-01 |
| 25 | 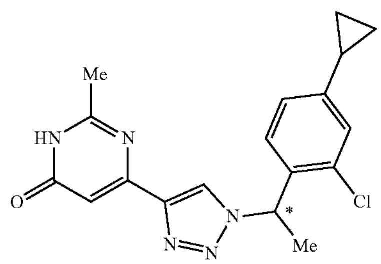 [SMILES: Cc1nc(-c2cn(C(C)c3ccc(C4CC4)cc3Cl)nn2)cc(=O)[nH]1] | (R)- or (S)-6-(1-(1-(2-chloro-4-cyclopropylphenyl)ethyl)-1H-1,2,3-triazol-4-yl)-2-methylpyrimidin-4(3H)-one | Calc'd 356.1, found 356.0 | Lux-Cellulose-4 |
| 26 | 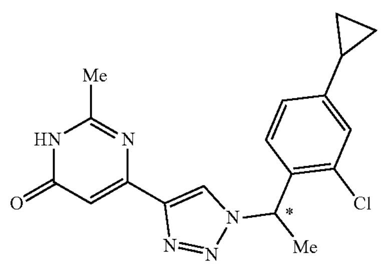 [SMILES: Cc1nc(-c2cn(C(C)c3ccc(C4CC4)cc3Cl)nn2)cc(=O)[nH]1] | (S)- or (R)-6-(1-(1-(2-chloro-4-cyclopropylphenyl)ethyl)-1H-1,2,3-triazol-4-yl)-2-methylpyrimidin-4(3H)-one | Calc'd 356.1, found 356.1 | Lux-Cellulose-4 |
| 27 | 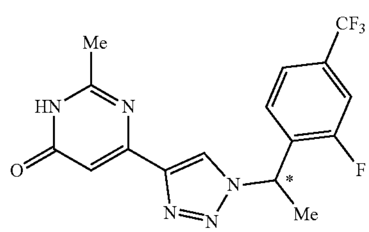 [SMILES: Cc1nc(-c2cn(C(C)c3ccc(C(F)(F)F)cc3F)nn2)cc(=O)[nH]1] | (R)- or (S)-6-(1-(1-(2-fluoro-4-(trifluoromethyl)phenyl)ethyl)-1H-1,2,3-triazol-4-yl)-2-methylpyrimidin-4(3H)-one | Calc'd 368.1, found 367.9 | Chiralpak OZ-H |
| 28 | 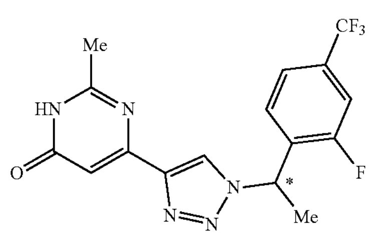 [SMILES: Cc1nc(-c2cn(C(C)c3ccc(C(F)(F)F)cc3F)nn2)cc(=O)[nH]1] | (S)- or (R)-6-(1-(1-(2-fluoro-4-(trifluoromethyl)phenyl)ethyl)-1H-1,2,3-triazol-4-yl)-2-methylpyrimidin-4(3H)-one | Calc'd 368.1, found 367.9 | Chiralpak OZ-H |

Example 29

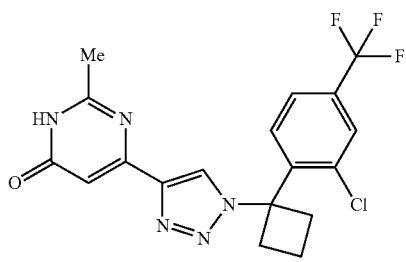 [SMILES: Cc1nc(-c2cn(C3(c4ccc(C(F)(F)F)cc4Cl)CCC3)nn2)cc(=O)[nH]1]

6-(1-(1-(2-Chloro-4-(trifluoromethyl)phenyl)cyclobutyl)-1H-1,2,3-triazol-4-yl)-2-methylpyrimidin-4(3H)-one (Scheme 12)

Step 1. 4-(1-(1-(2-Chloro-4-(trifluoromethyl)phenyl)cyclobutyl)-1H-1,2,3-triazol-4-yl)-6-methoxy-2-methylpyrimidine A procedure similar to step 1 in the synthesis of Examples 9 and 10 starting with 4-ethynyl-6-methoxy-2-methylpyrimidine (6.5 mg, 0.04 mmol) and 1-(1-azido-cyclobutyl)-2-chloro-4-(trifluoromethyl)benzene (15.0 mg, 0.04 mmol) was employed. MS=424.1/426.1 (M+1).

Step 2. 6-(1-(1-(2-Chloro-4-(trifluoromethyl)phenyl)cyclobutyl)-1H-1,2,3-triazol-4-yl)-2-methylpyrimidin-4(3H)-one To a solution of 4-(1-(1-(2-chloro-4-(trifluoromethyl)phenyl)cyclobutyl)-1H-1,2,3-triazol-4-yl)-6-methoxy-2-methylpyrimidine (30.0 mg, 0.1 mmol) in DMSO (2.0 mL) was added NaCN (10.4 mg, 0.2 mmol) at RT. The reaction solution was stirred at 120° C. for 2 h. The resulting solution was cooled, diluted with water (100 mL) and extracted with EtOAc (3×30 mL). The combined organic extracts were washed with brine (50 mL), dried with anhydrous $Na_2SO_4$ and filtered. The filtrate was concentrated under reduced pressure. The residue was purified by preparative HPLC (XBridge C18 column 35-63% acetonitrile in water+10 mM $NH_4HCO_3$) to provide the title compound. $^1$H NMR (400 MHz, DMSO-$d_6$) δ: 8.66 (s, 1H), 8.06 (d, J=8.4 Hz, 1H), 7.87-7.86 (m, 2H), 6.69 (s, 1H), 3.22-3.17 (m, 2H), 3.11-3.05 (m, 2H), 2.32 (s, 3H), 2.19-2.08 (m, 1H), 1.98-1.87 (m, 1H). MS=410.0/412.0 (M+1).

TABLE 9

The following compounds were prepared using procedures similar to those described for Example 29 using the appropriate starting materials.

| Example No. | Structure | IUPAC Name | Exact Mass [M + H] |
|---|---|---|---|
| 30 | 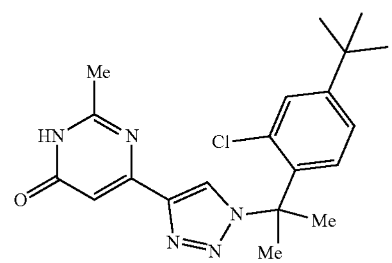 [SMILES: Cc1nc(-c2cn(C(C)(C)c3ccc(C(C)(C)C)cc3Cl)nn2)cc(=O)[nH]1] | 6-(1-(2-(2-chloro-4-(trifluoromethyl)phenyl)propan-2-yl)-1H-1,2,3-triazol-4-yl)-2-methylpyrimidin-4(3H)-one | Calc'd 398.1/400.1, found 398.0/400.0 |
| 31 | 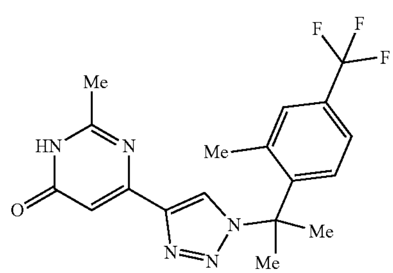 [SMILES: Cc1nc(-c2cn(C(C)(C)c3ccc(C(F)(F)F)cc3C)nn2)cc(=O)[nH]1] | 2-methyl-6-(1-(2-(2-methyl-4-(trifluoromethyl)phenyl)propan-2-yl)-1H-1,2,3-triazol-4-yl)pyrimidin-4(3H)-one | Calc'd 378.1, found 378.1 |
| 32 | 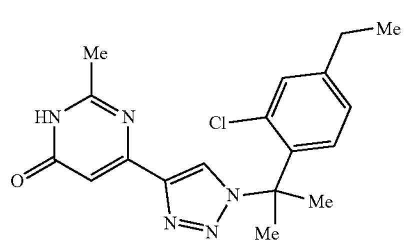 [SMILES: CCc1ccc(C(C)(C)n2cc(-c3cc(=O)[nH]c(C)n3)nn2)c(Cl)c1] | 6-(1-(2-(2-chloro-4-ethylphenyl)propan-2-yl)-1H-1,2,3-triazol-4-yl)-2-methylpyrimidin-4(3H)-one | Calc'd 358.1/360.1, found 358.0/360.1 |

TABLE 9-continued

The following compounds were prepared using procedures similar to those described for Example 29 using the appropriate starting materials.

| Example No. | Structure | IUPAC Name | Exact Mass [M + H] |
|---|---|---|---|
| 33 | 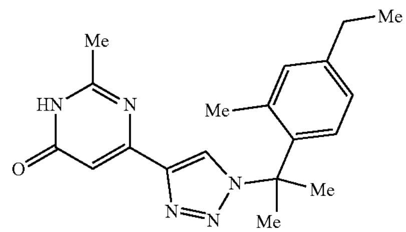 [SMILES: CCc1ccc(C(C)(C)n2cc(-c3cc(=O)[nH]c(C)n3)nn2)c(C)c1] | 6-(1-(2-(4-ethyl-2-methylphenyl)propan-2-yl)-1H-1,2,3-triazol-4-yl)-2-methylpyrimidin-4(3H)-one | Calc'd 338.2, found 338.1 |
| 34 | 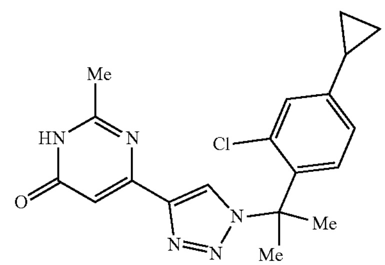 [SMILES: Cc1nc(-c2cn(C(C)(C)c3ccc(C4CC4)cc3Cl)nn2)cc(=O)[nH]1] | 6-(1-(2-(2-chloro-4-cyclopropylphenyl)propan-2-yl)-1H-1,2,3-triazol-4-yl)-2-methylpyrimdin-4(3H)-one | Calc'd 370.1/372.1, found 370.1/372.1 |

Examples 35 and 36

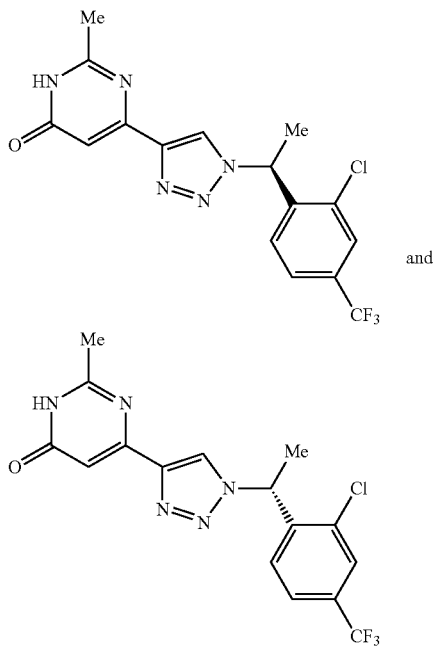

(R)- and (S)-6-(1-(1-(2-Chloro-4-(trifluoromethyl)phenyl)ethyl)-1H-1,2,3-triazol-4-yl)-2-methylpyrimidin-4(3H)-one (Scheme 12)

Step 1. 4-(1-(1-(2-Chloro-4-(trifluoromethyl)phenyl)ethyl)-1H-1,2,3-triazol-4-yl)-6-((4-methoxybenzyl)oxy)-2-methylpyrimidine A mixture of 4-ethynyl-6-((4-methoxybenzyl)oxy)-2-methylpyrimidine (560 mg, 2.203 mmol), 1-(1-azidoethyl)-2-chloro-4-(trifluoromethyl)benzene (500 mg, 2.003 mmol), cupric sulfate (63.9 mg, 0.401 mmol), copper (127 mg, 2.003 mmol), sodium carbonate (212 mg, 2.003 mmol) in toluene (4006 µl) was stirred at RT for 19 h. The mixture was diluted with EtOAc and brine. The organic extract was dried over $Na_2SO_4$, filtered, and concentrated. The residue was purified by silica gel chromatography (0-20% (3:1 EtOAc:EtOH) in hexanes). MS=504.0 (M+1).

Step 2. (R)- and (S)-6-(1-(1-(2-chloro-4-(trifluoromethyl)phenyl)ethyl)-1H-1,2,3-triazol-4-yl)-2-methylpyrimidin-4(3H)-one To a RT solution of 4-(1-(1-(2-chloro-4-(trifluoromethyl)phenyl)ethyl)-1H-1,2,3-triazol-4-yl)-6-((4-methoxybenzyl)oxy)-2-methylpyrimidine (214 mg, 0.314 mmol) in DCM (2.5 ml) was added trifluoroacetic acid (2.5 ml, 32.4 mmol) After 30 minutes, the reaction was concentrated, diluted with EtOAc, washed with saturated $NaHCO_3$ solution, dried over $Na_2SO_4$, and concentrated. The residue was purified by silica gel chromatography (0-30% (3:1 EtOAc:EtOH) in hexanes) to furnish the racemic title compound. The enantiopure title compounds were resolved by Chiral HPLC (Column: Chiralpak OZ; 40% MeOH in $CO_2$+0.1% diethylamine). The faster-eluting enantiomer of the title compound was obtained as a solid (Example 35): $^1$H NMR (300 MHz, $CDCl_3$) δ: 12.46 (broad s, 1H), 8.77 (s, 1H), 7.95 (s, 1H), 7.77 (d, J=8.0 Hz, 1H), 7.53 (d, J=8.0 Hz, 1H), 6.69 (s, 1H), 6.37 (q, J=8.0 Hz, 1H), 2.32 (s, 3H), 1.96 (d, J=8.0 Hz, 3H). MS=384.0/386.0 (M+1). The slower-eluting enantiomer of the title compound was obtained as a solid (Example 36): $^1$H NMR (500 MHz, DMSO-$d_6$) δ: 12.46 (broad s, 1H), 8.77 (s, 1H), 7.95 (s, 1H), 7.77 (d, J=8.0 Hz, 1H), 7.53 (d, J=8.0 Hz, 1H), 6.69 (s, 1H), 6.37 (q, J=8.0 Hz, 1H), 2.32 (s, 3H), 1.96 (d, J=8.0 Hz, 3H). MS=383.9/386.0 (M+1).

TABLE 10

The following compounds were prepared using procedures similar to those described for Examples 35 and 36 using the appropriate starting materials. Racemic products were separated using the chiral columns specified in the table.

| Example No. | Structure | IUPAC Name | Exact Mass [M + H]⁺ | Chiral column |
|---|---|---|---|---|
| 37 | 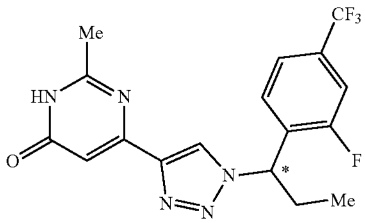 [SMILES: CCC(c1ccc(C(F)(F)F)cc1F)n1cc(-c2cc(=O)[nH]c(C)n2)nn1] | (R)- or (S)-6-(1-(1-(2-fluoro-4-(trifluoromethyl)phenyl)propyl-1H-1,2,3-triazol-4-yl)-2-methylpyrimidin-4(3H)-one | Calc'd 382.1, found 381.1 | Chiralpak IC |
| 38 | 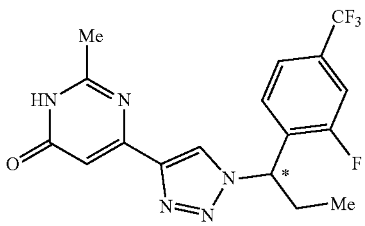 [SMILES: CCC(c1ccc(C(F)(F)F)cc1F)n1cc(-c2cc(=O)[nH]c(C)n2)nn1] | (S)- or (R)-6-(1-(1-(2-fluoro-4-(trifluoromethyl)phenyl)propyl)-1H-1,2,3-triazol-4-yl)-2-methylpyrimidin-4(3H)-one | Calc'd 382.1, found 381.9 | Chiralpak IC |
| 39 | 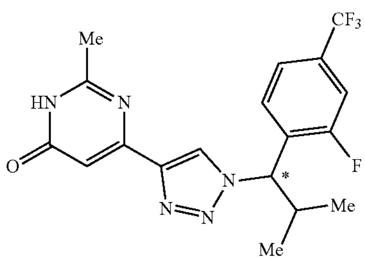 [SMILES: Cc1nc(-c2cn(C(c3ccc(C(F)(F)F)cc3F)C(C)C)nn2)cc(=O)[nH]1] | (R)- or (S)-6-(1-(1-(2-fluoro-4-(trifluoromethyl)phenyl)-2-methylpropyl)-1H-1,2,3-triazol-4-yl)-2-methylpyrimidin-4(3H)-one | Calc'd 396.1, found 395.9 | Chiralpak AD-H |
| 40 | 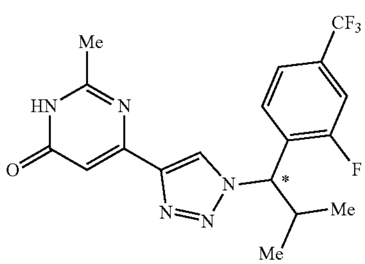 [SMILES: Cc1nc(-c2cn(C(c3ccc(C(F)(F)F)cc3F)C(C)C)nn2)cc(=O)[nH]1] | (S)- or (R)-6-(1-(1-(2-fluoro-4-(trifluoromethyl)phenyl)-2-methylpropyl)-1H-1,2,3-triazol-4-yl)-2-methylpyrimidin-4(3H)-one | Calc'd 396.1, found 395.9 | Chiralpak AD-H |

Examples 41 and 42

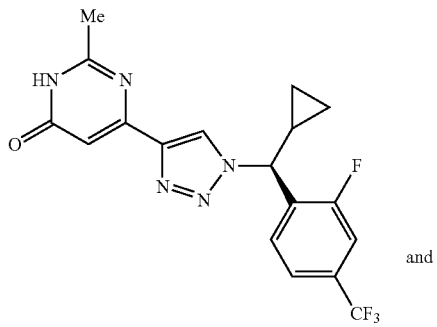

and

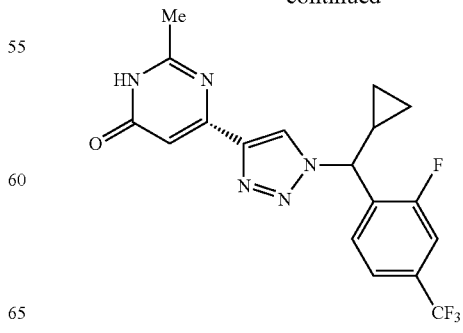

(R)- and (S)-6-(1-(Cyclopropyl(2-fluoro-4-(trifluoromethyl)phenyl)methyl)-1H-1,2,3-triazol-4-yl)-2-methylpyrimidin-4(3H)-one (Scheme 12)

Step 1. 4-(1-(Cyclopropyl(2-fluoro-4-(trifluoromethyl)phenyl)methyl)-1H-1,2,3-triazol-4-yl)-6-((4-methoxybenzyl)oxy)-2-methylpyrimidine A procedure similar to step 1 in the synthesis of examples 9 and 10 starting with 4-ethynyl-6-((4-methoxybenzyl)oxy)-2-methylpyrimidine (1036 mg, 4.07 mmol) and 1-(azido(cyclopropyl)methyl)-2-fluoro-4-(trifluoromethyl)benzene (960 mg, 3.70 mmol) was employed. MS=513.9 (M+1).

Step 2. (R)- or (S)-6-(1-(Cyclopropyl(2-fluoro-4-(trifluoromethyl)phenyl)methyl)-1H-1,2,3-triazol-4-yl)-2-methylpyrimidin-4(3H)-one To a solution of 4-(1-(cyclopropyl(2-fluoro-4-(trifluoromethyl)phenyl)methyl)-1H-1,2,3-triazol-4-yl)-6-((4-methoxybenzyl)oxy)-2-methylpyrimidine (304 mg, 0.592 mmol) in MeOH (5.842 mL) at RT was added Pd—C (63.0 mg, 0.059 mmol). The reaction vessel was evacuated and charged with hydrogen (1.193 mg, 0.592 mmol) via a balloon. After 1.5 h, the reaction was filtered over celite, washed with MeOH and concentrated. The residue was purified by silica gel chromatography (0-70% (3:1 EtOAc:EtOH) in hexanes) to provide the racemic title compound. The racemic title compound was separated by Chiral HPLC (CHIRAL PAK IC; 15% EtOH in CO$_2$+0.1% NH$_4$OH) to furnish the enantiopure title compounds. The faster-eluting enantiomer of the title compound was obtained as a solid (Example 41): $^1$H NMR (400 MHz, DMSO-d$_6$) δ: 12.45 (s, 1H), 8.81 (s, 1H), 7.90 (m, 1H), 7.74-7.68 (m, 2H), 6.68 (s, 1H), 5.43 (d, J=10.5 Hz, 1H), 2.32 (s, 3H), 2.00 (s, 1H), 0.74 (m, 2H), 0.54 (m, 1H), 0.53 (m, 1H). MS=393.9 (M+1). The slower-eluting enantiomer of the title compound was obtained as a solid (Example 42): $^1$H NMR (400 MHz, DMSO-d$_6$) δ: 12.45 (s, 1H), 8.81 (s, 1H), 7.90 (m, 1H), 7.74-7.68 (m, 2H), 6.68 (s, 1H), 5.43 (d, J=10.5 Hz, 1H), 2.32 (s, 3H), 2.01 (s, 1H), 0.73 (m, 2H), 0.54 (m, 1H), 0.53 (m, 1H). MS=393.9 (M+1).

Examples 43 and 44

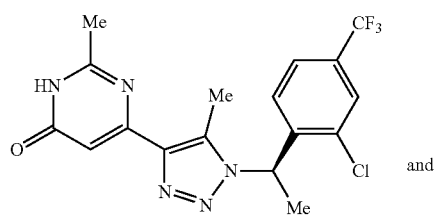

and

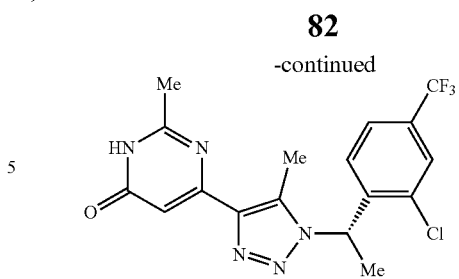

(R)- and (S)-6-(1-(1-(2-Chloro-4-(trifluoromethyl)phenyl)-ethyl)-5-methyl-1H-1,2,3-triazol-4-yl)-2-methylpyrimidin-4(3H)-one (Scheme 12)

(R)- and (S)-6-(1-(1-(2-Chloro-4-(trifluoromethyl)phenyl)ethyl)-5-methyl-1H-1,2,3-triazol-4-yl)-2-methylpyrimidin-4(3H)-one 4-((4-methoxybenzyl)oxy)-2-methyl-6-(prop-1-yn-1-yl)pyrimidine (145 mg, 0.540 mmol), 1-(1-azidoethyl)-2-chloro-4-(trifluoromethyl)benzene (133 mg, 0.533 mmol), and chloro(pentamethylcyclopentadienyl)bis(triphenylphosphine)ruthenium(II) (42.4 mg, 0.053 mmol) were combined in toluene (2.5 ml) and heated to 80° C. overnight. The reaction was cooled to RT and directly purified by silica gel chromatography (ISCO 24 g silica cartridge; 0-25% ethyl acetate in hexanes). The product-containing fractions were concentrated and the residue was dissolved in dichloromethane (1.5 ml) and TFA (1.5 ml). After 10 minutes the reaction was concentrated and the residue was purified by reverse phase chromatography (Biotage 30 g C-18 cartridge; 10-90% acetonitrile in water+0.05% TFA). The product containing fractions were concentrated and the residue was partitioned between DCM and saturated NaHCO$_3$. The organic extract was dried over Na$_2$SO$_4$, filtered, and concentrated. The racemic title compound was separated by chiral chromatography (AS-H column; 10% MeOH in CO$_2$) to furnish the enantiopure title compounds. The faster-eluting enantiomer of the title compound (Example 43): $^1$H NMR (500 MHz, CDCl$_3$) δ: 7.71 (s, 1H), 7.51 (d, J=8.5 Hz, 1H), 7.28 (d, J=8.5 Hz, 1H), 7.23 (s, 1H), 6.05 (q, J=7 Hz, 1H), 5.33 (s, 1H), 2.60 (s, 3H), 2.55 (s, 3H), 2.11 (d, J=7 Hz, 3H). MS=397.8 (M+1). The slower-eluting enantiomer of the title compound (Example 44): $^1$H NMR (500 MHz, CDCl$_3$) δ: 7.71 (s, 1H), 7.51 (d, J=8.5 Hz, 1H), 7.28 (d, J=8.5 Hz, 1H), 7.23 (s, 1H), 6.05 (q, J=7 Hz, 1H), 5.33 (s, 1H), 2.60 (s, 3H), 2.55 (s, 3H), 2.11 (d, J=7 Hz, 3H). MS=397.8 (M+1).

TABLE 11

The following compounds were prepared using procedures similar to those described for examples 43 and 44 using the appropriate starting materials.

| Example No. | Structure | IUPAC Name | Exact Mass [M + H]⁺ | Chiral Column |
|---|---|---|---|---|
| 45 | 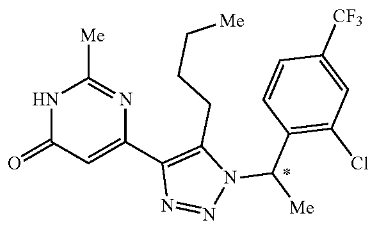 [SMILES: CCCCc1c(-c2cc(=O)[nH]c(C)n2)nnn1C(C)c1ccc(C(F)(F)F)cc1Cl] | (R)- or (S)-6-(5-butyl-1-(1-(2-chloro-4-(trifluoromethyl)phenyl)ethyl)-1H-1,2,3-triazol-4-yl)-2-methylpyrimidin-4(3H)-one | Calc'd 439.1, found 439.8 | Chiralpak IC |
| 46 | 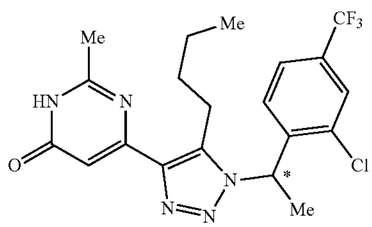 [SMILES: CCCCc1c(-c2cc(=O)[nH]c(C)n2)nnn1C(C)c1ccc(C(F)(F)F)cc1Cl] | (S)- or (R)-6-(5-butyl-1-(1-(2-chloro-4-(trifluoromethyl)phenyl)ethyl)-1H-1,2,3-triazol-4-yl)-2-methylpyrimidin-4(3H)-one | Calc'd 439.1, found 439.8 | Chiralpak IC |

Examples 47 and 48

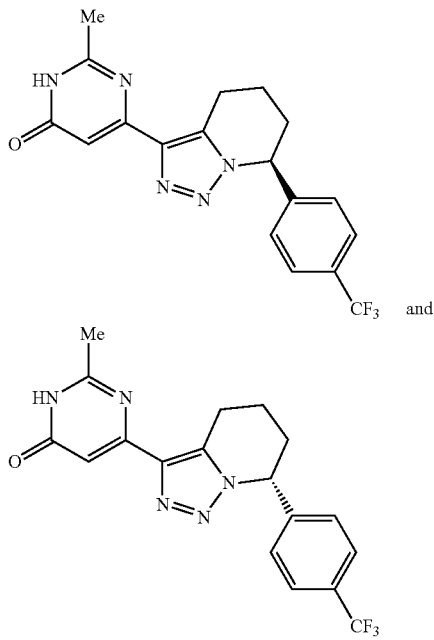

and (R)- and (S)-2-Methyl-6-(7-(4-(trifluoromethyl)phenyl)-4,5,6,7-tetrahydro-[1,2,3]triazolo[1,5-a]pyridin-3-yl)pyrimidin-4(3H)-one (Scheme 13)

Step 1. 6-(6-((4-Methoxybenzyl)oxy)-2-methylpyrimidin-4-yl)hex-5-yn-1-ol

A solution of 4-chloro-6-((4-methoxybenzyl)oxy)-2-methylpyrimidine (3.0 g, 11.33 mmol), hex-5-yn-1-ol (2.500 ml, 22.67 mmol), and triethylamine (4.74 ml, 34.0 mmol) in THF (20 ml) was degassed with nitrogen for 5 minutes. Then bis(triphenylphosphine)palladium(II) chloride (0.636 g, 0.907 mmol) and copper(I) iodide (0.259 g, 1.360 mmol) were added and the reaction was heated to 65° C. overnight. The reaction mixture was cooled to RT and concentrated. The residue was then purified by silica gel chromatography (0-80% ethyl acetate in hexanes) to furnish the title compound. MS=327.0 (M+1).

Step 2. 6-(6-((4-Methoxybenzyl)oxy)-2-methylpyrimidin-4-yl)hex-5-ynal

Dess-Martin periodinane (2.183 g, 5.15 mmol) was added to a solution of 6-(6-((4-methoxybenzyl)oxy)-2-methylpyrimidin-4-yl)hex-5-yn-1-ol (1.40 g, 4.29 mmol) and NaHCO₃ (1.802 g, 21.45 mmol) in dichloromethane (10 ml) cooled to 0° C. The reaction was allowed to warm to RT over 1 h. The reaction was filtered, concentrated, and purified by silica gel chromatography (0-80% ethyl acetate in hexanes) to furnish the title compound. MS=324.9 (M+1).

Step 3. 6-(6-((4-Methoxybenzyl)oxy)-2-methylpyrimidin-4-yl)-1-(4-(trifluoromethyl)-phenyl)hex-5-yn-1-ol n-hexyllithium (0.483 ml, 1.110 mmol) was added to a −78° C. solution of 1-bromo-4-(trifluoromethyl)benzene (0.168 ml, 1.202 mmol) in THF (3 ml). The mixture was warmed to −40° C. and stirred for 1 h at this temperature. The resulting solution was then cooled to −78° C. and cannulated into a flask containing a stirring solution of 6-(6-((4-methoxybenzyl)oxy)-2-methylpyrimidin-4-yl)hex-5-ynal (300 mg, 0.925 mmol) in THF (3 ml) cooled to −40° C. The reaction was quenched with saturated NH₄Cl solution and the product was extracted with ethyl acetate. The organic extract was dried over Na₂SO₄, filtered, and concentrated. The residue was purified by silica gel chromatography (0-70% ethyl acetate in hexanes) to furnish the title compound. ¹H NMR (500 MHz, CDCl₃) δ: 7.62 (d, J=8 Hz, 2H), 7.50 (d, J=8 Hz, 2H), 7.39 (d, J=8.5 Hz, 2H), 6.93 (d, J=8.5 Hz, 2H), 6.58 (s, 1H), 5.36 (s, 2H), 4.84 (dd, J=7 Hz, J=5.5 Hz, 1H), 3.84 (s, 3H), 2.66 (m, 1H), 2.62 (s, 3H), 2.54 (m, 1H), 2.52-2.48 (m, 2H), 2.07 (s, 3H), 1.98-1.88 (m, 2H).

Step 4. 4-(4-(6-((4-Methoxybenzyl)oxy)-2-methyl-pyrimidin-4-yl)-1H-1,2,3-triazol-5-yl)-1-(4-(trifluoromethyl)phenyl)butan-1-ol 6-(6-((4-methoxybenzyl)oxy)-2-methylpyrimidin-4-yl)-1-(4-(trifluoromethyl)phenyl)hex-5-yn-1-ol (89 mg, 0.189 mmol) and sodium azide (21 mg, 0.323 mmol) were combined in DMA (0.7 ml) and heated to 80° C. overnight. The reaction was diluted with ethyl acetate and the organic layer was washed with saturated NaHCO₃ solution and then with brine. The organic extract was dried over Na₂SO₄, filtered, and concentrated. The residue was then purified by silica gel chromatography (ISCO 12 g silica cartridge; 10-75% (3:1 EA:EtOH) in hexanes) to furnish the title compound. MS=513.9 (M+1).

Step 5. 2-Methyl-6-(7-(4-(trifluoromethyl)phenyl)-4,5,6,7-tetrahydro[1,2,3]triazolo-[1,5-a]pyridin-3-yl)pyrimidin-4(3H)-one Diisopropyl azodicarboxylate (0.020 ml, 0.102 mmol) was added to a solution of 4-(4-(6-((4-methoxybenzyl)oxy)-2-methylpyrimidin-4-yl)-1H-1,2,3-triazol-5-yl)-1-(4-(trifluoromethyl)-phenyl)butan-1-ol (35 mg, 0.068 mmol) and triphenylphosphine (26.8 mg, 0.102 mmol) in THF (0.9 ml) cooled to 0° C. The reaction was stirred for 5 minutes and then concentrated and purified by silica gel chromatography (ISCO 12 g silica cartridge; 0-40% ethyl acetate in hexanes). The product-containing fractions were concentrated and the residue was dissolved in dichloromethane (1 ml) and TFA (1 ml). The reaction was concentrated after 10 minutes and the residue was purified by reverse phase chromatography (Biotage 30 g C-18 cartridge; 10-90% ACN in water+0.05% TFA) to provide the title compound. The racemic title compound was separated by chiral chromatography (Chiralpak IC column; 60% MeOH in CO₂+0.2% NH₄OH) to furnish the enantiopure compounds. The faster-eluting enantiomer of the title compound (Example 47): ¹H NMR (500 MHz, CDCl₃) δ: 13.2-12.5 (broad, 1H), 7.64 (d, J=7.5 Hz, 2H), 7.21 (s, 1H), 7.12 (d, J=7.5 Hz, 2H), 5.83 (dd, J=5 Hz, J=5 Hz, 1H), 3.50-3.44 (m, 1H), 3.36-3.30 (m, 1H), 2.59 (s, 3H), 2.51-2.46 (m, 1H), 2.24-2.21 (m, 1H), 1.97-1.86 (m, 2H). MS=375.89 (M+1). The slower-eluting enantiomer of the title compound (Example 48): ¹H NMR (500 MHz, CDCl₃) δ: 13.2-12.5 (broad, 1H), 7.64 (d, J=7.5 Hz, 2H), 7.21 (s, 1H), 7.12 (d, J=7.5 Hz, 2H), 5.88 (dd, J=5 Hz, J=5 Hz, 1H), 3.50-3.44 (m, 1H), 3.36-3.30 (m, 1H), 2.59 (s, 3H), 2.51-2.46 (m, 1H), 2.24-2.21 (m, 1H), 1.97-1.86 (m, 2H). MS=375.89 (M+1).

TABLE 12

The following compounds were prepared using procedures similar to those described for Examples 47 and 48 using the appropriate starting materials.

| Example No. | Structure | IUPAC name | Exact Mass [M + H]+ | Chiral Column |
| --- | --- | --- | --- | --- |
| 49 | 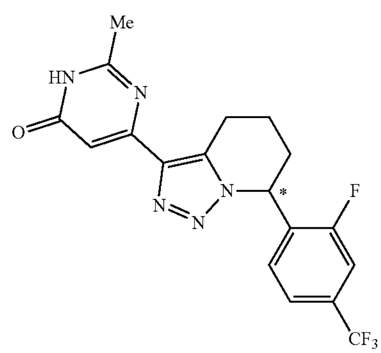 [SMILES: Cc1nc(-c2nnn3c2CCCC3c2ccc(C(F)(F)F)cc2F)cc(=O)[nH]1] | (R)- or (S)-6-(7-(2-fluoro-4-(trifluoromethyl)phenyl)-4,5,6,7-tetrahydro-[1,2,3]triazolo[1,5-a]pyridin-3-yl)-2-methylpyrimidin-4(3H)-one | Calc'd 394.1, found 393.9 | Chiralpak IC column |
| 50 | 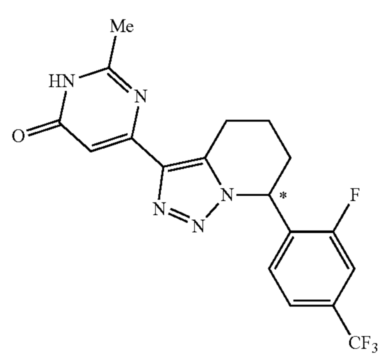 [SMILES: Cc1nc(-c2nnn3c2CCCC3c2ccc(C(F)(F)F)cc2F)cc(=O)[nH]1] | (S)- or (R)-6-(7-(2-fluoro-4-(trifluoromethyl)phenyl)-4,5,6,7-tetrahydro-[1,2,3]triazolo[1,5-a]pyridin-3-yl)-2-methylpyrimidin-4(3H)-one | Calc'd 394.1, found 393.9 | Chiralpak IC column |

TABLE 12-continued

The following compounds were prepared using procedures similar to those described for Examples 47 and 48 using the appropriate starting materials.

| Example No. | Structure | IUPAC name | Exact Mass [M + H]+ | Chiral Column |
|---|---|---|---|---|
| 51 | 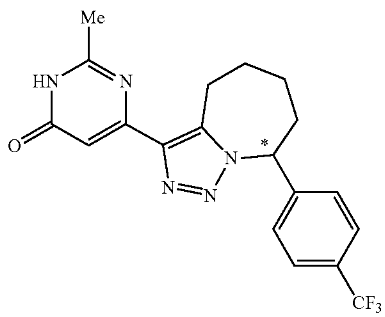 [SMILES: Cc1nc(-c2nnn3c2CCCCC3c2ccc(C(F)(F)F)cc2)cc(=O)[nH]1] | (R)- or (S)-2-methyl-6-(8-(4-(trifluoromethyl)phenyl)-5,6,7,8-tetrahydro-4H-[1,2,3]triazolo[1,5-a]azepin-3-yl)pyrimidin-4(3H)-one | Calc'd 390.2, found 390.2 | Chiralpak AS-H |
| 52 | 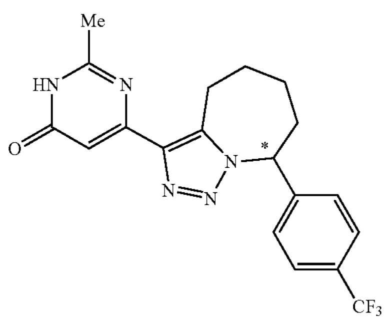 [SMILES: Cc1nc(-c2nnn3c2CCCCC3c2ccc(C(F)(F)F)cc2)cc(=O)[nH]1] | (S)- or (R)-2-methyl-6-(8-(4-(trifluoromethyl)phenyl)-5,6,7,8-tetrahydro-4H-[1,2,3]triazolo[1,5-a]azepin-3-yl)pyrimidin-4(3H)-one | Calc'd 390.2, found 390.2 | Chiralpak AS-H |
| 53 | 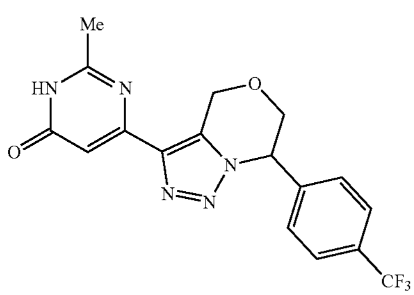 [SMILES: Cc1nc(-c2nnn3c2COCC3c2ccc(C(F)(F)F)cc2)cc(=O)[nH]1] | 2-methyl-6-(7-(4-(trifluoromethyl)phenyl)-6,7-dihydro-4H-[1,2,3]triazolo[5,1-c][1,4]oxazin-3-yl)pyrimidin-4(3H)-one | Calc'd 378.1, found 378.1 | None (not resolved) |

Examples 54 and 55

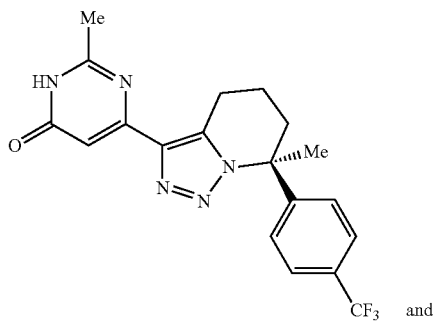

and

-continued

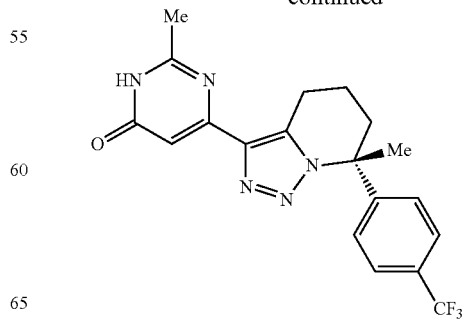

(R)- and (S)-2-Methyl-6-(7-methyl-7-(4-(trifluoromethyl)phenyl)-4,5,6,7-tetrahydro-[1,2,3]triazolo[1,5-a]pyridin-3-yl)pyrimidin-4(3H)-one, (Scheme 14)

Step 1. 6-(Trimethylsilyl)hex-5-yn-1-ol

A solution of hex-5-yn-1-ol (2.25 ml, 20.38 mmol) in THF (50 ml) cooled to −78° C. was treated with n-hexyllithium (19.49 ml, 44.8 mmol). The reaction was stirred for 1 h at −78° C. before the introduction of TMSCl (7.81 ml, 61.1 mmol). The reaction was stirred for 30 minutes at −78° C. and then warmed to RT and stirred for 1 h. The reaction was quenched with saturated $NH_4Cl$ solution. The mixture was diluted with ethyl ether and the layers were separated. The organic layer was then washed with 1N HCl (2×). The extract was washed with water and then dried over $Na_2SO_4$, filtered, and concentrated. The crude alcohol was used directly in the next step. The procedure was adapted from: Robles, O.; Serna-Saldivar, S. O.; Gutierrez-Uribe, J. A.; Romo, D. *Org. Lett.* 2012, 14, 1394-1397.

Step 2. 6-(Trimethylsilyl)hex-5-ynal

DMSO (4.34 ml, 61.1 mmol) was added to a −78° C. solution of oxalyl chloride (2.68 ml, 30.6 mmol) in DCM (80 ml). The mixture was stirred for 10 minutes before the addition of 6-(trimethylsilyl)hex-5-yn-1-ol (3.47 g, 20.37 mmol) as a solution in DCM (10 ml). This mixture was stirred for 30 minutes at −78° C. and then treated with triethylamine (14.20 ml, 102 mmol). The resulting mixture was stirred for 20 minutes at −78° C. and then warmed to RT and stirred for 1 h. The reaction was then quenched with saturated $NaHCO_3$ solution and the aqueous layer was extracted with DCM (2×). The organic extracts were combined and washed with 1N HCl (2×), water (1×), and then dried over $Na_2SO_4$. This mixture was filtered and concentrated. The crude aldehyde was then used in the next step without further purification. $^1$H NMR (500 MHz, $CDCl_3$) δ: 9.84 (t, J=1.5 Hz, 1H), 2.61 (td, J=7.5 Hz, J=1.5 Hz, 2H), 2.34 (t, J=7.0 Hz, 2H), 1.88 (m, 2H), 0.18 (s, 9H).

Step 3. 1-(4-(Trifluoromethyl)phenyl)-6-(trimethylsilyl)hex-5-yn-1-ol n-hexyllithium (9.38 ml, 21.57 mmol) was added to a −40° C. solution of 1-bromo-4-(trifluoromethyl)benzene (3.29 ml, 23.53 mmol) in THF (50 ml). The reaction was stirred at −40° C. for 45 minutes and then a solution of 6-(trimethylsilyl)hex-5-ynal (3.3 g, 19.61 mmol) in THF (20 mL) was added. The reaction was stirred for 15 min at −40° C. and then warmed to 0° C. and stirred for an additional 30 minutes. The reaction was then quenched with saturated $NH_4Cl$ solution. The product was extracted with ethyl acetate. The extracts were dried over $Na_2SO_4$, filtered, and concentrated. The residue was then purified by silica gel chromatography (0-25% ethyl acetate in hexanes). $^1$H NMR (500 MHz, $CDCl_3$) δ: 7.64 (d, J=8 Hz, 2H), 7.50 (d, J=8 Hz, 2H), 4.84 (t, J=6.5 Hz, 1H), 2.31 (dt, J=7 Hz, J=2.5 Hz, 2H), 1.95-1.84 (m, 2H), 1.76 (broad, 1H), 1.73-1.64 (m, 1H), 1.63-1.54 (m, 1H), 0.17 (s, 9H).

Step 4. 1-(4-(Trifluoromethyl)phenyl)-6-(trimethylsilyl)hex-5-yn-1-one

DMSO (2.167 ml, 30.5 mmol) was added to a −78° C. solution of oxalyl chloride (1.336 ml, 15.27 mmol) in DCM (40 ml). The mixture was stirred for 10 minutes before the addition of 1-(4-(trifluoromethyl)phenyl)-6-(trimethylsilyl)hex-5-yn-1-ol (3.2 g, 10.18 mmol) as a solution in DCM (10 ml). This mixture was stirred for 30 minutes at −78° C. and then treated with triethylamine (7.09 ml, 50.9 mmol). The resulting mixture was stirred for 20 minutes at −78° C. and then warmed to RT and stirred for 1 h. The reaction was then quenched with saturated $NaHCO_3$ solution and the aqueous layer was extracted with DCM (2×). The organic extracts were combined and washed with 1N HCl (2×), water (1×), and then dried over $Na_2SO_4$. This mixture was filtered and concentrated. The crude ketone was then used in the next step without further purification. $^1$H NMR (500 MHz, $CDCl_3$) δ: 8.11 (d, J=8.5 Hz, 2H), 7.77 (d, J=8.5 Hz, 2H), 3.17 (t, J=7 Hz, 2H), 2.41 (t, J=7 Hz, 2H), 2.00 (app q, J=7 Hz, 2H), 0.17 (s, 9H).

Step 5. 2-(4-(Trifluoromethyl)phenyl)hept-6-yn-2-ol

Methylmagnesium bromide (3.83 ml, 11.49 mmol) was added to a 0° C. solution of 1-(4-(trifluoromethyl)phenyl)-6-(trimethylsilyl)hex-5-yn-1-one (2.76 g, 8.83 mmol) in THF (25 ml). The reaction was stirred for 10 minutes at 0° C. The reaction was quenched with saturated $NH_4Cl$ solution. The quenched solution was diluted with ethyl acetate and the layers were separated. The organic extract was dried over $Na_2SO_4$, filtered, and concentrated. The crude material was used in the next step without further purification.

TBAF (10.41 ml, 10.41 mmol) was added to a solution of 2-(4-(trifluoromethyl)phenyl)-7-(trimethylsilyl)hept-6-yn-2-ol (2.85 g, 8.68 mmol) in THF (20 ml). The reaction was stirred for 20 minutes at RT. The reaction was quenched with saturated $NaHCO_3$ solution. The mixture was diluted with ethyl acetate and the layers were separated. The organic extract was washed with water, dried over $Na_2SO_4$, filtered, and concentrated. The residue was then purified by silica gel chromatography (0-20% ethyl acetate in hexanes). $^1$H NMR (500 MHz, $CDCl_3$) δ: 7.63 (d, J=8.5 Hz, 2H), 7.58 (d, J=8.5 Hz, 2H), 2.20-2.17 (m, 2H), 2.02-1.91 (m, 3H), 1.71 (s, 1H), 1.62 (s, 3H), 1.61-1.53 (m, 1H), 1.41-1.32 (m, 1H).

Step 6. 7-(6-((4-Methoxybenzyl)oxy)-2-methylpyrimidin-4-yl)-2-(4-(trifluoromethyl)-phenyl)hept-6-yn-2-ol A solution of 4-chloro-6-((4-methoxybenzyl)oxy)-2-methylpyrimidine (940 mg, 3.55 mmol), 2-(4-(trifluoromethyl)phenyl)hept-6-yn-2-ol (1001 mg, 3.91 mmol), and triethylamine (1.485 ml, 10.65 mmol) in THF (12 ml) was degassed with nitrogen for 5 minutes. Then bis(triphenylphosphine)palladium(II) chloride (199 mg, 0.284 mmol) and copper(I) iodide (81 mg, 0.426 mmol) were added and the reaction was heated to 65° C. overnight. The reaction was cooled to RT and concentrated. The residue was then purified by silica gel chromatography (0-80% ethyl acetate in hexanes) to furnish the title compound. MS=484.9 (M+1).

Step 7. 5-(4-(6-((4-Methoxybenzyl)oxy)-2-methylpyrimidin-4-yl)-1H-1,2,3-triazol-5-yl)-2-(4-(trifluoromethyl)phenyl)pentan-2-ol 7-(6-((4-methoxybenzyl)oxy)-2-methylpyrimidin-4-yl)-2-(4-(trifluoromethyl)phenyl)hept-6-yn-2-ol (900 mg, 1.858 mmol) and sodium azide (242 mg, 3.72 mmol) were combined in DMA (6.8 ml) and heated to 80° C. overnight. The reaction was cooled to RT and quenched with saturated $NaHCO_3$ solution. The product was extracted with ethyl acetate and the extract was washed with brine (3×). The extract was dried over Na₂SO₄, filtered, and concentrated. The residue was then purified by silica gel chromatography (10-70% (3:1 EtOAc:EtOH) in hexanes).

MS=528.0 (M+1).

Step 8. (R)- and (S)-2-Methyl-6-(7-methyl-7-(4-(trifluoromethyl)phenyl)-4,5,6,7-tetrahydro-[1,2,3]triazolo[1,5-a]pyridin-3-yl)pyrimidin-4(3H)-one A solution of 5-(4-(6-((4-methoxy-benzyl)oxy)-2-methyl-pyrimidin-4-yl)-1H-1,2,3-triazol-5-yl)-2-(4-(trifluoromethyl)phenyl)-pentan-2-ol (590 mg, 0.559 mmol) in DCE (9 ml) was treated with TFA (6 ml, 78 mmol) and stirred until the reaction was judged to be complete by LCMS. The reaction was concentrated, taken up in DCM, and washed with saturated NaHCO₃ solution. The organic layer was dried over Na₂SO₄, filtered, and concentrated. The residue was then purified by silica gel chromatography (ISCO 24 g silica cartridge; 5-40% (3:1 EtOAc:EtOH) in hexanes). The product containing fractions were concentrated and the racemic title compound was separated by chiral chromatography (Chiralpak AS-H column; 14% MeOH+0.1% NH₄OH in CO₂) into the enantiomers of the title compound. The faster-eluting enantiomer of the title compound (Example 54): ¹H NMR (500 MHz, DMSO-d6) δ: 12.9-12.0 (broad, 1H), 7.70 (d, J=8.5 Hz, 2H), 7.03 (d, J=8.5 Hz, 2H), 6.73 (s, 1H), 3.39 (obscured by DMSO) (m, 1H), 3.08-3.01 (m, 1H), 2.43-2.38 (m, 1H), 2.33 (s, 3H), 2.25-2.19 (m, 1H), 2.09 (s, 3H), 1.83-1.77 (m, 1H), 1.34-1.24 (m, 1H). MS=390.0 (M+1). The slower-eluting enantiomer of the title compound (Example 55): ¹H NMR (500 MHz, DMSO-d6) δ: 12.9-12.0 (broad, 1H), 7.70 (d, J=8.5 Hz, 2H), 7.03 (d, J=8.5 Hz, 2H), 6.73 (s, 1H), 3.39 (obscured by DMSO) (m, 1H), 3.08-3.01 (m, 1H), 2.43-2.38 (m, 1H), 2.33 (s, 3H), 2.25-2.19 (m, 1H), 2.09 (s, 3H), 1.83-1.77 (m, 1H), 1.34-1.24 (m, 1H). MS=390.0 (M+1).

TABLE 13

The following compounds were prepared using procedures similar to those described for Examples 54 and 55 using the appropriate starting materials.

| Example No. | Structure | IUPAC name | Exact Mass [M + H]+ | Chiral Column |
|---|---|---|---|---|
| 56 | 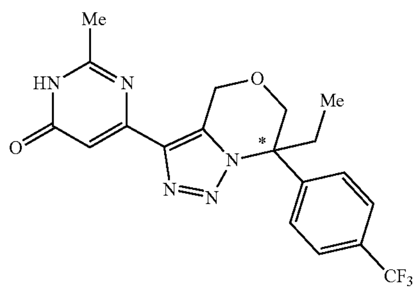 [SMILES: CCC1(c2ccc(C(F)(F)F)cc2)COCc2c(-c3cc(=O)[nH]c(C)n3)nnn21] | (R)- or (S)-6-(7-ethyl-7-(4-(trifluoromethyl)phenyl)-4,5,6,7-tetrahydro-[1,2,3]triazolo[1,5-a]pyridin-3-yl)-2-methylpyrimidin-4(3H)-one | Calc'd 404.2, found 404.1 | Chiralpak AD-H |
| 57 | 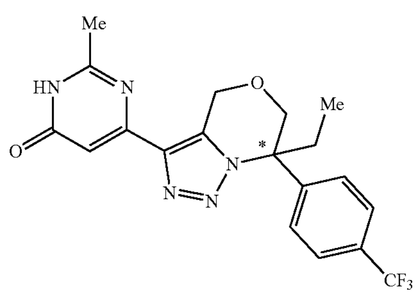 [SMILES: CCC1(c2ccc(C(F)(F)F)cc2)COCc2c(-c3cc(=O)[nH]c(C)n3)nnn21] | (S)- or (R)-6-(7-ethyl-7-(4-(trifluoromethyl)phenyl)-4,5,6,7-tetrahydro-[1,2,3]triazolo[1,5-a]pyridin-3-yl)-2-methylpyrimidin-4(3H)-one | Calc'd 404.2, found 404.1 | Chiralpak AD-H |
| 58 | 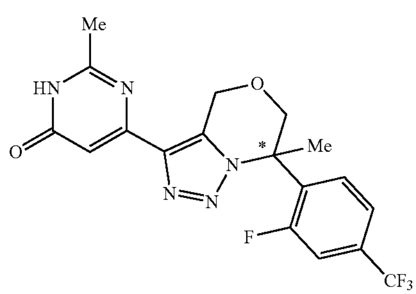 [SMILES: Cc1nc(-c2nnn3c2COCC3(C)c2ccc(C(F)(F)F)cc2F)cc(=O)[nH]1] | (R)- or (S)-6-(7-(2-fluoro-4-(trifluoromethyl)phenyl)-7-methyl-4,5,6,7-tetrahydro-[1,2,3]triazolo[1,5-a]pyridin-3-yl)-2-methylpyrimidin-4(3H)-one | Calc'd 408.1, found 408.2 | Lux Cellulose-4 |

TABLE 13-continued

The following compounds were prepared using procedures similar to those described for Examples 54 and 55 using the appropriate starting materials.

| Example No. | Structure | IUPAC name | Exact Mass [M + H]+ | Chiral Column |
|---|---|---|---|---|
| 59 | 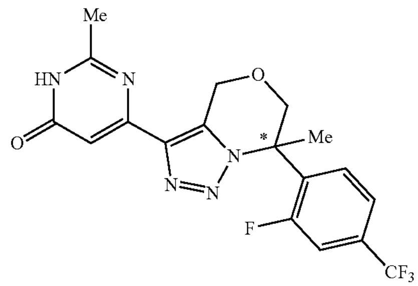 [SMILES: Cc1nc(-c2nnn3c2COCC3(C)c2ccc(C(F)(F)F)cc2F)cc(=O)[nH]1] | (S)- or (R)-6-(7-(2-fluoro-4-(trifluoromethyl)phenyl)-7-methyl-4,5,6,7-tetrahydro-[1,2,3]triazolo[1,5-a]pyridin-3-yl)-2-methylpyrimidin-4(3H)-one | Calc'd 408.1, found 408.2 | Lux Cellulose-4 |

Example 60

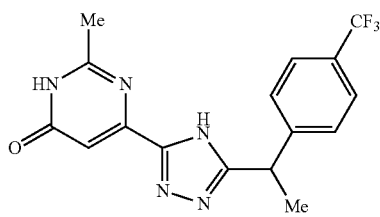 [SMILES: Cc1nc(-c2nnc(C(C)c3ccc(C(F)(F)F)cc3)[nH]2)cc(=O)[nH]1]

2-Methyl-6-(5-(1-(4-(trifluoromethyl)phenyl)ethyl)-4H-1,2,4-triazol-3-yl)pyrimidin-4(3H)-one, (Scheme 15)

Step 1. 2-(4-(Trifluoromethyl)phenyl)propanoic Acid n-Butyllithium (2.5 M in hexane, 4.3 mL, 10.8 mmol) was added dropwise to a solution of diisopropylamine (1.09 g, 10.8 mmol) in THF (15 mL) cooled to 0° C. The resulting solution was stirred for 20 minutes at that temperature. Then a solution of 2-(4-(trifluoromethyl)phenyl)acetic acid (1.00 g, 4.9 mmol) in THF (30 mL) was added dropwise at −70° C. over 10 min. The resulting mixture was stirred for 1 h at −70° C. To the mixture was added dropwise a solution of CH₃I (0.3 mL, 5.4 mmol) in THF (15 mL) at −70° C. over 10 minutes. The reaction solution was stirred for 2 h at −70° C. The resulting solution was quenched with saturated NH₄Cl solution (60 mL). The pH of the resulting mixture was adjusted to 2 with HCl (1M in water) and extracted with EtOAc (3×100 mL). The combined organic extracts were washed with brine (100 mL), dried over anhydrous Na₂SO₄ and filtered. The filtrate was concentrated under reduced pressure. The residue was purified by column chromatography over silica gel (1:1:6 EtOAc:MeOH:petroleum ether) to provide the title compound. ¹H NMR (300 MHz, CDCl₃) δ: 10.11 (br, 1H), 7.61 (d, J=8.4 Hz, 2H), 7.45 (d, J=8.4 Hz, 2H), 3.82 (q, J=7.2 Hz, 1H), 1.56 (d, J=7.2 Hz, 3H).

Step 2. 2-(4-(Trifluoromethyl)phenyl)propanehydrazide

A solution of 2-(4-(trifluoromethyl)phenyl)propanoic acid (0.300 g, 1.4 mmol) in SOCl₂ (2 mL) was stirred at 80° C. for 1 h. The resulting mixture was cooled to RT and concentrated under reduced pressure. The residue was dissolved in THF (3 mL). To the solution was added dropwise a solution of hydrazine hydrate (0.635 g, 12.7 mmol) in THF (3 mL) at 0° C. The reaction mixture was stirred at 0° C. for 15 minutes. The resulting mixture was quenched with water (20 mL) and the product was extracted with EtOAc (3×20 mL). The combined organic extracts were washed with brine (30 mL), dried over anhydrous Na₂SO₄ and filtered. The filtrate was concentrated under reduced pressure to afford the title compound as a liquid, which was used in next step without further purification. MS=233.4 (M+1).

Step 3. 2-Methyl-6-oxo-N-(2-(4-(trifluoromethyl)phenyl)propanoyl)-1,6-dihydropyrimidine-4-carbo-hydrazide To a mixture of 2-(4-(trifluoromethyl)phenyl)propanehydrazide (300 mg, 0.9 mmol) in NMP (3 mL) were added 2-methyl-6-oxo-1,6-dihydropyrimidine-4-carboxylic acid (139 mg, 0.9 mmol), HATU (344 mg, 0.9 mmol) and Hunig's base (584 mg, 4.5 mmol). The reaction mixture was stirred at RT for 2 h. The resulting mixture was quenched with water (30 mL) and extracted with EtOAc (3×20 mL). The combined organic extracts were washed with brine (30 mL), dried over anhydrous Na₂SO₄ and filtered. The filtrate was concentrated under reduced pressure. The residue was purified by column chromatography over silica gel (20% methanol in dichloromethane) to provide the title compound after concentration. MS=369.3 (M+1).

Step 4. 2-Methyl-6-(5-(1-(4-(trifluoromethyl)phenyl)ethyl)-1,3,4-oxadiazol-2-yl)-pyrimidin-4-ol To a mixture of Burgess reagent (129 mg, 0.5 mmol) in dioxane (5 mL) was added 2-methyl-6-oxo-N-(2-(4-(trifluoromethyl)phenyl)propanoyl)-1,6-dihydropyrimidine-4-carbo-hydrazide (80 mg, 0.2 mmol). The reaction mixture was purged with nitrogen 3 times. The final reaction mixture subjected to microwave irradiation for 50 minutes at 120° C. The resulting mixture was cooled to RT, diluted with brine (10 mL) and the mixture was extracted with EtOAc (3×10 mL). The combined organic extracts were dried over anhydrous Na₂SO₄ and filtered. The filtrate was concentrated under reduced pressure. The residue was purified by preparative HPLC (X-bridge shield C18 column; 5-38% acetonitrile in water+0.05% NH₄HCO₃) to provide the title compound after concentration.

MS=351.1 (M+1).

Step 5. 2-Methyl-6-(5-(1-(4-(trifluoromethyl)phenyl)ethyl)-4H-1,2,4-triazol-3-yl)pyrimidin-4(3H)-one NH₄OAc (220 mg, 2.9 mmol) was added to a solution of 2-methyl-6-(5-(1-(4-(trifluoromethyl)phenyl)ethyl)-1,3,4-oxadiazol-2-yl)pyrimidin-4(3H)-one (100 mg, 0.3 mmol) in acetic acid (5 mL). The reaction mixture was purged with nitrogen 3 times and stirred for 24 h at 140° C. The resulting mixture was cooled to RT and concentrated under reduced pressure. The residue was diluted with brine (10 mL) and extracted with EtOAc (3×10 mL). The combined organic extracts were dried over anhydrous Na₂SO₄ and filtered. The filtrate was concentrated under reduced pressure. The residue was then purified by column chromatography over silica gel (20% ethyl acetate in petroleum ether). The product-containing fractions were combined and concentrated. The crude product was purified by preparative HPLC (GILSON (GX-281); Gemini column; mobile phase: 25-45% acetonitrile in water+0.05% NH₄HCO₃) to provide the title compound as a solid after concentration. ¹H NMR (400 MHz, DMSO-d₆) δ: 7.71 (d, J=8.4 Hz, 2H), 7.56 (d, J=8.4 Hz, 2H), 6.72 (s, 1H), 4.47 (q, J=7.6 Hz, 1H), 2.39 (s, 3H), 1.67 (d, J=7.6 Hz, 3H). MS=350.1 (M+1).

TABLE 14

The following compounds were prepared using procedures similar to those described for Examples 60 using the appropriate starting materials.

| Example No. | Structure | IUPAC name | Exact Mass [M + H]+ | Chiral Column |
|---|---|---|---|---|
| 61 | 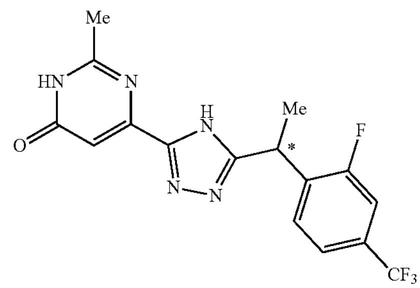 [SMILES: Cc1nc(-c2nnc(C(C)c3ccc(C(F)(F)F)cc3F)[nH]2)cc(=O)[nH]1] | (R)- or (S)-6-(5-(1-(2-fluoro-4-(trifluoromethyl)phenyl)ethyl)-4H-1,2,4-triazol-3-yl)-2-methylpyrimidin-4(3H)-one | Calc'd 368.1, found 368.0 | (R,R)-WHELK-01 |
| 62 | 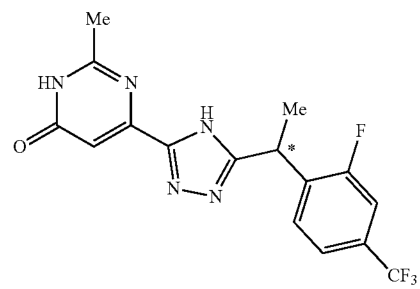 [SMILES: Cc1nc(-c2nnc(C(C)c3ccc(C(F)(F)F)cc3F)[nH]2)cc(=O)[nH]1] | (S)- or (R)-6-(5-(1-(2-fluoro-4-(trifluoromethyl)phenyl)ethyl)-4H-1,2,4-triazol-3-yl)-2-methylpyrimidin-4(3H)-one | Calc'd 368.1, found 368.0 | (R,R)-WHELK-01 |
| 63 | 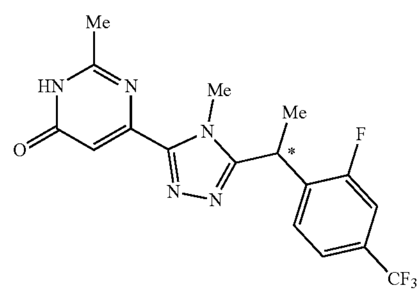 [SMILES: Cc1nc(-c2nnc(C(C)c3ccc(C(F)(F)F)cc3F)n2C)cc(=O)[nH]1] | (R)- or (S)-6-(5-(1-(2-fluoro-4-(trifluoromethyl)phenyl)ethyl)-4-methyl-4H-1,2,4-triazol-3-yl)-2-methylpyrimidin-4(3H)-one | Calc'd 382.1, found 382.0 | (R,R)-WHELK-01 |
| 64 | 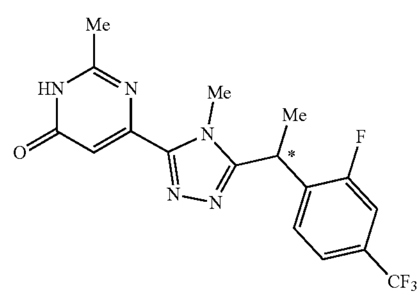 [SMILES: Cc1nc(-c2nnc(C(C)c3ccc(C(F)(F)F)cc3F)n2C)cc(=O)[nH]1] | (S)- or (R)-6-(5-(1-(2-fluoro-4-(trifluoromethyl)phenyl)ethyl)-4-methyl-4H-1,2,4-triazol-3-yl)-2-methylpyrimidin-4(3H)-one | Calc'd 382.1, found 382.0 | (R,R)-WHELK-01 |

TABLE 14-continued

The following compounds were prepared using procedures similar to those described for Examples 60 using the appropriate starting materials.

| Example No. | Structure | IUPAC name | Exact Mass [M + H]+ | Chiral Column |
|---|---|---|---|---|
| 65 | 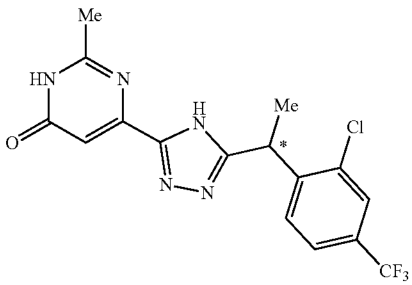 [SMILES: Cc1nc(-c2nnc(C(C)c3ccc(C(F)(F)F)cc3Cl)[nH]2)cc(=O)[nH]1] | (R)- or (S)-6-(5-(1-(2-chloro-4-(trifluoromethyl)-phenyl)ethyl)-4H-1,2,4-triazol-3-yl)-2-methylpyrimidin-4(3H)-one | Calc'd 384.1, found 384.1 | (R,R)-WHELK-01 |
| 66 | 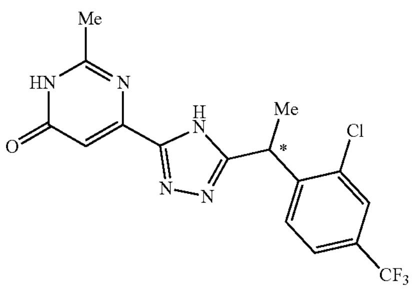 [SMILES: Cc1nc(-c2nnc(C(C)c3ccc(C(F)(F)F)cc3Cl)[nH]2)cc(=O)[nH]1] | (S)- or (R)-6-(5-(1-(2-chloro-4-(trifluoromethyl)-phenyl)ethyl)-4H-1,2,4-triazol-3-yl)-2-methylpyrimidin-4(3H)-one | Calc'd 384.1, found 384.1 | (R,R)-WHELK-01 |
| 67 | 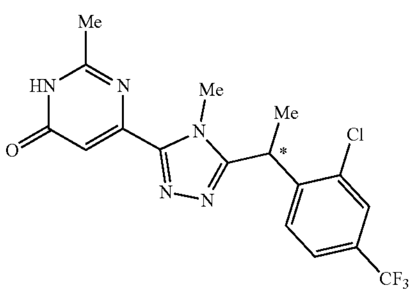 [SMILES: Cc1nc(-c2nnc(C(C)c3ccc(C(F)(F)F)cc3Cl)n2C)cc(=O)[nH]1] | (R)- or (S)-6-(5-(1-(2-chloro-4-(trifluoromethyl)-phenyl)ethyl)-4-methyl-4H-1,2,4-triazol-3-yl)-2-methylpyrimidin-4(3H)-one | Calc'd 398.1, found 398.0 | (R,R)-WHELK-01 |
| 68 | 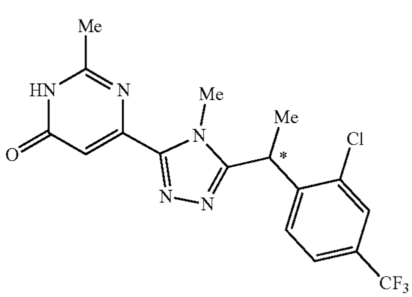 [SMILES: Cc1nc(-c2nnc(C(C)c3ccc(C(F)(F)F)cc3Cl)n2C)cc(=O)[nH]1] | (S)- or (R)-6-(5-(1-(2-chloro-4-(trifluoromethyl)-phenyl)ethyl)-4-methyl-4H-1,2,4-triazol-3-yl)-2-methylpyrimidin-4(3H)-one | Calc'd 398.1, found 398.0 | (R,R)-WHELK-01 |

Example 69

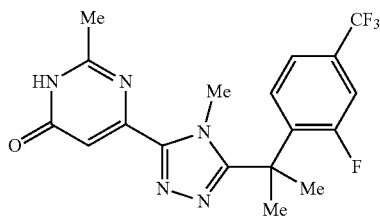 [SMILES: Cc1nc(-c2nnc(C(C)(C)c3ccc(C(F)(F)F)cc3F)n2C)cc(=O)[nH]1]

6-(5-(2-(2-Fluoro-4-(trifluoromethyl)phenyl)propan-2-yl)-4-methyl-4H-1,2,4-triazol-3-yl)-2-methylpyrimidin-4(3H)-one (Scheme 15)

Step 1. tert-Butyl 2-(2-methyl-6-oxo-1,6-dihydropyrimidine-4-carbonyl)hydrazinecarboxylate To a solution of 2-methyl-6-oxo-1,6-dihydropyrimidine-4-carboxylic acid (1.5 g, 9.73 mmol) in NMP (16 ml) was added HATU (3.70 g, 9.73 mmol), tert-butyl hydrazinecarboxylate (1.929 g, 14.60 mmol) and triethylamine (2.95 g, 29.2 mmol). The resulting solution was stirred for 2 h at RT. Then the reaction mixture was purified by preparative HPLC (MeOH:H$_2$O (20:1 to 10:1)) to furnish the title compound as a solid after concentration. MS=269.1 (M+1).

Step 2. 2-Methyl-6-oxo-1,6-dihydropyrimidine-4-carbohydrazide Hydrochloride

A mixture of tert-butyl 2-(2-methyl-6-oxo-1,6-dihydropyrimidine-4-carbonyl)hydrazinecarboxylate (1.5 g, 5.59 mmol) in HCl in dioxane (50 ml) was stirred for 3 h at RT. Then the mixture was filtered. The filter cake was washed with hexane (100 mL) to provide the title compound as a solid. MS=169.1 (M+1).

Step 3. N'-(2-(2-Fluoro-4-(trifluoromethyl)phenyl)-2-methylpropanoyl)-2-methyl-6-oxo-1,6-dihydropyrimidine-4-carbohydrazide A solution of 2-(2-fluoro-4-(trifluoromethyl)phenyl)-2-methylpropanoic acid (300 mg, 1.199 mmol), HATU (456 mg, 1.199 mmol), 2-methyl-6-oxo-1,6-dihydropyrimidine-4-carbohydrazide (302 mg, 1.799 mmol) and TEA (0.836 ml, 6.00 mmol) in NMP (10 ml) were stirred at 25° C. for 16 h. The reaction was quenched with water (30 mL) and extracted with ethyl acetate (3×100 mL). The combined organic extracts were washed with brine (1×100 mL), dried over anhydrous sodium sulfate, and filtered. The filtrate was concentrated under reduced pressure and the residue was purified by silica gel chromatography (1-5% MeOH in DCM) to afford the title compound as a solid. MS=401.0 (M+1).

Step 4. 6-(5-(4-azido-1-(4-(trifluoromethyl)phenyl)butyl)-1,3,4-oxadiazol-2-yl)-2-methylpyrimidin-4(3H)-one To a solution of N'-(2-(2-fluoro-4-(trifluoromethyl)phenyl)-2-methylpropanoyl)-2-methyl-6-oxo-1,6-dihydropyrimidine-4-carbohydrazide (300 mg, 0.749 mmol) in dioxane (5 ml) was added Burgess reagent (893 mg, 3.75 mmol) at 25° C. The reaction was irradiated with microwave radiation at 120° C. for 1 h. The solvent was evaporated under reduced pressure and the residue was purified by silica gel chromatography (1-5% MeOH in DCM) to afford the title compound as a solid. MS=383.0 (M+1).

Step 5. 6-(5-(2-(2-Fluoro-4-(trifluoromethyl)phenyl)propan-2-yl)-4-methyl-4H-1,2,4-triazol-3-yl)-2-methylpyrimidin-4(3H)-one To a solution of 6-(5-(2-(2-fluoro-4-(trifluoromethyl)phenyl)-propan-2-yl)-1,3,4-oxadiazol-2-yl)-2-methylpyrimidin-4(3H)-one (150 mg, 0.392 mmol) in methylamine solution (30% in ethanol; 10 ml) was added methanamine 2,2,2-trifluoroacetate (1.14 g, 7.85 mmol) at 25° C. in a sealed tube. After stirring at 150° C. for 16 h, the solvent was evaporated under reduced pressure and the residue was purified by silica gel chromatography (1-5% MeOH in DCM) to afford the title compound as a solid. $^1$H NMR (300 MHz, DMSO-d$_6$) δ: 12.66 (br, 1H), 7.79-7.74 (m, 1H), 7.68-7.64 (m, 2H), 6.70 (s, 1H), 3.34 (s, 3H), 2.30 (s, 3H), 1.81 (s, 6H). MS=396.2 (M+1).

Examples 70 and 71

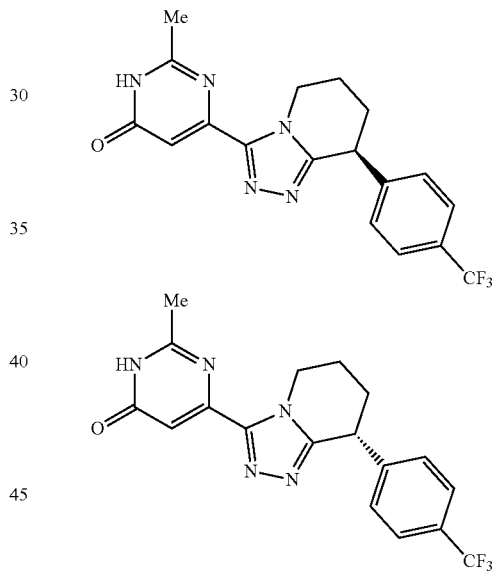

(R)- and (S)-2-Methyl-6-(8-(4-(trifluoromethyl)phenyl)-5,6,7,8-tetrahydro-[1,2,4]triazolo[4,3-a]pyridin-3-yl)pyrimidin-4(3H)-one (Scheme 16)

Step 1. Methyl 5-chloro-2-(4-(trifluoromethyl)phenyl)pentanoate

To a solution of methyl 2-(4-(trifluoromethyl)phenyl)acetate (2.0 g, 9.17 mmol) in DMF (20 ml) was added sodium hydride (0.403 g, 10.08 mmol) at 0° C. After stirring at 25° C. for 1 h, 1-chloro-3-iodopropane (1.968 g, 9.63 mmol) was added dropwise at 0° C. to the mixture. After stirring at 25° C. for 16 h, the reaction was quenched with saturated NH$_4$Cl solution (100 mL) and extracted with ethyl acetate (3×200 mL). The combined organic extracts were washed with brine (3×200 mL), dried over anhydrous Na$_2$SO$_4$, filtered, and concentrated. The residue was purified by silica gel chromatography (1-15% ethyl acetate in petroleum ether) to furnish the title compound as an oil. $^1$H NMR (300 MHz, CDCl$_3$) δ: 7.61 (d, J=8.1 Hz, 2H), 7.44 (d, J=8.1 Hz, 2H), 3.69 (s, 3H), 3.65 (t, J=7.8 Hz, 1H), 3.54 (t, J=6.5 Hz, 2H), 2.28-2.19 (m, 1H), 2.04-1.90 (m, 1H), 1.84-1.55 (m, 2H).

Step 2.
5-Chloro-2-(4-(trifluoromethyl)phenyl)pentanoic Acid

To a solution of methyl 5-chloro-2-(4-(trifluoromethyl)phenyl)pentanoate (2.0 g, 6.79 mmol) in THF (12 ml) and water (8 ml) was added sodium hydroxide (0.814 g, 20.36 mmol) at 25° C. After stirring at 25° C. for 16 h the THF was removed under by evaporation under reduced pressure. The residue was diluted with water (80 mL) and extracted with diethyl ether (1×100 mL). The pH of the aqueous layer was adjusted to 3 with 1 N HCl. The product was extracted with ethyl acetate (3×200 mL). The combined organic extracts were washed with brine (1×200 mL), dried over anhydrous Na$_2$SO$_4$, filtered, and concentrated to furnish the title compound as an oil. $^1$H NMR (400 MHz, CDCl$_3$) δ: 7.61 (d, J=8.0 Hz, 2H), 7.45 (d, J=8.0 Hz, 2H), 3.66 (t, J=7.6 Hz, 1H), 3.53 (t, J=7.6 Hz, 2H), 2.30-2.21 (m, 1H), 2.02-1.94 (m, 1H), 1.86-1.66 (m, 2H).

Step 3. N'-(5-Chloro-2-(4-(trifluoromethyl)phenyl)pentanoyl)-2-methyl-6-oxo-1,6-dihydropyrimidine-4-carbohydrazide A solution of 5-chloro-2-(4-(trifluoromethyl)phenyl)-pentanoic acid (500 mg, 1.781 mmol), HATU (677 mg, 1.781 mmol), 2-methyl-6-oxo-1,6-dihydropyrimidine-4-carbohydrazide (449 mg, 2.67 mmol) and triethylamine (1.241 ml, 8.91 mmol) in NMP (10 ml) were stirred at 25° C. for 16 h. The reaction was quenched with water (30 mL) and extracted with ethyl acetate (3×100 mL). The combined organic extracts were washed with brine (1×100 mL), dried over anhydrous Na$_2$SO$_4$, and filtered. The filtrate was concentrated under reduced pressure and the residue was purified by silica gel chromatography (1-5% MeOH in CH$_2$Cl$_2$) to furnish the title compound as a solid. MS=431.1 (M+1).

Step 4. 6-(5-(4-Chloro-1-(4-(trifluoromethyl)phenyl)butyl)-1,3,4-oxadiazol-2-yl)-2-methylpyrimidin-4(3H)-one To a solution of N'-(5-chloro-2-(4-(trifluoromethyl)phenyl)pentanoyl)-2-methyl-6-oxo-1,6-dihydropyrimidine-4-carbohydrazide (350 mg, 0.812 mmol) in dioxane (5 ml) was added Burgess reagent (968 mg, 4.06 mmol) at 25° C. The reaction was irradiated with microwave radiation at 120° C. for 1 h. The solvent was evaporated under reduced pressure and the residue was purified by a silica gel chromatography (1-5% MeOH in CH$_2$Cl$_2$) to furnish the title compound as a solid. MS=413.1 (M+1).

Step 5. 6-(5-(4-Azido-1-(4-(trifluoromethyl)phenyl)butyl)-1,3,4-oxadiazol-2-yl)-2-methylpyrimidin-4(3H)-one To a solution of 6-(5-(4-chloro-1-(4-(trifluoromethyl)phenyl)butyl)-1,3,4-oxadiazol-2-yl)-2-methylpyrimidin-4(3H)-one (200 mg, 0.485 mmol) in DMSO (5 ml) was added sodium azide (63.0 mg, 0.969 mmol) at 25° C. After stirring at 80° C. for 2 h, the reaction was quenched with water (30 mL) and extracted with ethyl acetate (3×100 mL). The combined organic extracts were washed with brine (1×100 mL), dried over anhydrous Na$_2$SO$_4$, and filtered. After filtration, the filtrate was concentrated under reduced pressure and the residue was purified by silica gel chromatography (1-5% MeOH in CH$_2$Cl$_2$) to furnish the title compound as a solid. MS=420.2 (M+1).

Step 6. (R)- and (S)-2-Methyl-6-(8-(4-(trifluoromethyl)phenyl)-5,6,7,8-tetrahydro-[1,2,4]triazolo[4,3-a]pyridin-3-yl)pyrimidin-4(3H)-one To a solution of 6-(5-(4-azido-1-(4-(trifluoromethyl)-phenyl)butyl)-1,3,4-oxadiazol-2-yl)-2-methylpyrimidin-4(3H)-one (140 mg, 0.334 mmol) in MeOH (4 ml) was added Pd/C (11.84 mg, 0.100 mmol) at 25° C. under an atmosphere of hydrogen. After stirring at 25° C. for 16 h, the mixture was filtered, washing with methanol (20 mL). The solvent was evaporated under reduced pressure and the residue was purified by silica gel chromatography (1-10% MeOH in DCM) to furnish the title compound. The racemic title compound was separated by chiral chromatography (Chiralpak IA column; 85:15 hexane:EtOH) into its enantiomeric title compounds. The faster-eluting enantiomer of the title compound (Example 70): $^1$H NMR (400 MHz, DMSO-d$_6$): δ 12.74 (br, 1H), 7.70 (d, J=8.0 Hz, 2H), 7.48 (d, J=8.0 Hz, 2H), 6.77 (s, 1H), 4.62-4.50 (m, 2H), 4.38-4.32 (m, 1H), 2.39 (s, 3H), 2.25-2.20 (m, 1H), 2.06-1.92 (m, 3H). MS=376.1 (M+1). The slower-eluting enantiomer of the title compound (Example 71): $^1$H NMR (400 MHz, DMSO-d$_6$): δ 12.66 (br, 1H), 7.70 (d, J=8.1 Hz, 2H), 7.47 (d, J=8.1 Hz, 2H), 6.76 (s, 1H), 4.65-4.57 (m, 1H), 4.52-4.50 (m, 1H), 4.37-4.31 (m, 1H), 2.38 (s, 3H), 2.26-2.14 (m, 1H), 2.06-1.88 (m, 3H). MS=376.2 (M+1).

TABLE 15

The following compounds were prepared using procedures similar to those described for examples 70 and 71 using the approrpriate materials.

| Example No. | Structure | IUPAC | Exact Mass [M + H]+ | Chiral Column |
|---|---|---|---|---|
| 72 | Me (structure shown) | (S)- or (R)-2-methyl-6-(8-methyl-8-(4-(trifluoromethyl)phenyl)-5,6,7,8-tetrahydro-[1,2,4]triazolo[4,3-a]pyridin-3-yl)pyrimidin-4(3H)-one | Calc'd 390.2, found 390.2 | Chiralpak IC |

TABLE 15-continued

The following compounds were prepared using procedures similar to those described for examples 70 and 71 using the approrpriate materials.

| Example No. | Structure | IUPAC | Exact Mass [M + H]+ | Chiral Column |
|---|---|---|---|---|
| 73 | 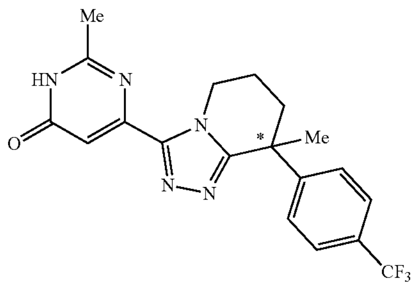 [SMILES: Cc1nc(-c2nnc3n2CCCC3(C)c2ccc(C(F)(F)F)cc2)cc(=O)[nH]1] | (S)- or (R)-2-methyl-6-(8-methyl-8-(4-(trifluoromethyl)phenyl)-5,6,7,8-tetrahydro-[1,2,4]triazolo[4,3-a]pyridin-3-yl)pyrimidin-4(3H)-one | Calc'd 390.2, found 390.2 | Chiralpak IC |

Examples 74 and 75

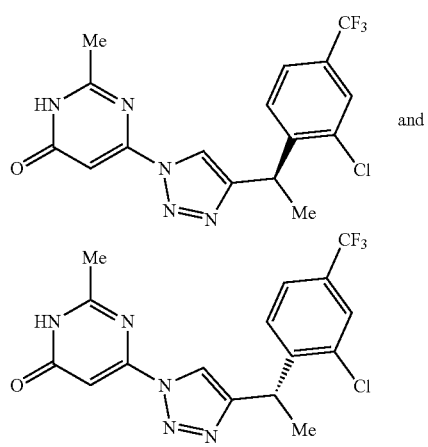

(R)- and (S)-6-(4-(1-(2-Chloro-4-(trifluoromethyl)phenyl)ethyl)-1H-1,2,3-triazol-1-yl)-2-methylpyrimidin-4(3H)-one (Scheme 17)

Step 1: Methyl 2-(2-chloro-4-(trifluoromethyl)phenyl)acetate

To a solution of 2-(2-chloro-4-(trifluoromethyl)phenyl) acetic acid (1.05 g, 4.40 mmol) in methanol (15 ml, 4.40 mmol) was added sulfuric acid (2.158 mg, 0.022 mmol) dropwise with stirring at 65° C. After 2 h, the reaction mixture was concentrated under reduced pressure. The residue was diluted with water (15 mL) and extracted with ethyl acetate (3×10 mL). The combined organic extracts were washed with brine (10 mL), dried over anhydrous sodium sulfate and filtered. The filtrate was concentrated under reduced pressure. The residue was purified by silica gel chromatography (1-15% ethyl acetate in petroleum ether) to furnish the title compound. MS=251.9/253.9 (M).

Step 2: Methyl 2-(2-chloro-4-(trifluoromethyl)phenyl)propanoate

Into a solution of methyl 2-(2-chloro-4-(trifluoromethyl) phenyl)acetate (952 mg, 3.77 mmol) in DMF (5.5 ml) was added sodium hydride (109 mg, 4.52 mmol) with stirring at 0° C. Then the reaction mixture was warmed to 25° C. and stirred for 0.5 h. Iodomethane (615 mg, 4.33 mmol) was then added at 0° C. Then the reaction mixture was warmed to 25° C. and stirred for 16 h. The reaction mixture was diluted with water (10 mL) and extracted with ethyl acetate (3×10 mL). The combined organic extracts were washed with brine (1×10 mL) and dried over anhydrous sodium sulfate and filtered. The filtrate was concentrated under reduced pressure. The residue was purified by silica gel chromatography (1-10% ethyl acetate in petroleum ether) to afford the title compound as a liquid.
MS=265.9/267.9 (M).

Step 3: 2-(2-Chloro-4-(trifluoromethyl)phenyl)propanal

To a solution of methyl 2-(2-chloro-4-(trifluoromethyl) phenyl)propanoate (490 mg, 1.838 mmol) in THF (3 ml) under nitrogen was added DIBAL-H in hexane (2.76 ml, 2.76 mmol) dropwise with stirring at −75° C. and stirred for 1 h. The reaction mixture was quenched with saturated ammonium chloride solution (10 mL) and extracted with ethyl acetate (3×10 mL). The combined organic extracts were washed with brine (10 mL), dried over anhydrous sodium sulfate, and filtered. The filtrate was concentrated under reduced pressure. The residue was purified by silica gel chromatography (1-15% ethyl acetate in petroleum ether) to furnish the title compound. MS=235.9/237.8 (M).

Step 4: 1-(But-3-yn-2-yl)-2-chloro-4-(trifluoromethyl)benzene

To a solution of 2-(2-chloro-4-(trifluoromethyl)phenyl) propanal (200 mg, 0.845 mmol) in MeOH (4 ml) was added dimethyl (1-diazo-2-oxopropyl)phosphonate (195 mg, 1.014 mmol) with stirring at 0° C. followed by potassium carbonate (234 mg, 1.690 mmol). The mixture was then warmed to 25° C. and stirred for 16 h. The reaction mixture was quenched by water (10 mL) and extracted with ethyl acetate (3×10 mL). The combined organic extracts were washed with brine (10 mL), dried over anhydrous sodium sulfate, and filtered. The filtrate was concentrated under reduced pressure and the residue was purified by silica gel chromatography (1-5% ethyl acetate in petroleum ether) to furnish the title compound as a liquid. MS=231.9/233.9 (M).

Step 5: 4-(4-(1-(2-Chloro-4-(trifluoromethyl)phenyl)ethyl)-1H-1,2,3-triazol-1-yl)-6-methoxy-2-methylpyrimidine To a solution of 4-chloro-6-methoxy-2-methylpyrimidine (400 mg, 2.52 mmol) in DMF (4 ml) was added sodium azide (246 mg, 3.78 mmol) at 90° C. The reaction solution was stirred at 90° C. overnight. The reaction was cooled, diluted with water (10 mL), and extracted with ethyl acetate (3×10 mL). The combined organic extracts were washed with brine (2×10 mL), dried over anhydrous sodium sulfate, and filtered. The filtrate was concentrated under vacuum to give 4-azido-6-methoxy-2-methylpyrimidine which was used without further purification.

To a solution of 1-(but-3-yn-2-yl)-2-chloro-4-(trifluoromethyl)benzene (21.13 mg, 0.091 mmol) in DMF (1 ml), Water (0.5 ml) was added copper(II) sulfate pentahydrate (4.54 mg, 0.018 mmol), sodium ascorbate (7.20 mg, 0.036 mmol), and 4-azido-6-methoxy-2-methylpyrimidine (50 mg, 0.303 mmol) at RT. The reaction solution was stirred at 85° C. for 3 h. The reaction mixture was cooled, diluted with water (10 mL) and extracted with ethyl acetate (3×10 mL). The combined organic extracts were washed with brine (2×15 mL), dried over anhydrous sodium sulfate, and filtered. The filtrate was concentrated under vacuum. The residue was purified by silica gel chromatography (12% ethyl acetate in petroleum ether) to furnish the title compound as a solid. MS=398.1 (M+1).

Step 6: (R)- and (S)-6-(4-(1-(2-Chloro-4-(trifluoromethyl)phenyl)ethyl)-1H-1,2,3-triazol-1-yl)-2-methylpyrimidin-4(3H)-one To a solution of 4-(4-(1-(2-chloro-4-(trifluoromethyl)phenyl)ethyl)-1H-1,2,3-triazol-1-yl)-6-methoxy-2-methylpyrimidine (60 mg, 0.151 mmol) in DMSO (1 ml) was added sodium cyanide (37.0 mg, 0.754 mmol) at RT. The reaction was stirred at 130° C. for 1 h. The reaction was cooled, diluted with water (10 mL) and extracted with ethyl acetate (2×10 mL). The combined organic extracts were washed with brine (2×10 mL), dried over anhydrous sodium sulfate, and filtered. The filtrate was concentrated under vacuum. The residue was purified by silica gel chromatography (20% ethyl acetate in petroleum ether) to furnish the racemic title compound as a solid. The racemic title compound was separated into the enantiopure title compounds by chiral HPLC (Chiralpak IC; 20% ethanol in hexanes). The faster-eluting enantiomer of the title compound (Example 74): $^1$H NMR (400 MHz, CD$_3$COD): δ 8.49 (d, J=0.4 Hz, 1H), 7.75 (s, 1H), 7.60 (d, J=8.4 Hz, 1H), 7.52 (d, J=8.4 Hz, 1H), 6.91 (s, 1H), 4.90 (q, J=7.2 Hz, 1H), 2.48 (s, 3H), 1.74 (d, J=7.2 Hz, 3H). MS=381.9 (M−1). The slower-eluting enantiomer of the title compound (Example 75): $^1$H NMR (400 MHz, CD$_3$COD): δ 8.49 (d, J=0.4 Hz, 1H), 7.75 (s, 1H), 7.60 (d, J=8.4 Hz, 1H), 7.52 (d, J=8.4 Hz, 1H), 6.91 (s, 1H), 4.90 (q, J=7.2 Hz, 1H), 2.48 (s, 3H), 1.74 (d, J=7.2 Hz, 3H). MS=381.9 (M−1).

Examples 76 and 77

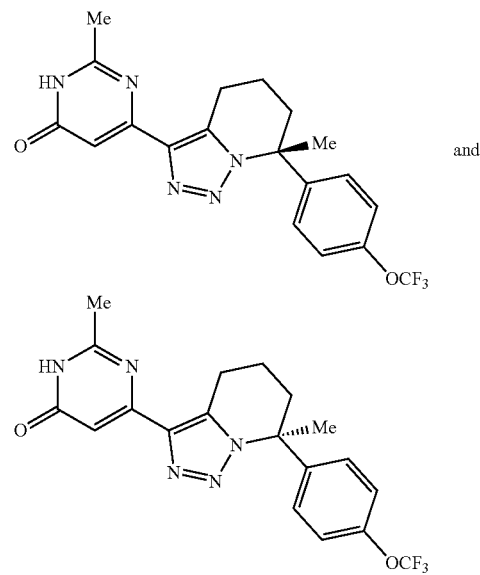

(R)- and (S)-2-Methyl-6-(7-methyl-7-(4-(trifluoromethoxy)phenyl)-4,5,6,7-tetrahydro-[1,2,3]triazolo[1,5-a]pyridin-3-yl)pyrimidin-4(3H)-one (Scheme 14)

The following compounds were prepared using procedures similar to those described for Examples 54 and 55 following scheme 14 using the appropriate starting materials. The racemic title compound was separated into the enantiopure title compounds by chiral HPLC (Chiralpak IA; 30% ethanol in hexanes). The faster-eluting enantiomer of the title compound (Example 76): $^1$H NMR (300 MHz, CD$_3$OD) δ: 7.20 (d, J=8.1 Hz, 2H), 6.93-6.87 (m, 3H), 3.53-3.40 (m, 1H), 3.17-3.02 (m, 1H), 2.49-2.40 (m, 1H), 2.41 (s, 3H), 2.29-2.16 (m, 1H), 2.13 (s, 3H), 1.94-1.81 (m, 1H), 1.56-1.39 (m, 1H). MS (+ESI) m/z=406.0. The slower-eluting enantiomer of the title compound (Example 77): $^1$H NMR (300 MHz, CD$_3$OD) δ: 7.20 (d, J=9.0 Hz, 2H), 6.94-6.86 (m, 3H), 3.53-3.41 (m, 1H), 3.18-3.02 (m, 1H), 2.50-2.38 (m, 1H), 2.41 (s, 3H), 2.30-2.16 (m, 1H), 2.13 (s, 3H), 1.94-1.81 (m, 1H), 1.57-1.39 (m, 1H). MS (+ESI) m/z=406.0.

Examples 78 and 79

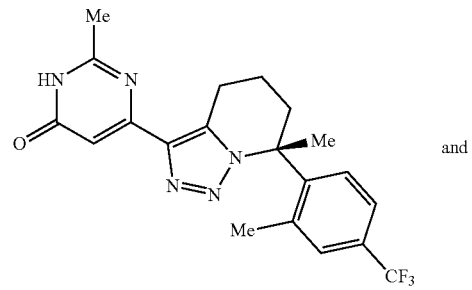

-continued

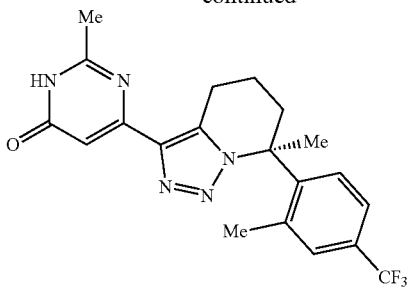

(R)- and (S)-2-Methyl-6-(7-methyl-7-(2-methyl-4-(trifluoromethyl)phenyl)-4,5,6,7-tetrahydro-[1,2,3]triazolo[1,5-a]pyridin-3-yl)pyrimidin-4(3H)-one
(Scheme 14)

The following compounds were prepared using procedures similar to those described for Examples 54 and 55 following scheme 14 using the appropriate starting materials. The racemic title compound was separated into the enantiopure title compounds by chiral HPLC (Lux Cellulose; 30% ethanol in hexanes+0.2% diethylamine). The faster-eluting enantiomer of the title compound (Example 78): $^1$H NMR (300 MHz, MeOD-$d_4$) δ ppm 7.52-7.49 (m, 1H), 7.42-7.39 (m, 2H), 6.88 (s, 1H), 3.66-3.50 (m, 1H), 3.19-3.04 (m, 1H), 2.53-2.43 (m, 1H), 2.40 (s, 3H), 2.17-2.09 (m, 4H), 2.06-1.89 (m, 2H), 1.78 (s, 3H); MS (ES, m/z): 404.0 (M+1). The slower-eluting enantiomer of the title compound (Example 79): $^1$H NMR (300 MHz, MeOD-$d_4$) δ 7.52-7.49 (m, 1H), 7.42-7.39 (m, 2H), 6.88 (s, 1H), 3.66-3.50 (m, 1H), 3.19-3.04 (m, 1H), 2.53-2.43 (m, 1H), 2.40 (s, 3H), 2.17-2.09 (m, 4H), 2.06-1.89 (m, 2H), 1.78 (s, 3H); MS (ES, m/z): 404.0 (M+1).

Examples 80 and 81

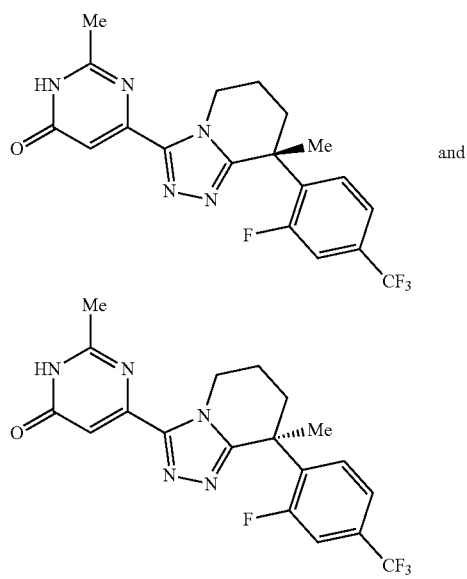

(R)- and (S)-6-(8-(2-Fluoro-4-(trifluoromethyl)phenyl)-8-methyl-5,6,7,8-tetrahydro-[1,2,4]triazolo[4,3-a]pyridin-3-yl)-2-methylpyrimidin-4(3H)-one
(Scheme 18)

Step 1. Methyl 2-(2-fluoro-4-(trifluoromethyl)phenyl)acetate

To a stirred solution of 2-(2-fluoro-4-(trifluoromethyl)phenyl)acetic acid (2.00 g, 9.00 mmol) in MeOH (8 mL) was added concentrated sulfuric acid (8.83 mg, 0.0900 mmol) at RT. The reaction was stirred at 65° C. for 3 h. The mixture was concentrated under reduced pressure. The residue was purified by silica gel chromatography (1-10% of ethyl acetate in petroleum ether). The fractions containing desired product were combined and concentrated. The title compound was obtained as a liquid. $^1$H NMR (400 MHz, CDCl$_3$) δ: 7.43-7.38 (m, 2H), 7.35-7.33 (m, 1H), 3.72 (s, 3H), 3.73 (s, 2H).

Step 2. Methyl 5-chloro-2-(2-fluoro-4-(trifluoromethyl)phenyl)pentanoate

To a stirred mixture of methyl 2-(2-fluoro-4-(trifluoromethyl)phenyl)acetate (2.00 g, 8.47 mmol) in DMF (10 mL) was added sodium hydride (0.373 g, 9.32 mmol) at 0° C. Then 1-chloro-3-iodopropane (2.60 g, 12.7 mmol) was added to the reaction mixture at 0° C. and the reaction mixture was stirred at 25° C. for 16 h. The resulting mixture was then quenched by the addition of water (40 mL) and the product was extracted with ethyl acetate (3×40 mL). The combined extracts were washed with brine (40 mL), dried over anhydrous Na$_2$SO$_4$, and filtered. The filtrate was concentrated under reduced pressure. The residue was purified by silica gel chromatography (1-10% of ethyl acetate in petroleum ether). The fractions containing desired product were combined and concentrated. The title compound was obtained as a liquid. $^1$H NMR (400 MHz, CDCl$_3$) δ: 7.52-7.43 (m, 1H), 7.42-7.40 (m, 1H), 7.35-7.33 (m, 1H), 3.99 (t, J=7.6 Hz, 1H), 3.71 (s, 3H), 3.54 (t, J=6.4 Hz, 2H), 2.35-2.18 (m, 1H), 2.05-1.89 (m, 1H), 1.85-1.59 (m, 2H).

Step 3. 5-Chloro-2-(2-fluoro-4-(trifluoromethyl)phenyl)-2-methylpentanoate

To a stirred solution of diisopropylamine (1.13 g, 11.2 mmol) in THF (15 mL) was added n-butyllithium (2.5 M in hexane, 4.48 mL, 11.2 mmol) dropwise under nitrogen atmosphere at 0° C. The reaction solution was stirred at 0° C. for 40 min. To this reaction solution was added methyl 5-chloro-2-(2-fluoro-4-(trifluoromethyl)phenyl)pentanoate (1.40 g, 4.48 mmol) at −78° C. and stirred at −78° C. for 1 h. Then iodomethane (1.91 g, 13.4 mmol) was added to the reaction mixture and the reaction solution was stirred at −78° C. for 4 h. The resulting mixture was then quenched by saturated aqueous NH$_4$Cl (40 mL) and extracted with ethyl acetate (3×40 mL). The combined organic layers was washed with brine (40 mL), dried over anhydrous Na$_2$SO$_4$ and filtered. The filtrate was concentrated under reduced pressure. The residue was purified by silica gel chromatography (1-10% of ethyl acetate in petroleum ether). The title compound was obtained as a liquid. MS (EI) m/z=326.0; 328.0.

Step 4. 5-Chloro-2-(2-fluoro-4-(trifluoromethyl)phenyl)-2-methylpentanoic Acid

To a stirred mixture of methyl 5-chloro-2-(2-fluoro-4-(trifluoromethyl)phenyl)-2-methylpentanoate (1.20 g, 3.67 mmol) in water (5 mL) was added saturated hydrogen chloride in 1,4-dioxane (10 mL) at RT. The reaction was stirred at 100° C. for 7 d. The reaction mixture was then quenched with water (30 mL) and extracted with ethyl acetate (3×30 mL). The combined extracts were washed with brine (30 mL), dried over anhydrous $Na_2SO_4$, and filtered. The filtrate was concentrated under reduced pressure. The residue was purified by silica gel chromatography (1-50% of ethyl acetate in petroleum ether). The fractions containing the desired product were combined and concentrated. The title compound was obtained as a liquid.

Step 5. N-(5-chloro-2-(2-fluoro-4-(trifluoromethyl) phenyl)-2-methylpentanoyl)-2-methyl-6-oxo-1,6-dihydropyrimidine-4-carbohydrazide To a stirred mixture of 5-chloro-2-(2-fluoro-4-(trifluoromethyl)phenyl)-2-methylpentanoic acid (0.200 g, 0.640 mmol) in NMP (2 mL) was added 2-methyl-6-oxo-1,6-dihydropyrimidine-4-carbohydrazide hydrochloride (0.262 g, 1.28 mmol) at RT. Then HATU (0.486 g, 1.28 mmol) and triethylamine (0.227 g, 2.24 mmol) were added to the reaction mixture and the reaction solution was stirred at 25° C. for 16 h. The resulting mixture was then quenched with water (10 mL) and extracted with ethyl acetate (3×10 mL). The combined extracts were washed with brine (10 mL), dried over anhydrous $Na_2SO_4$ and filtered. The filtrate was concentrated under reduced pressure. The residue was purified by silica gel chromatography (1-100% of ethyl acetate in petroleum ether). The fractions containing the desired product were combined and concentrated. The title compound was obtained as a liquid. MS (+ESI) m/z=463.2; 465.2.

Step 6. 6-(5-(5-Chloro-2-(2-fluoro-4-(trifluoromethyl)phenyl)pentan-2-yl)-1,3,4-oxadiazol-2-yl)-2-methylpyrimidin-4(3H)-one To a stirred mixture of N-(5-chloro-2-(2-fluoro-4-(trifluoromethyl)phenyl)-2-methylpentanoyl)-2-methyl-6-oxo-1,6-dihydropyrimidine-4-carbohydrazide (0.180 g, 0.389 mmol) in 1,4-dioxane (2 mL) was added methyl N-(triethylammoniosulfonyl)carbamate (93.0 mg, 0.389 mmol) at RT. The reaction was stirred at 100° C. for 1 h. The reaction mixture was cooled to RT, quenched with water (10 mL), and extracted with ethyl acetate (3×10 mL). The combined extracts were washed with brine (10 mL), dried over anhydrous $Na_2SO_4$, and filtered. The filtrate was concentrated under reduced pressure. The residue was purified by silica gel chromatography (1-100% of ethyl acetate in petroleum ether). The fractions containing the desired product were combined and concentrated. The title compound was obtained as a liquid. MS (+ESI) m/z=445.3; 447.3.

Step 7. 6-(5-(5-Azido-2-(2-fluoro-4-(trifluoromethyl)phenyl)pentan-2-yl)-1,3,4-oxadiazol-2-yl)-2-methylpyrimidin-4(3H)-one To a stirred solution of 6-(5-(5-chloro-2-(2-fluoro-4-(trifluoromethyl)phenyl)pentan-2-yl)-1,3,4-oxadiazol-2-yl)-2-methylpyrimidin-4(3H)-one (0.160 g, 0.360 mmol) in DMSO (0.5 mL) was added sodium azide (46.8 mg, 0.719 mmol) at RT. The reaction mixture was stirred at 100° C. for 3 h. The reaction mixture was cooled to RT, quenched with saturated aqueous $NaHCO_3$ (30 mL), and extracted with ethyl acetate (3×20 mL). The combined extracts were washed with brine (20 mL), dried over anhydrous $Na_2SO_4$, and filtered. The filtrate was concentrated under reduced pressure. The residue was purified by silica gel chromatography (1-100% of ethyl acetate in petroleum ether). The fractions containing the desired product were combined and concentrated. The title compound was obtained as a solid. MS (+ESI) m/z=452.3.

Step 8. 6-(5-(5-Amino-2-(2-fluoro-4-(trifluoromethyl)phenyl)pentan-2-yl)-1,3,4-oxadiazol-2-yl)-2-methylpyrimidin-4(3H)-one To a stirred mixture of 6-(5-(5-azido-2-(2-fluoro-4-(trifluoromethyl)phenyl)pentan-2-yl)-1,3,4-oxadiazol-2-yl)-2-methylpyrimidin-4(3H)-one (90.0 mg, 0.199 mmol) in methanol (1.5 mL) was added palladium 10% on carbon (0.212 g, 0.199 mmol) at RT. The reaction mixture was degassed with hydrogen 3 times and stirred under a balloon of hydrogen at 25° C. for 2 h. The solid was filtered and the filtrate was concentrated under reduced pressure. The residue was purified by silica gel chromatography (1-100% of methanol (0.1% TEA) in DCM). The fractions containing the desired product were combined and concentrated. The title compound was obtained as a solid. MS (+ESI) m/z=426.2.

Step 9. 6-(8-(2-Fluoro-4-(trifluoromethyl)phenyl)-8-methyl-5,6,7,8-tetrahydro-[1,2,4]triazolo[4,3-c]pyridin-3-yl)-2-methylpyrimidin-4(3H)-one 6-(5-(5-Amino-2-(2-fluoro-4-(trifluoromethyl)phenyl) pentan-2-yl)-1,3,4-oxadiazol-2-yl)-2-methylpyrimidin-4 (3H)-one (45.0 mg, 0.106 mmol) was added to acetic acid (3 mL, 52.4 mmol) at RT. The reaction mixture was stirred at 100° C. for 4 h. The resulting mixture was cooled to RT and concentrated under reduced pressure. The residue was purified by preparative HPLC (X Bridge C-18 OBD Prep Column; 20%-80% acetonitrile in water). The fractions containing the desired product were combined and concentrated. The title compound was obtained as a solid. MS (+ESI) m/z=408.2.

Step 10. (R)- and (S)-6-(8-(2-fluoro-4-(trifluoromethyl)phenyl)-8-methyl-5,6,7,8-tetrahydro-[1,2,4] triazolo[4,3-a]pyridin-3-yl)-2-methylpyrimidin-4 (3H)-one The 6-(8-(2-fluoro-4-(trifluoromethyl)phenyl)-8-methyl-5,6,7,8-tetrahydro-[1,2,4]triazolo[4,3-a]-pyridin-3-yl)-2-methylpyrimidin-4(3H)-one (40.0 mg, 0.0980 mmol) was separated by Chiral HPLC (Chiralpak IC column; 50% EtOH in hexanes). The faster-eluting enantiomer of the title compound (Example 80) was obtained as a solid. $^1$H NMR (400 MHz, $CD_3OD$) δ: 7.52-7.41 (m, 3H), 7.01 (s, 1H), 4.73-4.67 (m, 1H), 4.48-4.38 (m, 1H), 2.49 (s, 3H), 2.48-2.39 (m, 1H), 2.16-1.98 (m, 3H), 1.94 (s, 3H). MS (+ESI) m/z=408.2. The slower-eluting enantiomer of the title compound (Example 81) was obtained as a solid. $^1$H NMR (400 MHz, $CD_3OD$) δ: 7.50-7.41 (m, 3H), 7.01 (s, 1H), 4.76-4.63 (m, 1H), 4.52-4.38 (m, 1H), 2.49 (s, 3H), 2.45-2.38 (m, 1H), 2.20-1.95 (m, 3H), 1.94 (s, 3H); MS (+ESI) m/z=408.2.

Examples 82 and 83

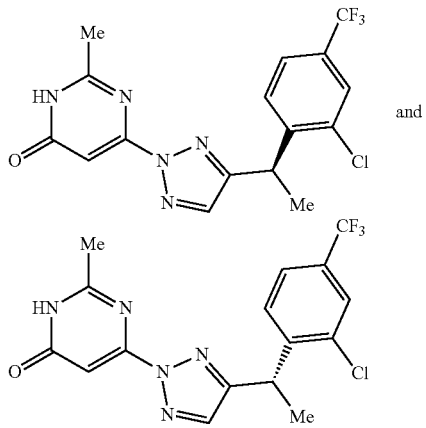

(R)- and (S)-6-(4-(1-(2-Chloro-4-(trifluoromethyl)
phenyl)ethyl)-2H-1,2,3-triazol-2-yl)-2-methylpy-
rimidin-4(3H)-one (Scheme 19)

Step 1. Methyl
2-(2-chloro-4-(trifluoromethyl)phenyl)propanoate

Into a solution of methyl 2-(2-chloro-4-(trifluoromethyl) phenyl)acetate (3.0 g, 11.88 mmol) in DMF (20 ml) was added sodium hydride (0.570 g, 14.25 mmol) with stirring at 0° C. Then the reaction mixture was warmed to 25° C. and stirred for 0.5 h. Then iodomethane (1.938 g, 13.66 mmol) was added with stirring at 0° C. The reaction mixture was warmed to 25° C. and stirred for 16 h. The reaction mixture was diluted with water (15 mL) and extracted with ethyl acetate (3×15 mL). The combined organic extracts were washed with brine (1×15 mL), dried over anhydrous sodium sulfate, and filtered. The filtrate was concentrated under reduced pressure. The residue was purified by silica gel column chromatography (1-10% ethyl acetate in petroleum ether) to afford the title compound as a liquid. GCMS=266 (M).

Step 2.
2-(2-Chloro-4-(trifluoromethyl)phenyl)propanal

To a solution of methyl 2-(2-chloro-4-(trifluoromethyl) phenyl)propanoate (1.687 g, 6.33 mmol) in tetrahydrofuran (5 ml) under nitrogen was added DIBAL-H in hexane (9.49 ml, 9.49 mmol) dropwise with stirring at −75° C. After stirring for 1 h, the reaction mixture was quenched with saturated aqueous ammonium chloride solution (15 mL) and extracted with ethyl acetate (3×10 mL). The combined organic extracts were washed with brine (10 mL), dried over anhydrous sodium sulfate, and filtered. The filtrate was concentrated under reduced pressure. The residue was purified by silica gel column chromatography (1-15% ethyl acetate in petroleum ether) to afford the title compound as a liquid. GCMS=236 (M).

Step 3. 1-(But-3-yn-2-yl)-2-chloro-4-(trifluorom-
ethyl)benzene

To a solution of 2-(2-chloro-4-(trifluoromethyl)phenyl) propanal (1.086 g, 4.59 mmol) in methanol (5 ml) was added dimethyl (1-diazo-2-oxopropyl)phosphonate (1.058 g, 5.51 mmol) with stirring at 0° C. followed by potassium carbonate (1.269 g, 9.18 mmol). The reaction mixture was then warmed to 25° C. and stirred for 16 h. The reaction mixture was quenched with water (15 mL) and extracted with ethyl acetate (3×10 mL). The combined organic extracts were washed with brine (10 mL), dried over anhydrous sodium sulfate, and filtered. The filtrate was concentrated under reduced pressure and the residue was purified by silica gel column chromatography (1-5% ethyl acetate in petroleum ether) to afford the title compound as a liquid. GCMS=232 (M).

Step 4. 4-(1-(2-Chloro-4-(trifluoromethyl)phenyl)
ethyl)-2H-1,2,3-triazole

To a mixture of 1-(but-3-yn-2-yl)-2-chloro-4-(trifluoromethyl)benzene (720 mg, 3.10 mmol), copper sulphate pentahydrate (155 mg, 0.619 mmol) and (R)-5-((S)-1,2-dihydroxyethyl)-3,4-dihydroxyfuran-2(5H)-one, sodium salt (1.23 g, 6.19 mmol) in dimethylformamide (9 ml) and water (3 mL) under nitrogen was added azidotrimethylsilane (2.85 g, 24.76 mmol) dropwise. The mixture was then stirred for 2 h at 90° C. After completion, the reaction mixture was diluted with brine (10 mL) and extracted with ethyl acetate (3×10 mL). The combined organic extracts were washed with brine (1×10 mL), dried over anhydrous sodium sulfate, and filtered. The filtrate was concentrated under reduced pressure and the residue was purified by silica gel column chromatography (1-40% ethyl acetate in petroleum ether) to afford the title compound as a liquid. MS=275.9 (M+1).

Step 5. 4-Chloro-6-(4-(1-(2-chloro-4-(trifluorom-
ethyl)phenyl)ethyl)-2H-1,2,3-triazol-2-yl)-2-methyl-
pyrimidine To a solution of 4-(1-(2-chloro-4-(trifluoromethyl)phenyl)ethyl)-2H-1,2,3-triazole (545 mg, 1.977 mmol) and 4,6-dichloro-2-methylpyrimidine (483 mg, 2.97 mmol) in DMF (8 ml) was added sodium hydride (119 mg, 4.94 mmol) with stirring at 25° C. After 16 h the reaction mixture was quenched with water (20 mL) and extracted with ethyl acetate (3×10 mL). The combined organic extracts were washed with brine (10 mL), dried over anhydrous sodium sulfate, and filtered. The filtrate was concentrated under reduced pressure. The residue was purified by silica gel column chromatography (1-20% ethyl acetate in petroleum ether) to afford the title compound as a liquid. MS=401.9 (M+1).

Step 6. (R)- and (S)-6-(4(1-(2-Chloro-4-(trifluorom-
ethyl)phenyl)ethyl)-2H-1,2,3-triazol-2-yl)-2-methyl-
pyrimidin-4(3H)-one To a stirring solution of 4-chloro-6-(4-(1-(2-chloro-4-(trifluoromethyl)phenyl)ethyl)-2H-1,2,3-triazol-2-yl)-2-methylpyrimidine (68 mg, 0.169 mmol) in NMP (1.2 ml) and water (1.2 ml) was added potassium hydroxide (28.5 mg, 0.507 mmol) at 25° C. After 16 h, the reaction mixture was diluted with brine (10 mL) and extracted with ethyl acetate (3×10 mL). The combined organic extracts were washed with brine (1×10 mL), dried over anhydrous sodium sulfate, and filtered. The filtrate was concentrated under reduced pressure and the crude product was purified by reverse phase HPLC (GILSON (GX-281); Xbridge RP18 column; 35-60% acetonitrile in water+0.05% NH$_4$CO$_3$) to afford the racemic title compound. The racemic title compound was separated into its enantiomers by Chiral-Prep-HPLC (CHIRALCEL OJ-H column; 5-35% ethanol in hexane). The faster eluting enantiomer (Example 82) was obtained as a solid. $^1$H NMR (300 MHz, CD$_3$OD-d$_4$) δ: 7.90 (s, 1H), 7.73 (s, 1H), 7.60-7.51 (m, 2H), 6.77 (s, 1H), 4.95-4.90 (m, 1H), 2.46 (s, 3H), 1.73 (d, J=7.2 Hz, 3H). LCMS=384.0 (M+1). The slower-eluting enantiomer (Example 83) was obtained as a solid. $^1$H NMR (300 MHz, CD$_3$OD-d$_4$) δ: 7.90 (s, 1H), 7.73 (s, 1H), 7.60-7.51 (m, 2H), 6.77 (s, 1H), 4.95-4.90 (m, 1H), 2.46 (s, 3H), 1.73 (d, J=7.2 Hz, 3H). LCMS=384.0 (M+1).

Examples 84 and 85

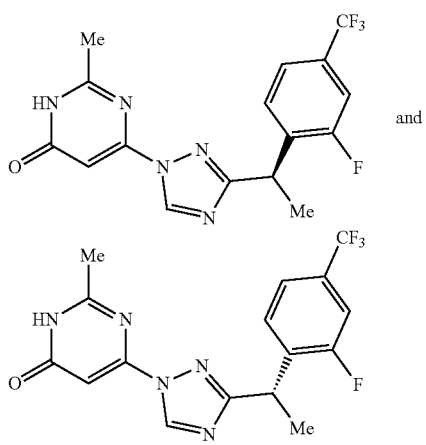

(R)- and (S)-6-(3-(1-(2-Fluoro-4-(trifluoromethyl)phenyl)ethyl)-1H-1,2,4-triazol-1-yl)-2-methylpyrimidin-4(3H)-one (Scheme 20)

Step 1.
2-(2-Fluoro-4-(trifluoromethyl)phenyl)propanamide

A solution of ammonia in DCM was added dropwise to a solution of 2-(2-fluoro-4-(trifluoromethyl)phenyl)propanoyl chloride (1.2 g, 4.71 mmol) in DCM (10 ml) cooled to 0° C. The solution was stirred for 1 h at 0° C. The solution was concentrated under vacuum to afford the title compound as a solid. LCMS=235.9 (M+1).

Step 2. 3-(1-(2-Fluoro-4-(trifluoromethyl)phenyl)ethyl)-1H-1,2,4-triazole 2-(2-Fluoro-4-(trifluoromethyl)phenyl)propanamide (200 mg, 0.850 mmol) was dissolved in N,N-dimethylformamide dimethyl acetal (2027 mg, 17.01 mmol) and the resulting solution was stirred for 2 h at 90° C. The solution was concentrated under vacuum. The residue was dissolved in acetic acid (3 ml) and hydrazine hydrate (0.083 ml, 1.701 mmol). The solution was stirred for 2 h at 90° C. The resulting mixture was diluted with water (10 mL) and extracted with ethyl acetate (3×20 mL). The combined organic extracts were washed with brine (10 mL), dried over anhydrous sodium sulfate, and filtered. The filtrate was concentrated under vacuum. The residue was purified by silica gel chromatography (0-40% ethyl acetate in petroleum ether) to afford the title compound as an oil. LCMS=260.0 (M+1).

Step 3. 4-Chloro-6-(3-(1-(2-fluoro-4-(trifluoromethyl)phenyl)ethyl)-1H-1,2,4-triazol-1-yl)-2-methylpyrimidine 4,6-Dichloro-2-methylpyrimidine (34.6 mg, 0.212 mmol) and cesium carbonate (126 mg, 0.386 mmol) were added to a solution of 3-(1-(2-fluoro-4-(trifluoromethyl)phenyl)ethyl)-1H-1,2,4-triazole (50 mg, 0.193 mmol) in DMF (1.5 ml). The mixture was stirred for 2 h at RT. The resulting mixture was diluted with water (5 mL) and extracted with ethyl acetate (3×10 mL). The combined organic extracts were washed with brine (5 mL), dried over anhydrous sodium sulfate, and filtered. The filtrate was concentrated under vacuum and the residue was purified by silica gel chromatography (0-30% ethyl acetate in petroleum ether) to afford the title compound as an oil. LCMS=386.0 (M+1).

Step 4. (R)- and (S)-6-(3-(1-(2-Fluoro-4-(trifluoromethyl)phenyl)ethyl)-1H-1,2,4-triazol-1-yl)-2-methylpyrimidin-4(3H)-one To a solution of 4-chloro-6-(3-(1-(2-fluoro-4-(trifluoromethyl)phenyl)ethyl)-1H-1,2,4-triazol-1-yl)-2-methylpyrimidine (20 mg, 0.052 mmol) in NMP (0.5 ml) was added potassium hydroxide (2.91 mg, 0.052 mmol). The solution was stirred for 2 h at RT. The resulting mixture was diluted with water (5 mL) and extracted with ethyl acetate (3×10 mL). The combined organic extracts were washed with brine (5 mL), dried over anhydrous sodium sulfate, and filtered. The filtrate was concentrated under vacuum and the residue was purified by silica gel chromatography (0-30% ethyl acetate in petroleum ether) to afford the racemic title compound as an oil. The racemic title compound was then separated into its enantiomers by chiral chromatography (CHIRALPAK-AD-H; 7% ethanol in hexane). The faster eluting enantiomer (Example 84) was obtained as a solid. $^1$H NMR (400 MHz, CD$_3$OD) δ: 9.17 (s, 1H), 7.57-7.54 (m, 1H), 7.48-7.43 (m, 2H), 6.63 (s, 1H), 4.70 (q, J=7.2 Hz, 1H), 2.46 (s, 3H), 1.74 (d, J=7.2 Hz, 3H). LCMS=368.0 (M+1). The slower-eluting enantiomer (Example 85) was obtained as a solid. $^1$H NMR (400 MHz, CD$_3$OD) δ: 9.17 (s, 1H), 7.57-7.54 (m, 1H), 7.48-7.43 (m, 2H), 6.63 (s, 1H), 4.70 (q, J=7.2 Hz, 1H), 2.46 (s, 3H), 1.74 (d, J=7.2 Hz, 3H). LCMS=368.0 (M+1).

Example 86

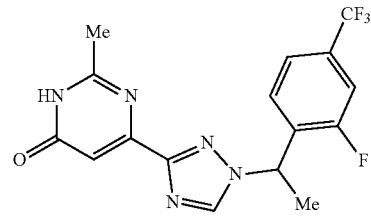 [SMILES: Cc1nc(-c2ncn(C(C)c3ccc(C(F)(F)F)cc3F)n2)cc(=O)[nH]1]

6-(1-(1-(2-Fluoro-4-(trifluoromethyl)phenyl)ethyl)-1H-1,2,4-triazol-3-yl)-2-methylpyrimidin-4(3H)-one (Scheme 21)

Step 1.
6-Methoxy-2-methylpyrimidine-4-carboxamide

NH$_3$ in MeOH (50 ml) was added to methyl 6-methoxy-2-methylpyrimidine-4-carboxylate (1 g, 5.49 mmol) and the mixture was stirred at 25° C. for 16 h. Then hexane (100 mL) was added. The mixture was filtered, and then washed with hexane (50 mL). The solid was dried to afford the title compound as a solid. ¹H NMR (300 MHz, DMSO): 8.09 (s, 1H), 7.88 (s, 1H), 7.15 (s, 1H), 3.95 (s, 3H), 2.60 (s, 3H).

Step 2. 4-Methoxy-2-methyl-6-(1H-1,2,4-triazol-3-yl)pyrimidine

A solution of 6-methoxy-2-methylpyrimidine-4-carboxamide (200 mg, 1.196 mmol) in dimethylformamide dimethyl acetal (2 mL) was stirred at 130° C. for 6 h under an atmosphere of nitrogen. The resulting mixture was cooled and concentrated under reduced pressure to give a semisolid. The residue was dissolved in acetic acid (2 mL) and treated with hydrazine (59.6 mg, 1.822 mmol) at RT. The reaction mixture was stirred at 80° C. for 0.5 h under an atmosphere of nitrogen. The resulting mixture was cooled and filtered through celite. The filtrate was concentrated under reduced pressure, diluted with ethyl acetate (100 mL), washed with brine (2×100 mL), dried with anhydrous Na₂SO₄, and filtered. The filtrate was concentrated under reduced pressure to afford the title compound as a solid. LCMS=192.0 (M+1).

Step 3. 4-(1-(1-(2-Fluoro-4-(trifluoromethyl)phenyl) ethyl)-1H-1,2,4-triazol-3-yl)-6-methoxy-2-methylpyrimidine To a solution of 4-methoxy-2-methyl-6-(1H-1,2,4-triazol-3-yl)pyrimidine (170 mg, 0.889 mmol) in THF (2 mL) were added 1-(2-fluoro-4-(trifluoromethyl)phenyl)ethanol (241 mg, 1.156 mmol) and triphenylphosphine (583 mg, 2.223 mmol). The mixture was stirred for 5 minutes and DIAD (0.432 mL, 2.223 mmol) was added dropwise at 0° C. under an atmosphere of nitrogen. The reaction mixture was stirred at 0° C. for 1 h. The reaction mixture was diluted with brine (30 mL), extracted with ethyl acetate (2×30 mL), and the combined organic extracts were dried over anhydrous sodium sulfate and filtered. The filtrate was concentrated under reduced pressure and the residue was purified by silica gel chromatography (43% ethyl acetate in petroleum ether) to afford the title compound as a solid. LCMS=382.0 (M+1).

Step 4. 6-(1-(1-(2-Fluoro-4-(trifluoromethyl)phenyl) ethyl)-1H-1,2,4-triazol-3-yl)-2-methylpyrimidin-4 (3H)-one A solution of 4-(4-(1-(2-fluoro-4-(trifluoromethyl)phenyl)ethyl)-4H-1,2,4-triazol-3-yl)-6-methoxy-2-methylpyrimidine (30 mg, 0.079 mmol) in HCl in dioxane (4 N; 1 mL) was stirred at 80° C. for 24 h under an atmosphere of nitrogen. The reaction was cooled to RT, diluted with ethyl acetate (20 mL), washed with brine (2×20 mL), dried over anhydrous sodium sulfate, and filtered. The filtrate was concentrated under reduce pressure to afford the title compound as a solid. ¹H NMR (400 MHz, DMSO-d₆) δ: 8.89 (s, 1H), 7.75-7.69 (m, 1H), 7.66-7.58 (m, 1H), 7.55-7.52 (m, 1H), 6.73 (s, 1H), 6.11 (q, J=6.8 Hz, 1H), 2.31 (s, 3H), 1.89 (d, J=7.2 Hz, 3H). LCMS=368.0 (M+1).

Examples 87 and 88

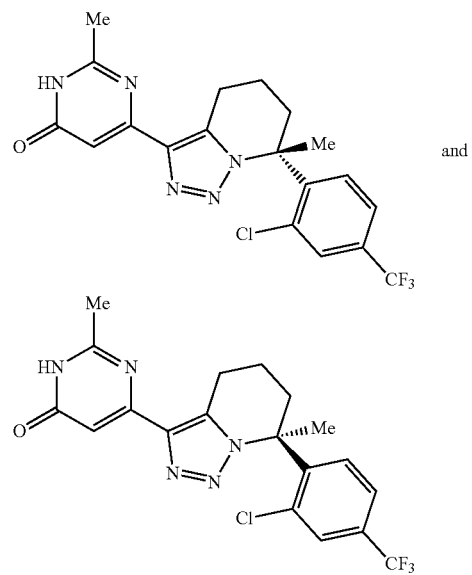

(R)- and (S)-6-(7-(2-Chloro-4-(trifluoromethyl)phenyl)-7-methyl-4,5,6,7-tetrahydro-[1,2,3]triazolo[1,5-a]pyridin-3-yl)-2-methylpyrimidin-4(3H)-one (Scheme 14)

Steps 1-6. 2-(2-Chloro-4-(trifluoromethyl)phenyl)-7-(6-((4-methoxybenzyl)oxy)-2-methylpyrimidin-4-yl)hept-6-yn-2-ol The procedures outlined for steps 1 through 6 used for the synthesis of examples 54 and 55 as in Scheme 14 employing the appropriate starting materials were followed to afford the title compound. LCMS=519.3 (M+1).

Step 7. (R)- and (S)-6-(7-(2-chloro-4-(trifluoromethyl)phenyl)-7-methyl-4,5,6,7-tetrahydro-[1,2,3] triazolo[1,5-a]pyridin-3-yl)-2-methylpyrimidin-4 (3H)-one BF₃.OEt₂ (0.820 mL, 6.47 mmol) was added dropwise to a stirred solution of 2-(2-chloro-4-(trifluoromethyl)phenyl)-7-(6-((4-methoxybenzyl)oxy)-2-methylpyrimidin-4-yl) hept-6-yn-2-ol (0.560 g, 1.079 mmol) and TMS-N₃ (0.573 mL, 4.32 mmol) in toluene (4 mL) cooled to 0° C. The reaction was stirred at RT for 30 minutes. The reaction mixture was stirred for additional 6 h at 110° C. The reaction mixture was cooled, diluted with ethyl acetate (200 mL), washed with brine (2×100 mL), dried with anhydrous sodium sulfate, and filtered. The filtrate was concentrated under reduced pressure and the residue was purified by silica gel chromatography (0-100% ethyl acetate in hexanes) and reverse phase preparative HPLC (X-bridge C-18 column; 30-47% acetonitrile in water+0.05% NH₄HCO₃) to afford the racemic title compound as a solid. The racemic title compound was then separated into its enantiomers using chiral chromatography (Chiralpak IC column; 50% ethanol in hexane). The faster-eluting enantiomer (Example 87) of the title compound was obtained as a solid. ¹H NMR (400 MHz, CD₃OD) δ: 7.73 (s, 1H), 7.67 (d, J=8.4 Hz, 1H), 7.43

(d, J=8.4 Hz, 1H), 6.90 (s, 1H), 3.62-3.55 (m, 1H), 3.24-3.15 (m, 1H), 2.92-2.85 (m, 1H), 2.45 (s, 3H), 2.22 (s, 3H), 2.16-2.02 (m, 2H), 1.98-1.88 (m, 1H). LCMS=424.1 (M+1). The slower-eluting enantiomer (Example 88) of the title compound was obtained as a solid. $^1$H NMR (400 MHz, CD$_3$OD) δ: 7.73 (s, 1H), 7.67 (d, J=8.4 Hz, 1H), 7.43 (d, J=8.4 Hz, 1H), 6.90 (s, 1H), 3.62-3.54 (m, 1H), 3.24-3.15 (m, 1H), 2.92-2.85 (m, 1H), 2.45 (s, 3H), 2.22 (s, 3H), 2.16-2.02 (m, 2H), 1.98-1.88 (m, 1H). LCMS=424.1 (M+1).

Examples 89 and 90

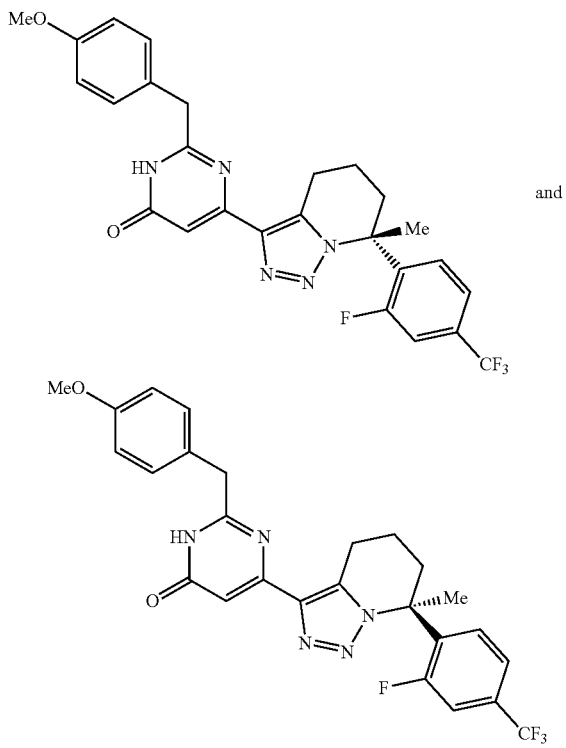

and (R)- and (S)-6-(7-(2-Fluoro-4-(trifluoromethyl)phenyl)-7-methyl-4,5,6,7-tetrahydro-[1,2,3]triazolo[1,5-a]pyridin-3-yl)-2-(4-methoxybenzyl)pyrimidin-4(3H)-one (Scheme 22)

Steps 1-6. 7-(6-Chloro-2-(4-methoxybenzyl)pyrimidin-4-yl)-2-(2-fluoro-4-(trifluoromethyl)phenyl)hept-6-yn-2-ol The procedures outlined for steps 1 through 6 used for the synthesis of examples 54 and 55 as in Scheme 14 employing the appropriate starting materials were followed to afford the title compound. LCMS=507.1 (M+1).

Step 7. 5-(4-(6-Chloro-2-(4-methoxybenzyl)pyrimidin-4-yl)-1-(4-methoxybenzyl)-1H-1,2,3-triazol-5-yl)-2-(2-fluoro-4-(trifluoromethyl)phenyl)pentan-2-ol 7-(6-Chloro-2-(4-methoxybenzyl)pyrimidin-4-yl)-2-(2-fluoro-4-(trifluoromethyl)phenyl)hept-6-yn-2-ol (636 mg, 1.255 mmol), 1-(azidomethyl)-4-methoxybenzene (246 mg, 1.506 mmol), and Pentamethylcyclopentadienylbis(triphenylphosphine)ruthenium(II) chloride (Cp*RuCl(PPh$_3$)$_2$, 999 mg, 1.255 mmol) were combined in toluene (4 ml) and heated to 80° C. for 16 h. The reaction mixture was purified by silica gel chromatography (1-30% ethyl acetate in petroleum ether) to afford the title compound as an oil. LCMS=670.2 (M+1).

Step 8. 6-(5-(4-(2-Fluoro-4-(trifluoromethyl)phenyl)-4-hydroxypentyl)-1-(4-methoxybenzyl)-1H-1,2,3-triazol-4-yl)-2-(4-methoxybenzyl)pyrimidin-4(3H)-one To a mixture of 5-(4-(6-chloro-2-(4-methoxybenzyl)pyrimidin-4-yl)-1-(4-methoxybenzyl)-1H-1,2,3-triazol-5-yl)-2-(2-fluoro-4-(trifluoromethyl)phenyl)pentan-2-ol (520 mg, 0.776 mmol)) in NMP (5 ml) and water (2.5 ml) was added potassium hydroxide (218 mg, 3.88 mmol) and the mixture was stirred for 16 h at 25° C. The solution was extracted with EA (3×10 mL). The combined organic extracts were washed with brine (15 mL) and then dried over sodium sulfate. The solvent was removed under reduced pressure and the residue was purified by silica gel column chromatography (1-80% ethyl acetate in petroleum ether to give the title compound as an oil. LCMS=652.3 (M+1).

Step 9. (R)- and (S)-6-(7-(2-Fluoro-4-(trifluoromethyl)phenyl)-7-methyl-4,5,6,7-tetrahydro-[1,2,3]triazolo[1,5-a]pyridin-3-yl)-2-(4-methoxybenzyl)pyrimidin-4(3H)-one A solution of 6-(5-(4-(2-fluoro-4-(trifluoromethyl)phenyl)-4-hydroxypentyl)-1-(4-methoxybenzyl)-1H-1,2,3-triazol-4-yl)-2-(4-methoxybenzyl)pyrimidin-4(3H)-one (210 mg, 0.322 mmol) in TFA (5 ml) was heated to 80° C. with stirring for 24 h. The reaction mixture was concentrated under reduced pressure and the residue was purified by reverse phase preparative HPLC (X-Bridge C-18 OBD Column; 50-57% acetonitrile in water+0.05% TFA) to afford the racemic title compound as a solid. The racemic title compound was separated into its enantiomers using chiral chromatography (Chiralpak IC, 50% ethanol in hexane). The faster eluting enantiomer (Example 89) was obtained as a solid. $^1$H NMR (300 MHz, DMSO-d$_6$) δ: 12.64-12.55 (m, 1H), 7.68 (d, J=11.7 Hz, 1H), 7.56-7.47 (m, 1H), 7.30-7.20 (m, 2H), 6.91-6.81 (m, 2H), 6.73-6.61 (m, 2H), 3.81 (s, 2H), 3.67 (s, 3H), 3.05-2.94 (m, 2H), 2.45-2.39 (m, 1H), 2.31-2.12 (m, 1H), 2.06 (s, 3H), 1.81 (s, 1H), 1.53-1.17 (m, 1H). LCMS=514.3 (M+1). The slower-eluting enantiomer (Example 90) was obtained as a solid. $^1$H NMR (300 MHz, DMSO-d$_6$) δ: 12.64-12.55 (m, 1H), 7.68 (d, J=11.7 Hz, 1H), 7.56-7.47 (m, 1H), 7.30-7.20 (m, 2H), 6.91-6.81 (m, 2H), 6.73-6.61 (m, 2H), 3.81 (s, 2H), 3.67 (s, 3H), 3.05-2.94 (m, 2H), 2.45-2.39 (m, 1H), 2.31-2.12 (m, 1H), 2.06 (s, 3H), 1.81 (s, 1H), 1.53-1.17 (m, 1H); LCMS=514.3 (M+1).

TABLE 16

The following compounds were prepared using procedures similar to those described for examples 89 and 90 using the appropriate starting materials.

| Example No. | Structure | IUPAC name | Exact Mass [M + H]+ | Chiral Column |
|---|---|---|---|---|
| 91 | 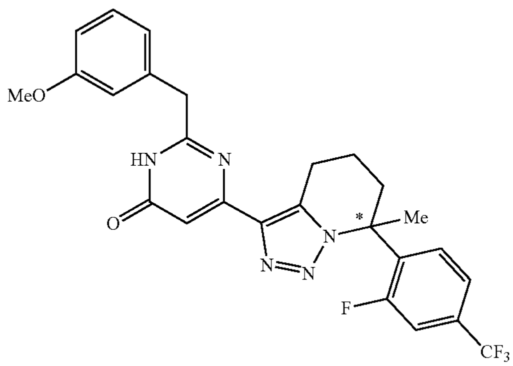 [SMILES: COc1cccc(Cc2nc(-c3nnn4c3CCCC4(C)c3ccc(C(F)(F)F)cc3F)cc(=O)[nH]2)c1] | (S)- or (R)-6-(7-(2-Fluoro-4-(trifluoromethyl)phenyl)-7-methyl-4,5,6,7-tetrahydro-[1,2,3]triazolo[1,5-a]pyridin-3-yl)-2-(3-methoxybenzyl)pyrimidin-4(3H)-one | Calc'd 514.2, found 514.3 | Chiralpak IC |
| 92 | 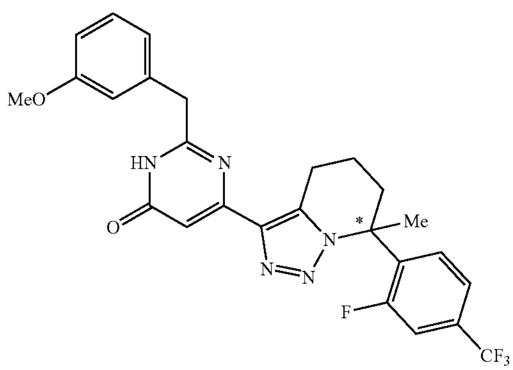 [SMILES: COc1cccc(Cc2nc(-c3nnn4c3CCCC4(C)c3ccc(C(F)(F)F)cc3F)cc(=O)[nH]2)c1] | (R)- or (S)-2-Methyl-6-(8-methyl-8-(4-(trifluoromethyl)phenyl)-5,6,7,8-tetrahydro-[1,2,4]triazolo[4,3-a]pyridin-3-yl)pyrimidin-4(3H)-one | Calc'd 514.2, found 514.3 | Chiralpak IC |
| 93 | 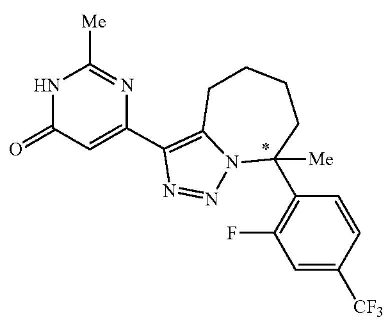 [SMILES: Cc1nc(-c2nnn3c2CCCCC3(C)c2ccc(C(F)(F)F)cc2F)cc(=O)[nH]1] | (S)- or (R)-6-(8-(2-Fluoro-4-(triflouromethyl)phenyl)-8-methyl-5,6,7,8-tetrahydro-4H-[1,2,3]triazolo[1,5-a]azepin-3-yl)-2-methylpyrimidin-4(3H)-one | Calc'd 422.2, found 422.2 | Chiralpak IC |
| 94 | 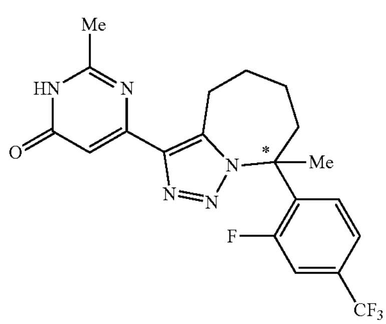 [SMILES: Cc1nc(-c2nnn3c2CCCCC3(C)c2ccc(C(F)(F)F)cc2F)cc(=O)[nH]1] | (S)- or (R)-6-(8-(2-Fluoro-4-(triflouromethyl)phenyl)-8-methyl-5,6,7,8-tetrahydro-4H-[1,2,3]triazolo[1,5-a]azepin-3-yl)-2-methylpyrimidin-4(3H)-one | Calc'd 422.2, found 422.2 | Chiralpak IC |

Examples 95 and 96

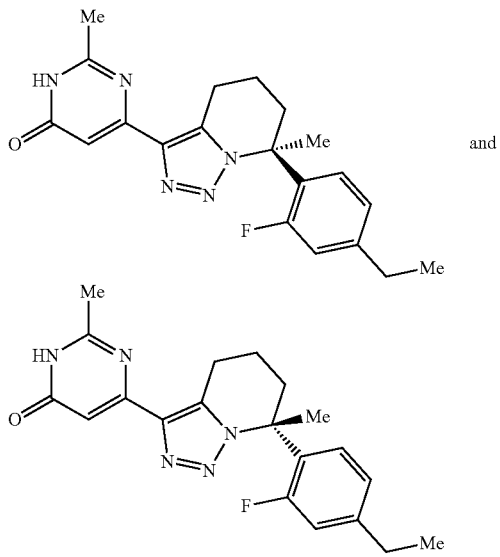

(R)- and (S)-6-(7-(4-Ethyl-2-fluorophenyl)-7-methyl-4,5,6,7-tetrahydro-[1,2,3]triazolo[1,5-a]pyridin-3-yl)-2-methylpyrimidin-4(3H)-one (Scheme 23)

Step 1. N-Methoxy-6-(6-((4-methoxybenzyl)oxy)-2-methylpyrimidin-4-yl)-N-methylhex-5-ynamide A solution of N-methoxy-N-methylhex-5-ynamide (0.704 g, 4.53 mmol), 4-chloro-6-((4-methoxybenzyl)oxy)-2-methylpyrimidine (1 g, 3.78 mmol) and triethylamine (1.147 g, 11.33 mmol) in tetrahydrofuran (4 ml) was degassed with nitrogen for 5 minutes. Then bis(triphenylphosphine)-palladium(II) chloride (0.530 g, 0.756 mmol) and copper(I) iodide (0.144 g, 0.756 mmol) were added and the reaction was heated to 65° C. overnight. The reaction was cooled to RT and concentrated. The residue was purified by silica gel column chromatography (0-50% ethyl acetate in petroleum ether) to afford the title compound as a liquid. LCMS=384.2 (M+1).

Step 2. 1-(4-Ethyl-2-fluorophenyl)-6-(6-((4-methoxybenzyl)oxy)-2-methylpyrimidin-4-yl)hex-5-yn-1-one A solution of 1-bromo-4-ethyl-2-fluorobenzene (318 mg, 1.565 mmol) in THF (5 ml) was purged with nitrogen 3 times and stirred under nitrogen atmosphere at 0° C. This was followed by the dropwise addition of isopropylmagnesium chloride-lithium chloride complex in THF (Sigma-Aldrich) (1.20 ml of 1.3 M solution) at 0° C. The reaction mixture was stirred under an atmosphere of nitrogen at 0° C. for 2 h. To the reaction mixture was added a solution of N-methoxy-6-(6-((4-methoxybenzyl)oxy)-2-methylpyrimidin-4-yl)-N-methylhex-5-ynamide (200 mg, 0.522 mmol) in THF (3.0 mL) at −78° C. The resulting mixture was stirred at RT for 16 h. The reaction mixture was quenched with saturated aqueous NH₄Cl (5.0 mL), diluted with brine (30 mL) and extracted with ethyl acetate (3×20 mL). The combined organic extracts were dried over anhydrous sodium sulfate and filtered. The filtrate was concentrated under vacuum and the residue was purified by silica gel chromatography (0-40% ethyl acetate in petroleum ether) to afford the title compound as a liquid. LCMS=447.1 (M+1).

Step 3. 2-(4-Ethyl-2-fluorophenyl)-7-(6-((4-methoxybenzyl)oxy)-2-methylpyrimidin-4-yl)hept-6-yn-2-ol Methylmagnesium bromide (0.672 ml, 0.672 mmol) was added to solution of 1-(4-ethyl-2-fluorophenyl)-6-(6-((4-methoxybenzyl)oxy)-2-methylpyrimidin-4-yl)hex-5-yn-1-one (200 mg, 0.448 mmol) in THF (5 ml) cooled to 0° C. The solution was stirred for 3 h at 0° C. The reaction mixture was then quenched with saturated aqueous NH₄Cl (5 mL) and extracted with ethyl acetate (3×20 mL). The combined organic extracts were washed with brine (10 mL), dried over anhydrous sodium sulfate and filtered. The filtrate was concentrated under vacuum and the residue was purified by silica gel chromatography (0-35% ethyl acetate in petroleum ether) to afford the title compound as an oil. LCMS=463.1 (M+1).

Step 4. 2-(4-Ethyl-2-fluorophenyl)-5-(4-(6-((4-methoxybenzyl)oxy)-2-methylpyrimidin-4-yl)-1H-1,2,3-triazol-5-yl)pentan-2-ol Azidotrimethylsilane (49.8 mg, 0.432 mmol) was added to a solution of 2-(4-ethyl-2-fluorophenyl)-7-(6-((4-methoxybenzyl)oxy)-2-methylpyrimidin-4-yl)hept-6-yn-2-ol (100 mg, 0.216 mmol) in DMA (2 ml) and the mixture was stirred for 16 h at 80° C. The mixture was extracted with ethyl acetate (3×20 mL) and the combined organic extracts were washed with brine (5 mL), dried over anhydrous sodium sulfate and filtered. The filtrate was concentrated under vacuum and the residue was purified by silica gel chromatography (0-80% ethyl acetate in petroleum ether) to afford the title compound as an oil. LCMS=506.0 (M+1).

Step 5. (R)- and (S)-6-(7-(4-Ethyl-2-fluorophenyl)-7-methyl-4,5,6,7-tetrahydro-[1,2,3]triazolo[1,5-a]pyridin-3-yl)-2-methylpyrimidin-4(3H)-one A solution of 2-(4-ethylphenyl)-5-(4-(6-((4-methoxybenzyl)oxy)-2-methylpyrimidin-4-yl)-1H-1,2,3-triazol-5-yl)pentan-2-ol (50 mg, 0.103 mmol) in trifluoroacetic acid (234 mg, 2.051 mmol) was stirred for 16 h at 80° C. The mixture was concentrated and then diluted with ethyl acetate. The organic layers was washed with brine (5 mL), dried over anhydrous sodium sulfate, and filtered. The filtrate was concentrated under vacuum to afford the racemic title compound as an oil. The racemic title compound was separated into its enantiomers via chiral chromatography (Chiralpak AS-H; 30% ethanol in hexane). The faster eluting enantiomer (Example 95) was obtained as a solid. ¹H NMR (400 MHz, CD₃OD) δ: 7.06-6.85 (m, 3H), 6.27-6.13 (m, 1H), 3.45-3.33 (m, 1H), 3.27-3.14 (m, 1H), 2.72-2.58 (m, 3H), 2.45 (s, 3H), 2.21-2.10 (m, 4H), 2.01-1.85 (m, 1H), 1.67-1.52 (m, 1H), 1.20 (t, J=7.6 Hz, 3H). LCMS=368.2 (M+1). The slower-eluting enantiomer (Example 96) was obtained as a solid. ¹H NMR (400 MHz, CD₃OD) δ: 7.06-6.85 (m, 3H), 6.27-6.13 (m, 1H), 3.45-3.33 (m, 1H), 3.27-3.14 (m, 1H), 2.72-2.58 (m, 3H), 2.45 (s, 3H), 2.21-2.10 (m, 4H), 2.01-1.85 (m, 1H), 1.67-1.52 (m, 1H), 1.21 (t, J=7.6 Hz, 3H). LCMS=368.2 (M+1).

TABLE 17

The following compounds were prepared using procedures similar to those described for examples 95 and 96 using the appropriate starting materials.

| Example No. | Structure | IUPAC name | Exact Mass [M + H]+ | Chiral Column |
|---|---|---|---|---|
| 97 | 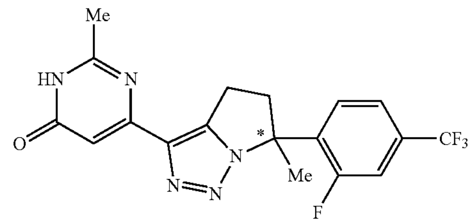 [SMILES: Cc1nc(-c2nnn3c2CCC3(C)c2ccc(C(F)(F)F)cc2F)cc(=O)[nH]1] | (R)- or (S)-6-(6-(2-Fluoro-4-(trifluoromethyl)phenyl)-6-methyl-5,6-dihydro-4H-pyrolo[1,2-c][1,2,3]triazol-3-yl)-2-methylpyrimidin-4(3H)-one | Calc'd 394.1, found 394.0 | Chiralpak IC |
| 98 | 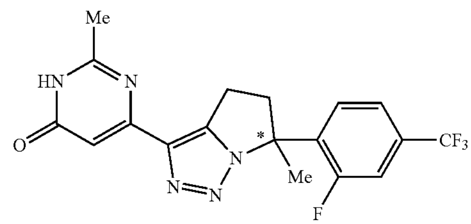 [SMILES: Cc1nc(-c2nnn3c2CCC3(C)c2ccc(C(F)(F)F)cc2F)cc(=O)[nH]1] | (S)- or (R)-6-(6-(2-Fluoro-4-(trifluoromethyl)phenyl)-6-methyl-5,6-dihydro-4H-pyrolo[1,2-c][1,2,3]triazol-3-yl)-2-methylpyrimidin-4(3H)-one | Calc'd 394.1, found 394.0 | Chiralpak IC |

Assay

The activity of the compounds in accordance with the present invention as PDE2 inhibitors may be readily determined using a fluorescence polarization (FP) methodology (Huang, W., et al., J. Biomol Screen, 2002, 7: 215). In particular, the compounds of the following examples had activity in reference assays by exhibiting the ability to inhibit the hydrolysis of the phosphate ester bond of a cyclic nucleotide. Any compound exhibiting a Ki (inhibitory constant) of about 10 μM or below would be considered a PDE2 inhibitor as defined herein.

In a typical experiment the PDE2 inhibitory activity of the compounds of the present invention was determined in accordance with the following experimental method. Rhesus PDE2A3 was amplified from rhesus macaque brain cDNA (Biochain Institute, Hayward, Calif.) using primers based on human PDE2A sequence (accession NM_002599.3) where the forward primer containing a Kozak consensus was 5'-gccaccatgggcaggcatgtggc-3' and the reverse primer was 5'-tcactcagcatcaaggctgca-3'. Amplification with Easy-A High-Fidelity PCR cloning enzyme (Stratagene, La Jolla, Calif.) was 95° C. for 2 minutes followed by thirty three cycles of 95° C. for 40 seconds, 52° C. for 30 seconds, and 72° C. for 2 minutes 48 seconds. Final extension was 72° C. for 7 minutes. The PCR product was TA cloned into pcDNA3.3-TOPO (Invitrogen, Carlsbad, Calif.) according to standard protocol. A consensus sequence was developed from multiple clones and then deposited into GenBank (EU812167). AD293 cells (Stratagene, La Jolla, Calif.) with 70-80% confluency were transiently transfected with rhesus PDE2A3/pcDNA3.3-TOPO using Lipofectamine 2000 according to manufacturer specifications (Invitrogen, Carlsbad, Calif.). Cells were harvested 48 hours post-transfection and lysed by sonication (setting 3, 10×5 sec pulses) in a buffer containing 20 mM HEPES pH 7.4, 1 mM EDTA and Complete Protease Inhibitor Cocktail Tablets (Roche, Indianapolis, Ind.). Lysate was collected by centrifugation at 75,000×g for 20 minutes at 4° C. and supernatant utilized for evaluation of PDE2 activity. The fluorescence polarization assay for cyclic nucleotide phosphodiesterases was performed using an IMAP® FP kit supplied by Molecular Devices, Sunnyvale, Calif. (product # R8139). IMAP® technology has been applied previously to examine the effects of phosphodiesterase inhibitors (Huang, W., et al., J. Biomol Screen, 2002, 7: 215). Assays were performed at room temperature in 384-well microtiter plates with an incubation volume of 20.2 μL. Solutions of test compounds were prepared in DMSO and serially diluted with DMSO to yield 8 μL of each of 10 solutions differing by 3-fold in concentration, at 32 serial dilutions per plate. 100% inhibition is determined using a known PDE2 inhibitor, which can be any compound that is present at 5,000 times its Ki value in the assay described below, such as Bay 60-7550 (Ki-~0.2 nM) at 1 μM concentration for 100% inhibition. Bay 60-7550 was obtained from Axxora via Fisher Scientific (cat# ALX-270-421-M025/cat# NC9314773). Put another way, any compound with Ki of ~0.2 to about 2 nM could be used at 1 to 10 μM. 0% of inhibition is determined by using DMSO (1% final concentrations).

A Labcyte Echo 555 (Labcyte, Sunnyvale, Calif.) is used to dispense 200 nL from each well of the titration plate to the 384 well assay plate. Ten microliters of a solution of enzyme (1/2000 final dilution from aliquots; sufficient to produce 20% substrate conversion) was added to the assay plate. Next 10 uL of a separate solution of the substrate FAM-labeled cAMP (50 nM final concentration product # R7506 from Molecular Devices) and the activator cGMP (1 uM final concentration), prepared in the assay buffer (10 mM Tris HCl, pH 7.2, 10 mM $MgCl_2$, 0.05% $NaN_3$ 0.01% Tween-20, and 1 mM DTT) was added to the assay plate and shaken to mix. The reaction is allowed to proceed at room temperature for 60 minutes. A binding solution is then made from the kit components, comprised of 80% Solution A, 20% Solution B and binding reagent at a volume of 1/600 the total binding solution. The enzymatic reaction is stopped by addition of 60 μL of the binding solution to each well of the assay plates and the plates are sealed and shaken for 30 seconds. The plate was incubated at room temperature for at least one hour prior to determining the fluorescence polarization (FP). The parallel and perpendicular fluorescence of each well of the plate was measured using a Tecan Genios Pro plate reader (Tecan, Switzerland) or Perkin Elmer EnVision™ plate reader (Waltham, Mass.). Fluorescence polarization (mP) was calculated from the parallel (S) and perpendicular (P) fluorescence of each sample well and the analogous values for the median control well, containing only substrate (So and Po), using the following equation:

Polarization $(mP)=1000*(S/So-P/Po)/(S/So+P/Po)$.

Dose-inhibition profiles for each compound were characterized by fitting the mP data to a four-parameter equation given below. The apparent inhibition constant ($K_I$), the maximum inhibition at the low plateau relative to "100% Inhibition Control" (Imax; e.g. 1=>same as this control), the minimum inhibition at the high plateau relative to the "0% Inhibition Control" (Imin, e.g. 0=>same as the no drug control) and the Hill slope (nH) are determined by a non-linear least squares fitting of the mP values as a function of dose of the compound using an in-house software based on the procedures described by Mosser et al., JALA, 2003, 8: 54-63, using the following equation:

$$mP = \frac{(0\%\ mP - 100\%\ mP)(I\max - I\min)}{1 + \left[\frac{[Drug]}{\left(10^{-pK_I}\left(1 + \frac{[Substrate]}{K_M}\right)\right)}\right]^{nH}} +$$

$$100\%\ mP + (0\%\ mP - 100\%\ mP)(1 - I\max)$$

The median signal of the "0% inhibition controls" (0% mP) and the median signal of the "100% inhibition controls" (100% mP) are constants determined from the controls located in columns 1-2 and 23-24 of each assay plate. An apparent ($K_M$) for FAM-labeled cAMP of ~10 uM was used.

Selectivity for PDE2, as compared to other PDE families, was assessed using the IMAP® technology. Human PDE10A2 enzyme was prepared from cytosolic fractions of transiently transfected HEK cells. All other PDE's were GST Tag human enzyme expressed in insect cells and were obtained from BPS Bioscience (San Diego, Calif.): PDE1A (Cat#60010), human PDE2A1 (Cat#60020), PDE3A (Cat#60030), PDE4A1A (Cat#60040), PDE5A1 (Cat#60050), PDE6C (Cat#60060), PDE7A (Cat#60070), PDE8A1 (Cat#60080), PDE9A2 (Cat#60090), PDE11A4 (Cat#60110).

Assays for PDE 1 through 11 were performed in parallel at room temperature in 384-well microtiter plates with an incubation volume of 20.2 µL. Solutions of test compounds were prepared in DMSO and serially diluted with DMSO to yield 30 µL of each of ten solutions differing by 3-fold in concentration, at 32 serial dilutions per plate. 100% inhibition was determined by adding buffer in place of the enzyme and 0% inhibition is determined by using DMSO (1% final concentrations). A Labcyte POD 810 (Labcyte, Sunnyvale, Calif.) was used to dispense 200 nL from each well of the titration plate to make eleven copies of the assay plate for each titration, one copy for each PDE enzyme. A solution of each enzyme (dilution from aliquots, sufficient to produce 20% substrate conversion) and a separate solution of FAM-labeled cAMP or FAM-labeled cGMP from Molecular Devices (Sunnyvale, Calif., product # R7506 or cGMP#R7508), at a final concentration of 50 nM were made in the assay buffer (10 mM Tris HCl, pH 7.2, 10 mM $MgCl_2$, 0.05% $NaN_3$ 0.01% Tween-20, and 1 mM DTT). Note that the substrate for PDE2 is 50 nM FAM cAMP containing 1000 nM of cGMP. The enzyme and the substrate were then added to the assay plates in two consecutive additions of 10 µL and then shaken to mix. The reaction was allowed to proceed at room temperature for 60 minutes. A binding solution was then made from the kit components, comprised of 80% Solution A, 20% Solution B and binding reagent at a volume of 1/600 the total binding solution. The enzymatic reaction was stopped by addition of 60 µL of the binding solution to each well of the assay plate. The plates were sealed and shaken for 10 seconds. The plates were incubated at room temperature for one hour, then the parallel and perpendicular fluorescence was measured using a Tecan Genios Pro plate reader (Tecan, Switzerland). The apparent inhibition constants for the compounds against all 11 PDE's was determined from the parallel and perpendicular fluorescent readings as described for PDE10 FP assay using the following apparent $K_M$ values for each enzyme and substrate combination: PDE1A (FAM cGMP) 70 nM, human PDE2A1 (FAM cAMP) 10,000 nM, PDE3A (FAM cAMP) 50 nM, PDE4A1A (FAM cAMP) 1500 nM, PDE5A1 (FAM cGMP) 400 nM, PDE6C (FAM cGMP) 700 nM, PDE7A (FAM cAMP) 150 nM, PDE8A1 (FAM cAMP) 50 nM, PDE9A2 (FAM cGMP) 60 nM, PDE10A2 (FAM cAMP) 150 nM, PDE11A4 (FAM cAMP) 1000 nM. The intrinsic PDE2 inhibitory activity of a compound which may be used in accordance with the present invention may be determined by these assays.

The compounds of the following examples had activity in inhibiting the human PDE2 enzyme in the aforementioned assays with a Ki of less than about 50 µM. Many of compounds within the present invention had activity in inhibiting the human PDE2 enzyme in the aforementioned assays, with a Ki of less than about 1 µM, preferably less than or about 0.1 µM. Additional data is provided in the following Examples. Such a result is indicative of the intrinsic activity of the compounds in use as inhibitors of the PDE2 enzyme. In general, one of ordinary skill in the art would appreciate that a substance is considered to effectively inhibit PDE2 activity if it has a Ki of less than or about 1 µM, preferably less than or about 0.1 µM. The present invention also includes compounds within the generic scope of the invention which possess activity as inhibitors of other phosphodiesterase enzymes.

In the following tables representative data for the compounds of formula I as PDE2 inhibitors as determined by the foregoing assays. The PDE2 Ki is a measure of the ability of the test compound to inhibit the action of the PDE2 enzyme.

TABLE 18

PDE2 Ki Values (NA = Not available).

| Example No. | Human PDE2A1 Ki (nM) or % Inhibition at 3.0 µM, | Rhesus PDE2 Ki (nM) |
|---|---|---|
| 1 | 36.3 | NA |
| 2 | ~1300 | NA |
| 3 | 112 | NA |
| 4 | 1027 | NA |
| 5 | 52.2 | NA |
| 6 | ~1900 | NA |
| 7 | 60.9 | NA |
| 8 | ~1548 | NA |
| 9 | 6.9 | 9.4 |
| 10 | 132 | NA |
| 11 | 55.8 | 50.4 |
| 12 | 8.4 | 8.9 |
| 13 | 76.8 | 98.9 |
| 14 | 20.9 | 24.9 |
| 15 | 4.7 | 6.5 |
| 16 | 37.8 | 39.4 |

TABLE 18-continued

PDE2 Ki Values (NA = Not available).

| Example No. | Human PDE2A1 Ki (nM) or % Inhibition at 3.0 μM, | Rhesus PDE2 Ki (nM) |
|---|---|---|
| 17 | 36.2 | 44.7 |
| 18 | 47.0 | 54.8 |
| 19 | 2.1 | 3.4 |
| 20 | 46.7 | NA |
| 21 | 2.6 | 3.9 |
| 22 | 17.7 | NA |
| 23 | 203 | NA |
| 24 | 38.8 | NA |
| 25 | 58.4 | NA |
| 26 | 3.2 | NA |
| 27 | 46.6 | NA |
| 28 | 7.0 | 9.0 |
| 29 | 0.53 | 0.63 |
| 30 | 1.7 | NA |
| 31 | 5.4 | NA |
| 32 | 1.6 | 2.1 |
| 33 | 99.6 | NA |
| 34 | 4.9 | NA |
| 35 | 41.5 | NA |
| 36 | 1.7 | NA |
| 37 | 11.0 | NA |
| 38 | 10.5 | NA |
| 39 | 7.2 | NA |
| 40 | 22.6 | NA |
| 41 | 38.0 | NA |
| 42 | 9.7 | NA |
| 43 | 4.6 | NA |
| 44 | 44% | NA |
| 45 | 9.2 | NA |
| 46 | 1100 | NA |
| 47 | 48% | NA |
| 48 | 42.4 | NA |
| 49 | 33% | NA |
| 50 | 20.7 | NA |
| 51 | 79.9 | NA |
| 52 | 139 | NA |
| 53 | 73.2 | NA |
| 54 | 16.2 | NA |
| 55 | 232 | NA |
| 56 | 616 | NA |
| 57 | 29.0 | NA |
| 58 | 1.3 | NA |
| 59 | 178 | NA |
| 60 | NA | 204 |
| 61 | 52.7 | NA |
| 62 | 387 | NA |
| 63 | 16% | NA |
| 64 | 23.3 | NA |
| 65 | 15.9 | NA |
| 66 | 525 | NA |
| 67 | 17% | NA |
| 68 | 7.7 | NA |
| 69 | 1,132 | NA |
| 70 | 54.3 | NA |
| 71 | 27% | NA |
| 72 | 864 | NA |
| 73 | 26.9 | NA |
| 74 | 0.42 | NA |
| 75 | 8.9 | NA |
| 76 | 181.7 | NA |
| 77 | 2,802 | NA |
| 78 | 803.8 | NA |
| 79 | 8.3 | NA |
| 80 | 2,059 | NA |
| 81 | 0.93 | 1.7 |
| 82 | 221.0 | NA |
| 83 | 4.2 | NA |
| 84 | 224.0 | NA |
| 85 | 1,203 | NA |
| 86 | 167.0 | NA |
| 87 | 1.2 | 1.8 |
| 88 | >2,955 | NA |
| 89 | 0.40 | 0.63 |
| 90 | 1,897 | NA |
| 91 | 0.56 | NA |
| 92 | 728.1 | NA |
| 93 | 67.0 | NA |
| 94 | 56.3 | NA |
| 95 | 1.8 | NA |
| 96 | 430 | NA |
| 97 | 1.5 | 1.3 |
| 98 | 217.7 | NA |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound represented by structural formula I:

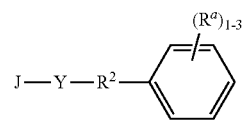

I or a pharmaceutically acceptable salt or solvate thereof, wherein:

J represents pyrimidinone optionally substituted with 1 to 2 groups selected from $C_{1-6}$alkyl, $C_{2-6}$alkenyl, $(CH_2)_n$ $C_{3-10}$cycloalkyl, and $(CH_2)_nC_{6-10}$aryl, said alkyl and aryl optionally substituted with one to three groups of $R^a$;

Y is triazolyl optionally substituted with $R^b$;

$R^2$ is selected from the group consisting of $CR^xR^y$;

or $R^2$ and the available carbon atom and/or nitrogen atom of the Y triazolyl can combine to form an 8 to 10 membered heterocyclyl optionally interrupted with one or more heteroatoms selected from O, S, and N, and said heterocyclyl optionally substituted with 1 to 3 groups of $R^b$;

$R^x$ and $R^y$ are independently selected from the group consisting of H, $(CH_2)_nOR$, $C_{1-6}$alkyl, $C_{3-6}$ cycloalkyl, C(O)OR and $N(R)_2$, said alkyl optionally substituted with one to three groups of $R^a$;

R represents H, or $C_{1-6}$ alkyl, $R^x$ and $R^y$ can combine with the carbon atom to which they are attached to form a group selected from C=O, $C_{3-6}$ cycloalkyl and $C_{3-6}$ heterocyclyl;

$R^a$ is selected from the group consisting of halo, CN, $C_{1-6}$alkyl, $(CH_2)_nOR$, $(O)_pC_{1-4}$haloalkyl, C(O)OR, —O(CH_2)_nN(R)_2, $(CHR)_nN(R)_2$, $NO_2$, $SCF_3$, $S(O)_s$ $CF_3$, $S(O)_sR$, $SF_5$, $C_{3-10}$cycloalkyl, O—$C_{3-10}$ cycloalkyl, $C_{5-10}$heterocyclyl, and $C_{6-10}$aryl, said alkyl, cycloalkyl, heterocyclyl and aryl optionally substituted with one to three groups of $R^b$, $R^b$, is selected from the group consisting of H, halo, $C_{1-6}$alkyl, $(CH_2)_nOR$, and $(O)_pC_{1-4}$haloalkyl;

n represents 0, 1, 2, 3, or 4;

s represents 0, 1, or 2; and p represents 0 or 1.

2. The compound according to claim 1 wherein the pyrimidinone is represented by structural formula I'

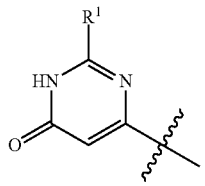

wherein R¹ is selected from the group consisting of H, $C_{1-6}$alkyl, $C_{2-6}$alkenyl, $(CH_2)_nC_{3-10}$cycloalkyl, and $(CH_2)_nC_{6-10}$aryl, said alkyl and aryl optionally substituted with one to three groups of $R^a$.

3. The compound according to claim 2 wherein R¹ is selected from the group consisting of hydrogen, methyl, ethyl, isopropyl, propyl, butyl, isobutyl, pentyl, ethenyl, butenyl, and propenyl.

4. The compound according to claim 2 wherein R¹ is $(CH_2)_nC_{3-10}$cycloalkyl selected from the group consisting of cyclopropyl, cyclobutyl, cyclopentyl, and cyclohexyl.

5. The compound according to claim 2 wherein R¹ is $(CH_2)_nC_{6-10}$ aryl wherein the aryl is optionally substituted phenyl.

6. The compound according to claim 1 wherein R² is selected from the group consisting of $CH(CH_2)_nCH_3$, $C(CH_3)_2$, $CH(CH(CH_3)_2)$, $CH_2$, —C(=O)—, CH $(CH_2)_n$ OH, $C(CH_3)(OH)$, $CHC(O)OCH_3$, $CH(NHCH_3)$, $CH(CH_2)$ $n(OCH_3)$, CH-cyclopropyl, and cyclobutyl.

7. The compound according to claim 6 wherein R² is $CH(CH_2)_nCH_3$.

8. The compound according to claim 1 wherein R² and an available carbon atom and/or nitrogen atoms of the Y triazolyl combine to form a $C_{8-10}$ heterocyclyl selected from the group consisting of tetrahydrotriazolopyridinyl, dihydrotriazolooxazinyl, dihydropyrrolotriazolyl and tetrahydrotriazoloazepinyl.

9. The compound according to claim 1 represented by structural formula Ia:

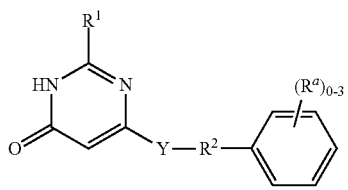

or a pharmaceutically acceptable salt or solvate thereof.

10. The compound according to claim 9 wherein Y—R² is selected from the group consisting of (a)
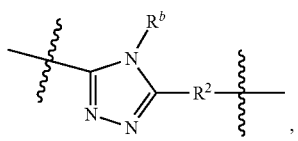

(b)
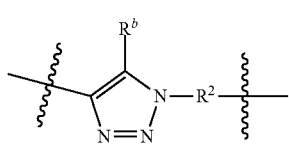

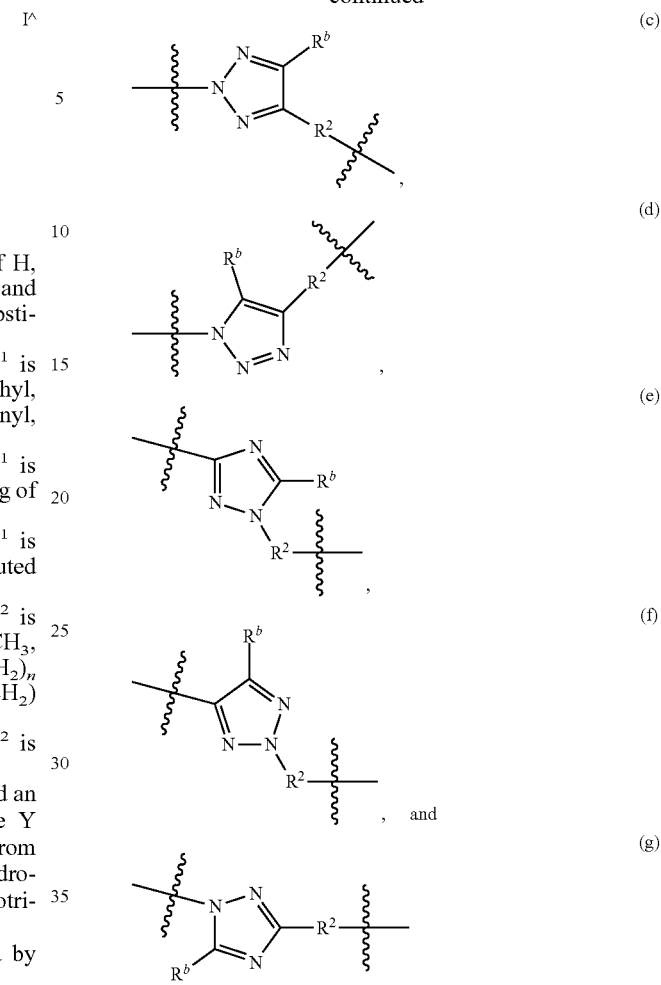

$R^b$ is hydrogen, R¹ is selected from the group consisting of optionally substituted $C_{1-6}$alkyl cyclopropyl, cyclobutyl, and $(CH_2)_n$phenyl and R² is selected from the group consisting of $CH(CH_2)_nCH_3$, $CHCH(CH_3)_2$, $CH_2$, $CH(CH_2)_nOH$.

11. The compound according to claim 10 wherein Y is (a), $R^b$ is H or $CH_3$, and R¹ is optionally substituted methyl, and R² is $CH(CH_2)_nCH_3$.

12. The compound according to claim 10 wherein Y is (b), $R^b$ is H or $CH_3$, and R¹ is optionally substituted methyl, and R² is $CH(CH_2)_nCH_3$.

13. The compound according to claim 10 wherein Y is (d), $R^b$ is H or $CH_3$, and R¹ is optionally substituted methyl, and R² is $CH(CH_2)_nCH_3$.

14. The compound according to claim 10 wherein Y is (f), $R^b$ is H or $CH_3$, and R¹ is optionally substituted methyl, and R² is $CH(CH_2)_nCH_3$.

15. The compound according to claim 10 wherein the Y triazole is (a), (b), (c), (d), or (e) R¹ is optionally substituted methyl, and R² and $R^b$ combine to form an optionally substituted ring fused to the triazole.

16. The compound according to claim 15 wherein the fused triazole ring is selected from the group consisting of optionally substituted tetrahydrotriazolopyridinyl, dihydrotriazolooxazinyl, dihydropyrrolotriazolyl, and tetrahydrotriazoloazepinyl.

17. A compound which is:
(R)-6-(2-(1-(2-Chloro-4-(trifluoromethyl)phenyl)ethyl)-2H-1,2,3-triazol-4-yl)-2-methylpyrimidin-4(3H)-one,
(S)-6-(2-(1-(2-Chloro-4-(trifluoromethyl)phenyl)ethyl)-2H-1,2,3-triazol-4-yl)-2-methylpyrimidin-4(3H)-one,
(S)-6-(1-(1-(2-Chloro-4-(trifluoromethyl)phenyl)ethyl)-1H-1,2,3-triazol-4-yl)-2-methylpyrimidin-4(3H)-one,
(R)-6-(1-(1-(2-Chloro-4-(trifluoromethyl)phenyl)ethyl)-1H-1,2,3-triazol-4-yl)-2-methylpyrimidin-4(3H)-one,
(R)-6-(2-(1-(2-fluoro-4-(trifluoromethyl)phenyl)ethyl)-2H-1,2,3-triazol-4-yl)-2-methylpyrimidin-4(3H)-one,
(S)-6-(2-(1-(2-fluoro-4-(trifluoromethyl)phenyl)ethyl)-2H-1,2,3-triazol-4-yl)-2-methylpyrimidin-4(3H)-one,
(R)-2-methyl-6-(2-(1-(2-methyl-4-(trifluoromethyl)phenyl)ethyl)-2H-1,2,3-triazol-4-yl)pyrimidin-4(3H)-one,
(S)-2-methyl-6-(2-(1-(2-methyl-4-(trifluoromethyl)phenyl)ethyl)-2H-1,2,3-triazol-4-yl)pyrimidin-4(3H)-one,
(R)-6-(2-(1-(2-chloro-4-ethylphenyl)ethyl)-2H-1,2,3-triazol-4-yl)-2-methylpyrimidin-4(3H)-one,
(S)-6-(2-(1-(2-chloro-4-ethylphenyl)ethyl)-2H-1,2,3-triazol-4-yl)-2-methylpyrimidin-4(3H)-one,
(R)-2-methyl-6-(1-(1-(2-methyl-4-(trifluoromethyl)phenyl)-ethyl)-1H-1,2,3-triazol-4-yl)pyrimidin-4(3H)-one,
(S)-2-methyl-6-(1-(1-(2-methyl-4-(trifluoromethyl)phenyl)-ethyl)-1H-1,2,3-triazol-4-yl)pyrimidin-4(3H)-one,
2-methyl-6-(1-(1-(4-(trifluoromethoxy)phenyl)ethyl)-1H-1,2,3-triazol-4-yl)pyrimidin-4(3H)-one,
2-benzyl-6-(1-(1-(2-fluoro-4-(trifluoromethyl)phenyl)ethyl)-1H-1,2,3-triazol-4-yl)pyrimidin-4(3H)-one,
6-(1-(1-(2-fluoro-4-(trifluoromethoxy)phenyl)ethyl)-1H-1,2,3-triazol-4-yl)-2-methylpyrimidin-4(3H)-one,
2-(cyclopropylmethyl)-6-(1-(1-(2-fluoro-4-(trifluoromethyl)phenyl)ethyl)-1H-1,2,3-triazol-4-yl)pyrimidin-4(3H)-one,
(E)-2-(but-1-enyl)-6-(1-(1-(2-fluoro-4-(trifluoromethyl)phenyl)ethyl)-1H-1,2,3-triazol-4-yl)pyrimidin-4(3H)-one,
2-methyl-6-(1-(1-(4-(pentafluorosulfanyl)phenyl)ethyl)-1H-1,2,3-triazol-4-yl)pyrimidin-4(3H)-one,
(R)-2-methyl-6-(1-(1-(4-(trifluoromethyl)phenyl)ethyl)-1H-1,2,3-triazol-4-yl)pyrimidin-4(3H)-one,
(S)-2-methyl-6-(1-(1-(4-(trifluoromethyl)phenyl)ethyl)-1H-1,2,3-triazol-4-yl)pyrimidin-4(3H)-one,
(R)-6-(1-(1-(2-chloro-4-ethylphenyl)ethyl)-1H-1,2,3-triazol-4-yl)-2-methylpyrimidin-4(3H)-one,
(S)-6-(1-(1-(2-chloro-4-ethylphenyl)ethyl)-1H-1,2,3-triazol-4-yl)-2-methylpyrimidin-4(3H)-one,
(R)-6-(1-(1-(2,3-difluoro-4-(trifluoromethyl)phenyl)ethyl)-1H-1,2,3-triazol-4-yl)-2-methylpyrimidin-4(3H)-one,
(S)-6-(1-(1-(2,3-difluoro-4-(trifluoromethyl)phenyl)ethyl)-1H-1,2,3-triazol-4-yl)-2-methylpyrimidin-4(3H)-one,
(R)-6-(1-(1-(2,5-difluoro-4-(trifluoromethyl)phenyl)ethyl)-1H-1,2,3-triazol-4-yl)-2-methylpyrimidin-4(3H)-one,
(S)-6-(1-(1-(2,5-difluoro-4-(trifluoromethyl)phenyl)ethyl)-1H-1,2,3-triazol-4-yl)-2-methylpyrimidin-4(3H)-one,
(R)-6-(1-(1-(2-chloro-4-cyclopropylphenyl)ethyl)-1H-1,2,3-triazol-4-yl)-2-methylpyrimidin-4(3H)-one,
(S)-6-(1-(1-(2-chloro-4-cyclopropylphenyl)ethyl)-1H-1,2,3-triazol-4-yl)-2-methylpyrimidin-4(3H)-one,
(S)-6-(1-(1-(2-fluoro-4-(trifluoromethyl)phenyl)ethyl)-1H-1,2,3-triazol-4-yl)-2-methylpyrimidin-4(3H)-one,
(R)-6-(1-(1-(2-fluoro-4-(trifluoromethyl)phenyl)ethyl)-1H-1,2,3-triazol-4-yl)-2-methylpyrimidin-4(3H)-one,
6-(1-(1-(2-Chloro-4-(trifluoromethyl)phenyl)cyclobutyl)-1H-1,2,3-triazol-4-yl)-2-methylpyrimidin-4(3H)-one,
6-(1-(2-(2-chloro-4-(trifluoromethyl)phenyl)propan-2-yl)-1H-1,2,3-triazol-4-yl)-2-methylpyrimidin-4(3H)-one,
2-methyl-6-(1-(2-(2-methyl-4-(trifluoromethyl)phenyl)propan-2-yl)-1H-1,2,3-triazol-4-yl)pyrimidin-4(3H)-one,
6-(1-(2-(2-chloro-4-ethylphenyl)propan-2-yl)-1H-1,2,3-triazol-4-yl)-2-methylpyrimidin-4(3H)-one,
6-(1-(2-(4-ethyl-2-methylphenyl)propan-2-yl)-1H-1,2,3-triazol-4-yl)-2-methylpyrimidin-4(3H)-one,
6-(1-(2-(2-chloro-4-cyclopropylphenyl)propan-2-yl)-1H-1,2,3-triazol-4-yl)-2-methylpyrimidin-4(3H)-one,
(R)-6-(1-(1-(2-fluoro-4-(trifluoromethyl)phenyl)propyl)-1H-1,2,3-triazol-4-yl)-2-methylpyrimidin-4(3H)-one
(S)-6-(1-(1-(2-fluoro-4-(trifluoromethyl)phenyl)propyl)-1H-1,2,3-triazol-4-yl)-2-methylpyrimidin-4(3H)-one,
(R)-6-(1-(1-(2-fluoro-4-(trifluoromethyl)phenyl)-2-methylpropyl)-1H-1,2,3-triazol-4-yl)-2-methylpyrimidin-4(3H)-one,
(S)-6-(1-(1-(2-fluoro-4-(trifluoromethyl)phenyl)-2-methylpropyl)-1H-1,2,3-triazol-4-yl)-2-methylpyrimidin-4(3H)-one,
(R)-6-(1-(cyclopropyl(2-fluoro-4-(trifluoromethyl)phenyl)methyl)-1H-1,2,3-triazol-4-yl)-2-methylpyrimidin-4(3H)-one,
(S)-6-(1-(cyclopropyl(2-fluoro-4-(trifluoromethyl)phenyl)methyl)-1H-1,2,3-triazol-4-yl)-2-methylpyrimidin-4(3H)-one,
(R)-6-(1-(1-(2-chloro-4-(trifluoromethyl)phenyl)-ethyl)-5-methyl-1H-1,2,3-triazol-4-yl)-2-methylpyrimidin-4(3H)-one,
(S)-6-(1-(1-(2-chloro-4-(trifluoromethyl)phenyl)-ethyl)-5-methyl-1H-1,2,3-triazol-4-yl)-2-methylpyrimidin-4(3H)-one,
(R)-6-(5-butyl-1-(1-(2-chloro-4-(trifluoromethyl)phenyl)ethyl)-1H-1,2,3-triazol-4-yl)-2-methylpyrimidin-4(3H)-one,
(S)-6-(5-butyl-1-(1-(2-chloro-4-(trifluoromethyl)phenyl)ethyl)-1H-1,2,3-triazol-4-yl)-2-methylpyrimidin-4(3H)-one,
(R)-2-methyl-6-(7-(4-(trifluoromethyl)phenyl)-4,5,6,7-tetrahydro-[1,2,3]triazolo[1,5-a]pyridin-3-yl)pyrimidin-4(3H)-one,
(S)-2-methyl-6-(7-(4-(trifluoromethyl)phenyl)-4,5,6,7-tetrahydro-[1,2,3]triazolo[1,5-a]pyridin-3-yl)pyrimidin-4(3H)-one,
(R)-6-(7-(2-fluoro-4-(trifluoromethyl)phenyl)-4,5,6,7-tetrahydro-[1,2,3]triazolo[1,5-a]pyridin-3-yl)-2-methylpyrimidin-4(3H)-one,
(S)-6-(7-(2-fluoro-4-(trifluoromethyl)phenyl)-4,5,6,7-tetrahydro-[1,2,3]triazolo[1,5-a]pyridin-3-yl)-2-methylpyrimidin-4(3H)-one,
(R)-2-methyl-6-(8-(4-(trifluoromethyl)phenyl)-5,6,7,8-tetrahydro-4H-[1,2,3]triazolo[1,5-a]azepin-3-yl)pyrimidin-4(3H)-one,
(S)-2-methyl-6-(8-(4-(trifluoromethyl)phenyl)-5,6,7,8-tetrahydro-4H-[1,2,3]triazolo[1,5-a]azepin-3-yl)pyrimidin-4(3H)-one,
2-methyl-6-(7-(4-(trifluoromethyl)phenyl)-6,7-dihydro-4H-[1,2,3]triazolo[5,1-c][1,4]oxazin-3-yl)pyrimidin-4(3H)-one, (R)-2-methyl-6-(7-methyl-7-(4-(trifluoromethyl)phenyl)-4,5,6,7-tetrahydro-[1,2,3]triazolo[1,5-a]pyridin-3-yl)pyrimidin-4(3H)-one, (S)-2-methyl-6-(7-methyl-7-(4-(trifluoromethyl)phenyl)-4,5,6,7-tetrahydro-[1,2,3]triazolo[1,5-a]pyridin-3-yl)pyrimidin-4(3H)-one, (R)-6-(7-ethyl-7-(4-(trifluoromethyl)phenyl)-4,5,6,7-tetrahydro-[1,2,3]triazolo[1,5-a]pyridin-3-yl)-2-methylpyrimidin-4(3H)-one, (S)-6-(7-ethyl-7-(4-(trifluoromethyl)phenyl)-4,5,6,7-tetrahydro-[1,2,3]triazolo[1,5-a]pyridin-3-yl)-2-methylpyrimidin-4(3H)-one, (R)-6-(7-(2-fluoro-4-(trifluoromethyl)phenyl)-7-methyl-4,5,6,7-tetrahydro-[1,2,3]triazolo[1,5-a]pyridin-3-yl)-2-methylpyrimidin-4(3H)-one, (S)-6-(7-(2-fluoro-4-(trifluoromethyl)phenyl)-7-methyl-4,5,6,7-tetrahydro-[1,2,3]triazolo[1,5-a]pyridin-3-yl)-2-methylpyrimidin-4(3H)-one, 2-Methyl-6-(5-(1-(4-(trifluoromethyl)phenyl)ethyl)-4H-1,2,4-triazol-3-yl)pyrimidin-4(3H)-one, (S)-6-(5-(1-(2-fluoro-4-(trifluoromethyl)-phenyl)ethyl)-4H-1,2,4-triazol-3-yl)-2-methylpyrimidin-4(3H)-one, (R)-6-(5-(1-(2-fluoro-4-(trifluoromethyl)-phenyl)ethyl)-4H-1,2,4-triazol-3-yl)-2-methylpyrimidin-4(3H)-one, (S)-6-(5-(1-(2-fluoro-4-(trifluoromethyl)-phenyl)ethyl)-4-methyl-4H-1,2,4-triazol-3-yl)-2-methylpyrimidin-4(3H)-one, (R)-6-(5-(1-(2-fluoro-4-(trifluoromethyl)-phenyl)ethyl)-4-methyl-4H-1,2,4-triazol-3-yl)-2-methylpyrimidin-4(3H)-one, (S)-6-(5-(1-(2-chloro-4-(trifluoromethyl)-phenyl)ethyl)-4H-1,2,4-triazol-3-yl)-2-methylpyrimidin-4(3H)-one, (R)-6-(5-(1-(2-chloro-4-(trifluoromethyl)-phenyl)ethyl)-4H-1,2,4-triazol-3-yl)-2-methylpyrimidin-4(3H)-one, (S)-6-(5-(1-(2-chloro-4-(trifluoromethyl)-phenyl)ethyl)-4-methyl-4H-1,2,4-triazol-3-yl)-2-methylpyrimidin-4(3H)-one, (R)-6-(5-(1-(2-chloro-4-(trifluoromethyl)-phenyl)ethyl)-4-methyl-4H-1,2,4-triazol-3-yl)-2-methylpyrimidin-4(3H)-one, 6-(5-(2-(2-fluoro-4-(trifluoromethyl)phenyl)propan-2-yl)-4-methyl-4H-1,2,4-triazol-3-yl)-2-methylpyrimidin-4(3H)-one, (R)-2-methyl-6-(8-(4-(trifluoromethyl)phenyl)-5,6,7,8-tetrahydro-[1,2,4]triazolo[4,3-a]pyridin-3-yl)pyrimidin-4(3H)-one, (S)-2-methyl-6-(8-(4-(trifluoromethyl)phenyl)-5,6,7,8-tetrahydro-[1,2,4]triazolo[4,3-a]pyridin-3-yl)pyrimidin-4(3H)-one, (S)-2-methyl-6-(8-methyl-8-(4-(trifluoromethyl)phenyl)-5,6,7,8-tetrahydro-[1,2,4]triazolo[4,3-a]pyridin-3-yl)pyrimidin-4(3H)-one, (R)-2-methyl-6-(8-methyl-8-(4-(trifluoromethyl)phenyl)-5,6,7,8-tetrahydro-[1,2,4]triazolo[4,3-a]pyridin-3-yl)pyrimidin-4(3H)-one, (R)-6-(4-(1-(2-chloro-4-(trifluoromethyl)phenyl)ethyl)-1H-1,2,3-triazol-1-yl)-2-methylpyrimidin-4(3H)-one, (S)-6-(4-(1-(2-chloro-4-(trifluoromethyl)phenyl)ethyl)-1H-1,2,3-triazol-1-yl)-2-methylpyrimidin-4(3H)-one, (R)-2-Methyl-6-(7-methyl-7-(4-(trifluoromethoxy)phenyl)-4,5,6,7-tetrahydro-[1,2,3]triazolo[1,5-a]pyridin-3-yl)pyrimidin-4(3H)-one, (S)-2-Methyl-6-(7-methyl-7-(4-(trifluoromethoxy)phenyl)-4,5,6,7-tetrahydro-[1,2,3]triazolo[1,5-a]pyridin-3-yl)pyrimidin-4(3H)-one, (R)-2-Methyl-6-(7-methyl-7-(2-methyl-4-(trifluoromethyl)phenyl)-4,5,6,7-tetrahydro-[1,2,3]triazolo[1,5-a]pyridin-3-yl)pyrimidin-4(3H)-one, (S)-2-Methyl-6-(7-methyl-7-(2-methyl-4-(trifluoromethyl)phenyl)-4,5,6,7-tetrahydro-[1,2,3]triazolo[1,5-a]pyridin-3-yl)pyrimidin-4(3H)-one, (R)-6-(8-(2-Fluoro-4-(trifluoromethyl)phenyl)-8-methyl-5,6,7,8-tetrahydro-[1,2,4]triazolo[4,3-a]pyridin-3-yl)-2-methylpyrimidin-4(3H)-one, (S)-6-(8-(2-Fluoro-4-(trifluoromethyl)phenyl)-8-methyl-5,6,7,8-tetrahydro-[1,2,4]triazolo[4,3-a]pyridin-3-yl)-2-methylpyrimidin-4(3H)-one, (R)-6-(4-(1-(2-Chloro-4-(trifluoromethyl)phenyl)ethyl)-2H-1,2,3-triazol-2-yl)-2-methylpyrimidin-4(3H)-one, (S)-6-(4-(1-(2-Chloro-4-(trifluoromethyl)phenyl)ethyl)-2H-1,2,3-triazol-2-yl)-2-methylpyrimidin-4(3H)-one, (R)-6-(3-(1-(2-Fluoro-4-(trifluoromethyl)phenyl)ethyl)-1H-1,2,4-triazol-1-yl)-2-methylpyrimidin-4(3H)-one, (S)-6-(3-(1-(2-Fluoro-4-(trifluoromethyl)phenyl)ethyl)-1H-1,2,4-triazol-1-yl)-2-methylpyrimidin-4(3H)-one, 6-(1-(1-(2-Fluoro-4-(trifluoromethyl)phenyl)ethyl)-1H-1,2,4-triazol-3-yl)-2-methylpyrimidin-4(3H)-one, (R)-6-(7-(2-Chloro-4-(trifluoromethyl)phenyl)-7-methyl-4,5,6,7-tetrahydro-[1,2,3]triazolo[1,5-a]pyridin-3-yl)-2-methylpyrimidin-4(3H)-one, (S)-6-(7-(2-Chloro-4-(trifluoromethyl)phenyl)-7-methyl-4,5,6,7-tetrahydro-[1,2,3]triazolo[1,5-a]pyridin-3-yl)-2-methylpyrimidin-4(3H)-one, (R)-6-(7-(2-Fluoro-4-(trifluoromethyl)phenyl)-7-methyl-4,5,6,7-tetrahydro-[1,2,3]triazolo[1,5-a]pyridin-3-yl)-2-(4-methoxybenzyl)pyrimidin-4(3H)-one, (S)-6-(7-(2-Fluoro-4-(trifluoromethyl)phenyl)-7-methyl-4,5,6,7-tetrahydro-[1,2,3]triazolo[1,5-a]pyridin-3-yl)-2-(4-methoxybenzyl)pyrimidin-4(3H)-one, (R)-6-(7-(2-Fluoro-4-(trifluoromethyl)phenyl)-7-methyl-4,5,6,7-tetrahydro-[1,2,3]triazolo[1,5-a]pyridin-3-yl)-2-(3-methoxy-benzyl)pyrimidin-4(3H)-one, (S)-6-(7-(2-Fluoro-4-(trifluoromethyl)phenyl)-7-methyl-4,5,6,7-tetrahydro-[1,2,3]triazolo[1,5-a]pyridin-3-yl)-2-(3-methoxy-benzyl)pyrimidin-4(3H)-one, (R)-6-(8-(2-Fluoro-4-(trifluoromethyl)phenyl)-8-methyl-5,6,7,8-tetrahydro-4H-[1,2,3]triazolo[1,5-a]azepin-3-yl)-2-methylpyrimidin-4(3H)-one, (S)-6-(8-(2-Fluoro-4-(trifluoromethyl)phenyl)-8-methyl-5,6,7,8-tetrahydro-4H-[1,2,3]triazolo[1,5-a]azepin-3-yl)-2-methylpyrimidin-4(3H)-one, (R)-6-(7-(4-Ethyl-2-fluorophenyl)-7-methyl-4,5,6,7-tetrahydro-[1,2,3]triazolo[1,5-a]pyridin-3-yl)-2-methylpyrimidin-4(3H)-one, (S)-6-(7-(4-Ethyl-2-fluorophenyl)-7-methyl-4,5,6,7-tetrahydro-triazolo[1,5-a]pyridin-3-yl)-2-methylpyrimidin-4(3H)-one, (R)-6-(6-(2-Fluoro-4-(trifluoromethyl)phenyl)-6-methyl-5,6-dihydro-4H-pyrrolo[1,2-c][1,2,3]triazol-3-yl)-2-methylpyrimidin-4(3H)-one, (S)-6-(6-(2-Fluoro-4-(trifluoromethyl)phenyl)-6-methyl-5,6-dihydro-4H-pyrrolo[1,2-c][1,2,3]triazol-3-yl)-2-methylpyrimidin-4(3H)-one, or a pharmaceutically acceptable salt and solvate thereof.

18. A pharmaceutical composition which comprises a pharmaceutically acceptable carrier and a compound of claim 1 or a pharmaceutically acceptable salt or solvate thereof.

19. A compound of claim 1 or a pharmaceutically acceptable salt or solvate thereof for use in medicine.

20. A method of treating diseases modulated by PDE2 inhibitors selected from psychotic disorders, delusional disorders and drug induced psychosis; anxiety disorders, movement disorders, mood disorders, Alzheimer's disease, schizophrenia, migraines, Huntington's disease, Parkinson's disease, Parkinson's disease dementia (PDD), and neurodegenerative disorders comprising administering a compound of claim 1 or a pharmaceutically acceptable salt or solvate thereof.

* * * * *